(12) United States Patent
Ashton et al.

(10) Patent No.: US 7,265,128 B2
(45) Date of Patent: Sep. 4, 2007

(54) 3-AMINO-4-PHENYLBUTANOIC ACID DERIVATIVES AS DIPEPTIDYL PEPTIDASE INHIBITORS FOR THE TREATMENT OR PREVENTION OF DIABETES

(75) Inventors: Wallace T. Ashton, Edison, NJ (US); Charles G. Caldwell, Scotch Plains, NJ (US); Robert J. Mathvink, Red Bank, NJ (US); Hyun O. Ok, Colonia, NJ (US); Leah Bitalac Reigle, Dayton, NJ (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 115 days.

(21) Appl. No.: 10/542,214

(22) PCT Filed: Jan. 13, 2004

(86) PCT No.: PCT/US2004/000763

§ 371 (c)(1),
(2), (4) Date: Jul. 14, 2005

(87) PCT Pub. No.: WO2004/064778

PCT Pub. Date: Aug. 5, 2004

(65) Prior Publication Data

US 2006/0069116 A1   Mar. 30, 2006

Related U.S. Application Data

(60) Provisional application No. 60/440,732, filed on Jan. 17, 2003.

(51) Int. Cl.
*A61K 31/4365* (2006.01)
*C07D 513/04* (2006.01)

(52) U.S. Cl. ............... 514/301; 546/114; 546/113; 546/115; 546/117; 546/118; 546/120; 514/300; 514/302; 514/303

(58) Field of Classification Search .......... 514/301, 514/300, 302, 303; 546/114, 113, 115, 117, 546/118, 120
See application file for complete search history.

(56) References Cited

U.S. PATENT DOCUMENTS

| | | | |
|---|---|---|---|
| 4,386,090 A | 5/1983 | Moinet et al. | |
| 5,939,560 A | 8/1999 | Jenkins et al. | |
| 6,011,155 A | 1/2000 | Villhauer | |
| 6,166,063 A | 12/2000 | Villhauer | |
| 6,265,418 B1 | 7/2001 | Kuroki et al. | |
| 6,303,661 B1 | 10/2001 | Demuth et al. | |
| 6,432,969 B1 | 8/2002 | Villhauer | |
| 6,699,871 B2 | 3/2004 | Edmondson et al. | |
| 7,157,490 B2 * | 1/2007 | Colandrea et al. | 514/423 |

FOREIGN PATENT DOCUMENTS

| | | |
|---|---|---|
| WO | WO97/40832 | 11/1997 |
| WO | WO98/19998 A2 | 5/1998 |
| WO | WO98/19998 A3 | 5/1998 |
| WO | WO 00/34241 | 6/2000 |
| WO | WO 01/34594 A1 | 5/2001 |
| WO | WO 01/42262 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 2005/002530 A2 | 1/2003 |
| WO | WO 03/082817 A2 | 10/2003 |
| WO | WO 2004/007468 | 1/2004 |
| WO | WO 2004/007468 A1 | 1/2004 |
| WO | WO 2004/032836 A2 | 4/2004 |

(Continued)

OTHER PUBLICATIONS

J. J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166, 2004.
C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102, 2004.
K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510, 2003.

(Continued)

*Primary Examiner*—Charanjit S. Aulakh
(74) *Attorney, Agent, or Firm*—Philippe L. Durette; Catherine D. Fitch

(57) ABSTRACT

The present invention is directed to 3-amino-4-phenylbutanoic acid derivatives of structural formula (I) which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

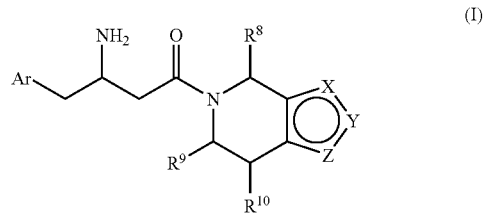

52 Claims, No Drawings

FOREIGN PATENT DOCUMENTS

| | | |
|---|---|---|
| WO | WO 2004/043940 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/112701 A2 | 12/2004 |
| WO | WO 2004/112701 A3 | 12/2004 |
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |

OTHER PUBLICATIONS

Novartis AG: WO0034241, "Novel N-substituted-2-Cyanopyrrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942, 2000.

O. J. Orucker, "Therapeutic potential of dipeptidyl peptidase IV inhibitors for the treatment of type 2 diabetes", Exp. Opin Invest. Drugs, vol. 12, 2004, pp. 87-100.

T. P. Vahl & D. A. D'Alessio, "Gut peptides in the treatment of diabetes mellitus" Exp. Opin. Invest. Drugs, vol. 13, 2004, pp. 177-188.

L. B. Knudsen, "Glucagon-like peptide-1: The Basis of a New Class of Treatment for Type 2 Diabetes", J. Med. Chem, vol. 47, 2004, pp. 4128-4134.

Ann E. Weber, "Dipeptidyl Peptidase IV Inhibitors for the Treatment of Diabetes", J. Med. Chem, vol. 47, 2004, pp. 4135-4141.

J. J. Holst and C. F. Deacon, "Glucagon-like peptide 1 and inhibitors of dipeptidyl peptidase IV in the treatment of type 2 diabetes mellitus", Curr. Opin Pharmacology, vol. 4, 2004, pp. 589-596.

C. F. Deacon, "Perspectives in Diabetes—Therapeutic Strategies Based on Glucagon-Like Peptide 1", Diabetes, vol. 53, Sep. 2004, pp. 2181-2189.

Kuroki, et al, DAtabase CAPLUS on STN No. 130:1685654, 1999.

Burger, A Guide to the Chemical Basis of Drug Design, p. 15 (1983).

* cited by examiner

3-AMINO-4-PHENYLBUTANOIC ACID DERIVATIVES AS DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US04/000763, filed 13 Jan. 2004, which claims the benefit under 35 U.S.C. 119(e) of U.S. Provisional Application No. 60/440,732, filed 17 Jan. 2003.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.* 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-WV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to 3-amino-4-phenylbutanoic acid derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to 3-amino-4-phenylbutanoic acid derivatives useful as inhibitors of dipeptidyl peptidase-IV. Compounds of the present invention are described by structural formula I:

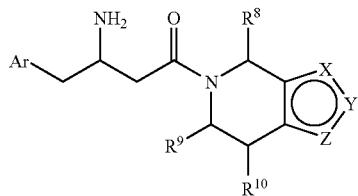

or a pharmaceutically acceptable salt thereof; wherein
each n is independently 0, 1, or 2;
X, Y and Z are independently selected from the group consisting of:
(1) $CR^1$,
(2) $NR^2$,
(3) N,
(4) O, and
(5) S;
with the provisos that at least one of X, Y and Z is not $CR^1$ and two of X, Y, and Z cannot be O and/or S;
Ar is phenyl substituted with one to five $R^3$ substituents;
each $R^1$ is independently selected from the group consisting of
hydrogen,
halogen,
hydroxy,
cyano,
$C_{1-10}$ alkyl, wherein alkyl is unsubstituted or substituted with one to five substituents independently selected from halogen or hydroxy,
$C_{1-10}$ alkoxy, wherein alkoxy is unsubstituted or substituted with one to five substituents independently selected from halogen or hydroxy,
$C_{1-10}$ alkylthio, wherein alkylthio is unsubstituted or substituted with one to five substituents independently selected from halogen or hydroxy,
$C_{2-10}$ alkenyl, wherein alkenyl is unsubstituted or substituted with one to five substituents independently selected from halogen, hydroxy, COOH, and $COOC_{1-6}$ alkyl,
$(CH_2)_n COOH$,
$(CH_2)_n COOC_{1-6}$ alkyl,
$(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
$(CH_2)_n$—$NR^4R^5$,
$(CH_2)_n$—$OCONR^4R^5$,
$(CH_2)_n$—$SO_2NR^4R^5$,
$(CH_2)_n$—$SO_2R^6$,
$(CH_2)_n$—$NR^7SO_2R^6$,
$(CH_2)_n$—$NR^7CONR^4R^5$,
$(CH_2)_n$—$NR^7COR^7$,
$(CH_2)_n$—$NR^7CO_2R^6$,
$(CH_2)_n$—$COR^7$,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $COOC_{1-6}$ alky, $C_{1-6}$ alkyl, and
$C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens;
each $R^2$ is independently selected from the group consisting of
hydrogen,
$C_{1-10}$ alkyl, wherein alkyl is unsubstituted or substituted with one to five substituents independently selected from halogen or hydroxy,
$C_{2-10}$ alkenyl, wherein alkenyl is unsubstituted or substituted with one to five substituents independently selected from halogen or hydroxy,
$(CH_2)_n COOH$,
$(CH_2)_n COOC_{1-6}$ alkyl,
$(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOC_{1-6}$ alkyl, $C_{1-6}$ alkyl, and $C_{1-6}$ alkoxy, wherein alkyl and alkoxy are unsubstituted or substituted with one to five halogens or one phenyl;

$(CH_2)_n$—$COR^7$, $(CH_2)_n$—$SO_2NR^4R^5$, $(CH_2)_n$—$SO_2R^6$, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens;

each $R^3$ is independently selected from the group consisting of hydrogen, halogen, cyano, hydroxy, $C_{1-6}$ alkyl, unsubstituted or substituted with one to five halogens, and $C_{1-6}$ alkoxy, unsubstituted or substituted with one to five halogens;

$R^6$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

each $R^7$ is hydrogen or $R^6$;

$R^8$, $R^9$ and $R^{10}$ are each independently selected from the group consisting of hydrogen, cyano, $(CH_2)_n COOH$, $(CH_2)_n COOC_{1-6}$ alkyl, $C_{1-10}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens, $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and $(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOC_{1-6}$ alkyl, $C_{1-6}$ alkyl, and $C_{1-6}$ alkoxy, wherein alkyl and alkoxy are unsubstituted or substituted with one to five halogens or one phenyl; and wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

In one embodiment of the compounds of the present invention, the carbon atom marked with an * has the R stereochemical configuration as depicted in formula Ia

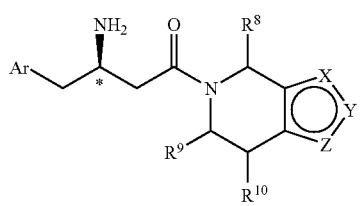

wherein Ar, X, Y, Z, $R^8$, $R^9$, and $R^{10}$ are as defined herein.

In a second embodiment of the compounds of the present invention, X and Y are independently C—$R^1$ and Z is S as depicted in formula Ib:

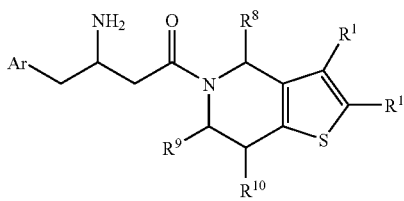

wherein Ar, $R^1$, $R^8$, $R^9$, and $R^{10}$ are as defined herein.

In a class of this second embodiment, the carbon atom marked with an * has the R stereochemical configuration as depicted in formula Ic:

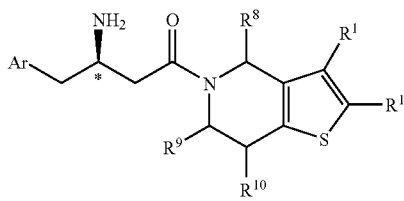

wherein Ar, $R^1$, $R^8$, $R^9$, and $R^{10}$ are as defined herein.

In another class of this second embodiment of the compounds of the present invention, $R^9$ and $R^{10}$ are hydrogen as depicted in formula Id:

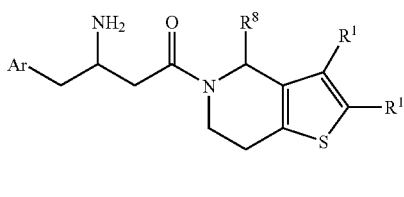

wherein Ar, $R^1$, $R^2$, and $R^8$ are as defined herein.

In a subclass of this class, $R^8$ is hydrogen.

In a third embodiment of the compounds of the present invention, X is $CR^1$, Y is N, and Z is $NR^2$ as depicted in formula Ie:

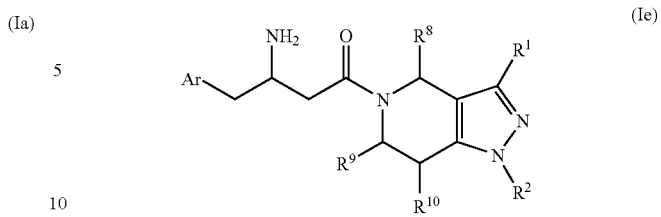

wherein Ar, $R^1$, $R^2$, $R^8$, $R^9$, and $R^{10}$ are as defined herein.

In a class of this third embodiment, the carbon atom marked with an * has the R stereochemical configuration as depicted in formula If:

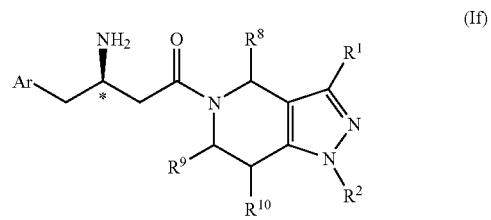

wherein Ar, $R^1$, $R^2$, $R^8$, $R^9$, and $R^{10}$ are as defined herein.

In another class of this third embodiment of the compounds of the present invention, $R^9$ and $R^{10}$ are hydrogen as depicted in formula Ig:

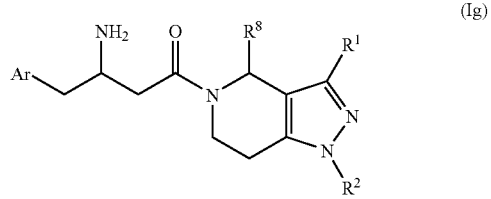

wherein Ar, $R^1$, $R^2$, and $R^8$ are as defined herein.

In a subclass of this class, $R^8$ is hydrogen.

In a fourth embodiment of the compounds of the present invention, X is $NR^2$, Y is N, and Z is $CR^1$ as depicted in formula Ih:

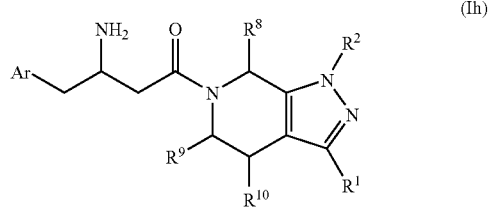

wherein Ar, $R^1$, $R^2$, $R^8$, $R^9$, and $R^{10}$ are as defined herein.

In a class of this fourth embodiment, the carbon atom marked with an * has the R stereochemical configuration as depicted in formula Ii:

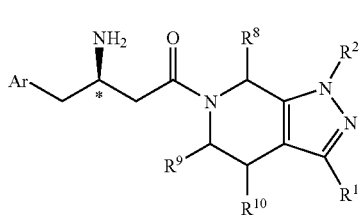

wherein Ar, $R^1$, $R^2$, $R^8$, $R^9$, and $R^{10}$ are as defined herein.

In another class of this fourth embodiment of the compounds of the present invention, $R^9$ and $R^{10}$ are hydrogen as depicted in formula Ij:

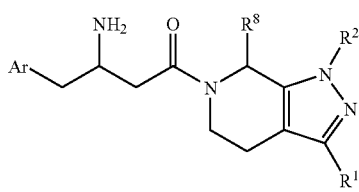

wherein Ar, $R^1$, $R^2$, and $R^8$ are as defined herein.

In a subclass of this class, $R^8$ is hydrogen.

In a fifth embodiment of the compounds of the present invention, X is $CR^1$, Y is O, and Z is N as depicted in formula Ik:

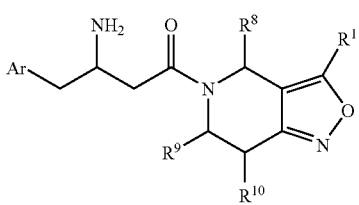

wherein Ar, $R^1$, $R^8$, $R^9$, and $R^{10}$ are as defined herein.

In a class of this fifth embodiment, the carbon atom marked with an * has the R stereochemical configuration as depicted in formula Il:

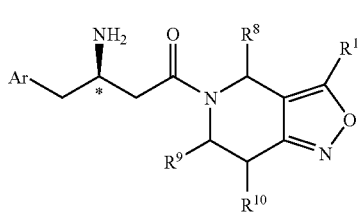

wherein Ar, $R^1$, $R^8$, $R^9$, and $R^{10}$ are as defined herein.

In another class of this fifth embodiment of the compounds of the present invention, $R^9$ and $R^{10}$ are hydrogen as depicted in formula Im:

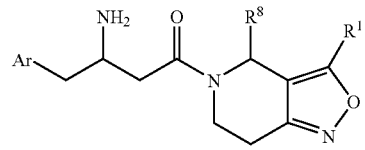

wherein Ar, $R^1$, and $R^8$ are as defined herein.

In a subclass of this class, $R^8$ is hydrogen.

In a sixth embodiment of the compounds of the present invention, X is N, Y is O, and Z is $CR^1$ as depicted in formula In:

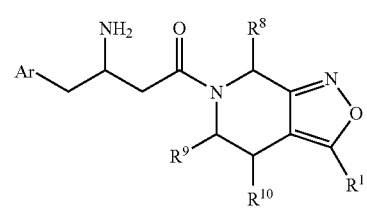

wherein Ar, $R^1$, $R^8$, $R^9$, and $R^{10}$ are as defined herein.

In a class of this sixth embodiment, the carbon atom marked with an * has the R stereochemical configuration as depicted in formula Io:

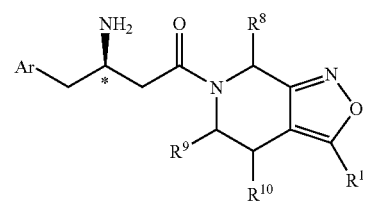

wherein Ar, $R^1$, $R^8$, $R^9$, and $R^{10}$ are as defined herein.

In another class of this sixth embodiment of the compounds of the present invention, $R^9$ and $R^{10}$ are hydrogen as depicted in formula Ip:

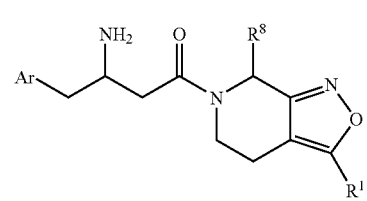

wherein Ar, $R^1$, and $R^8$ are as defined herein.

In a subclass of this class, $R^8$ is hydrogen.

In a seventh embodiment of the compounds of the present invention, X is S, Y is $CR^1$, and Z is N as depicted in formula Iq:

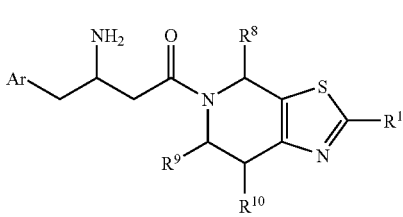

(Iq)

wherein Ar, $R^1$, $R^8$, $R^9$, and $R^{10}$ are as defined herein.

In a class of this seventh embodiment, the carbon atom marked with an * has the R stereochemical configuration as depicted in formula Ir:

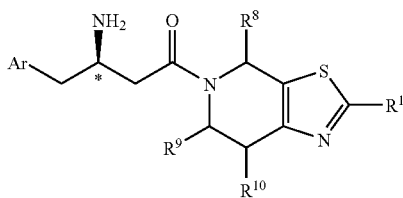

(Ir)

wherein Ar, $R^1$, $R^8$, $R^9$, and $R^{10}$ are as defined herein.

In another class of this seventh embodiment of the compounds of the present invention, $R^9$ and $R^{10}$ are hydrogen as depicted in formula Is:

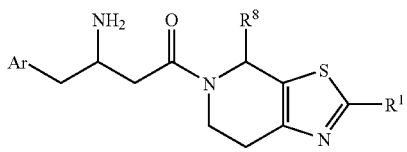

(Is)

wherein Ar, $R^1$, and $R^8$ are as defined herein.

In a subclass of this class, $R^8$ is hydrogen.

In an eighth embodiment of the compounds of the present invention, X is N, Y is $CR^1$, and Z is S as depicted in formula It:

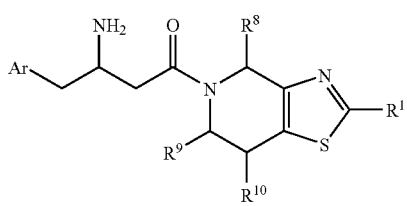

(It)

wherein Ar, $R^1$, $R^8$, $R^9$, and $R^{10}$ are as defined herein.

In a class of this eighth embodiment, the carbon atom marked with an * has the R stereochemical configuration as depicted in formula Iu:

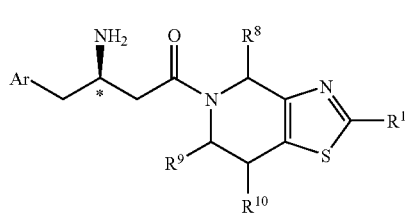

(Iu)

wherein Ar, $R^1$, $R^8$, $R^9$, and $R^{10}$ are as defined herein.

In another class of this eighth embodiment of the compounds of the present invention, $R^9$ and $R^{10}$ are hydrogen as depicted in formula Iv:

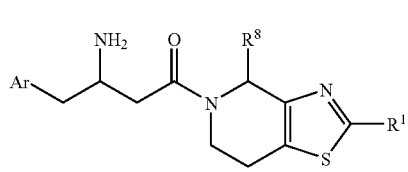

(Iv)

wherein Ar, $R^1$, and $R^8$ are as defined herein.

In a subclass of this class, $R^8$ is hydrogen.

In a ninth embodiment of the compounds of the present invention, X is N, Y is $CR^1$, and Z is O as depicted in formula Iw:

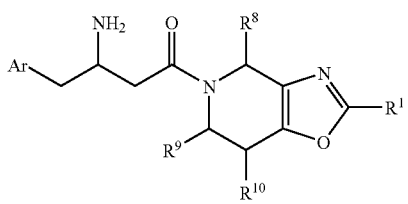

(Iw)

wherein Ar, $R^1$, $R^8$, $R^9$, and $R^{10}$ are as defined herein.

In a class of this ninth embodiment, the carbon atom marked with an * has the R stereochemical configuration as depicted in formula Ix:

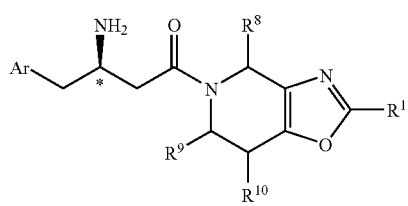

(Ix)

wherein Ar, $R^1$, $R^8$, $R^9$, and $R^{10}$ are as defined herein.

In another class of this ninth embodiment of the compounds of the present invention, $R^9$ and $R^{10}$ are hydrogen as depicted in formula Iy:

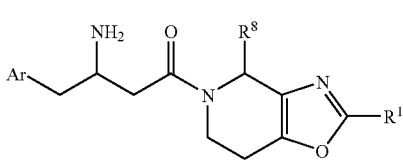
(Iy)

wherein Ar, $R^1$, and $R^8$ are as defined herein.

In a subclass of this class, $R^8$ is hydrogen.

In a tenth embodiment of the compounds of the present invention, X is O, Y is $CR^1$, and Z is N as depicted in formula Iz:

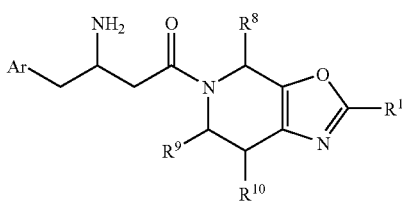
(Iz)

wherein Ar, $R^1$, $R^8$, $R^9$, and $R^{10}$ are as defined herein.

In a class of this tenth embodiment, the carbon atom marked with an * has the R stereochemical configuration as depicted in formula Iaa:

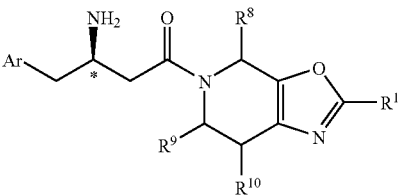
(Iaa)

wherein Ar, $R^1$, $R^8$, $R^9$, and $R^{10}$ are as defined herein.

In another class of this tenth embodiment of the compounds of the present invention, $R^9$ and $R^{10}$ are hydrogen as depicted in formula Iab:

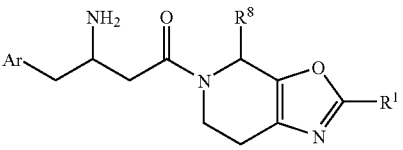
(Iab)

wherein Ar, $R^1$, and $R^8$ are as defined herein.

In a subclass of this class, $R^8$ is hydrogen.

In an eleventh embodiment of the compounds of the present invention, X is $NR^2$, Y is $CR^1$, and Z is N as depicted in formula Iac:

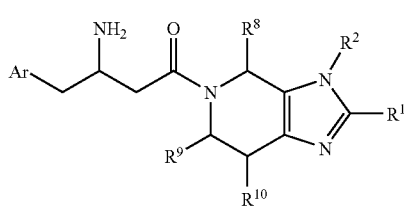
(Iac)

wherein Ar, $R^1$, $R^2$, $R^8$, $R^9$, and $R^{10}$ are as defined herein.

In a class of this eleventh embodiment, the carbon atom marked with an * has the R stereochemical configuration as depicted in formula Iad:

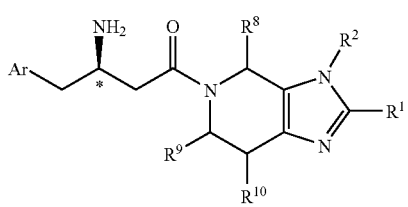
(Iad)

wherein Ar, $R^1$, $R^2$, $R^8$, $R^9$, and $R^{10}$ are as defined herein.

In another class of this eleventh embodiment of the compounds of the present invention, $R^9$ and $R^{10}$ are hydrogen as depicted in formula Iae:

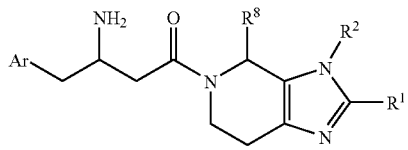
(Iae)

wherein Ar, $R^1$, $R^2$, and $R^8$ are as defined herein.

In a subclass of this class, $R^8$ is hydrogen.

In a twelfth embodiment of the compounds of the present invention, X is N, Y is $CR^1$, and Z is $NR^2$ as depicted in formula Iaf:

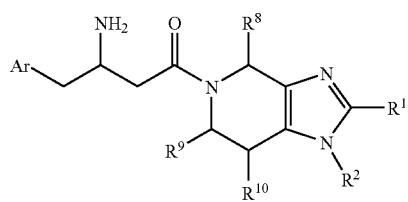
(Iaf)

wherein Ar, $R^1$, $R^2$, $R^8$, $R^9$, and $R^{10}$ are as defined herein.

In a class of this twelfth embodiment, the carbon atom marked with an * has the R stereochemical configuration as depicted in formula Iag:

(Iag)

wherein Ar, $R^1$, $R^2$, $R^8$, $R^9$, and $R^{10}$ are as defined herein.

In another class of this twelfth embodiment of the compounds of the present invention, $R^9$ and $R^{10}$ are hydrogen as depicted in formula Iah:

(Iah)

wherein Ar, $R^1$, $R^2$, and $R^8$ are as defined herein.

In a subclass of this class, $R^8$ is hydrogen.

In a thirteenth embodiment of the compounds of the present invention, X is $NR^2$, Y is N, and Z is N as depicted in formula Iai:

(Iai)

wherein Ar, $R^2$, $R^8$, $R^9$, and $R^{10}$ are as defined herein.

In a class of this thirteenth embodiment, the carbon atom marked with an * has the R stereochemical configuration as depicted in formula Iaj:

(Iaj)

wherein Ar, $R^2$, $R^8$, $R^9$, and $R^{10}$ are as defined herein.

In another class of this thirteenth embodiment of the compounds of the present invention, $R^9$ and $R^{10}$ are hydrogen as depicted in formula Iak:

(Iak)

wherein Ar, $R^2$, and $R^8$ are as defined herein.

In a subclass of this class, $R^8$ is hydrogen.

In a fourteenth embodiment of the compounds of the present invention, X is N, Y is N, and Z is $NR^2$ as depicted in formula Ial:

(Ial)

wherein Ar, $R^2$, $R^8$, $R^9$, and $R^{10}$ are as defined herein.

In a class of this fourteenth embodiment, the carbon atom marked with an * has the R stereochemical configuration as depicted in formula Iam:

(Iam)

wherein Ar, $R^2$, $R^8$, $R^9$, and $R^{10}$ are as defined herein.

In another class of this fourteenth embodiment of the compounds of the present invention, $R^9$ and $R^{10}$ are hydrogen as depicted in formula Ian:

(Ian)

wherein Ar, $R^2$, and $R^8$ are as defined herein.

In a subclass of this class, $R^8$ is hydrogen.

In a fifteenth embodiment of the compounds of the present invention, $R^3$ is selected from the group consisting of hydrogen, fluoro, chloro, bromo, trifluoromethyl, and methyl. In a class of this embodiment, $R^3$ is selected from the group consisting of hydrogen, fluoro, and chloro.

In a sixteenth embodiment of the compounds of the present invention, $R^1$ is selected from the group consisting of:
hydrogen,
halogen,
hydroxy,
$C_{1-10}$ alkyl, wherein alkyl is unsubstituted or substituted with one to five substituents independently selected from halogen or hydroxy,
$C_{2-10}$ alkenyl, wherein alkenyl is unsubstituted or substituted with one to five substituents independently selected from halogen, hydroxy, COOH, and $COOC_{1-6}$ alkyl,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and
$(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $COOC_{1-6}$ alkyl, $C_{1-6}$ alkyl, and
$C_{1-6}$ alkoxy, wherein alkyl and alkoxy are unsubstituted or substituted with one to five halogens, and
wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^1$ is selected from the group consisting of
hydrogen,
methyl,
ethyl,
trifluoromethyl,
$CH_2CF_3$,
$CF_2CF_3$,
phenyl,
4-(methoxycarbonyl)phenyl,
4-fluorophenyl,
4-(trifluoromethyl)phenyl,
4-(methylsulfonyl)phenyl,
cyclopropyl,
fluoro,
chloro,
bromo, and
2-(methoxycarbonyl)vinyl.

In a seventeenth embodiment of the compounds of the present invention, $R^2$ is selected from the group consisting of
hydrogen,
$C_{1-6}$ alkyl, wherein alkyl is unsubstituted or substituted with one to five substituents independently selected from halogen or hydroxy,
$(CH_2)_n$-aryl, wherein aryl is unsubstituted or substituted with one to five substituents independently selected from halogen, CN, hydroxy, $NR^7SO_2R^6$, $SO_2R^6$, $CO_2H$, $COOC_{1-6}$ alkyl, $C_{1-6}$ alkyl, and
$C_{1-6}$ alkoxy, wherein alkyl and alkoxy are unsubstituted or substituted with one to five halogens; and
wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^2$ is selected from the group consisting of:
hydrogen,
methyl,
$CH_2CF_3$,
isobutyl,
4-(trifluoromethyl)benzyl, and
4-fluorobenzyl.

In an eighteenth embodiment of the compounds of the present invention, $R^8$, $R^9$, and $R^{10}$ are independently selected from the group consisting of:
hydrogen,
$C_{1-10}$ alkyl, unsubstituted or substituted with one to five substituents independently selected from halogen, hydroxy, $C_{1-6}$ alkoxy,
and phenyl-$C_{1-13}$ alkoxy, wherein alkoxy is unsubstituted or substituted with one to five halogens,
$(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and
wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^8$, $R^9$, and $R^{10}$ are each independently selected from the group consisting of
hydrogen,
trifluoromethyl,
methyl,
ethyl,
cyclopropyl,
$CH_2$-Ph, and
$CH_2$(4-F-Ph).

In a subclass of this class, $R^9$ and $R^{10}$ are hydrogen. In a subclass of this subclass, $R^8$ is hydrogen.

Illustrative, but nonlimiting, examples of compounds of the present invention that are useful as dipeptidyl peptidase-IV inhibitors are the following:

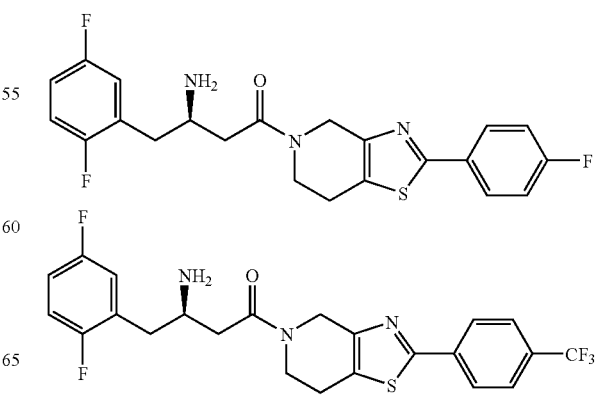

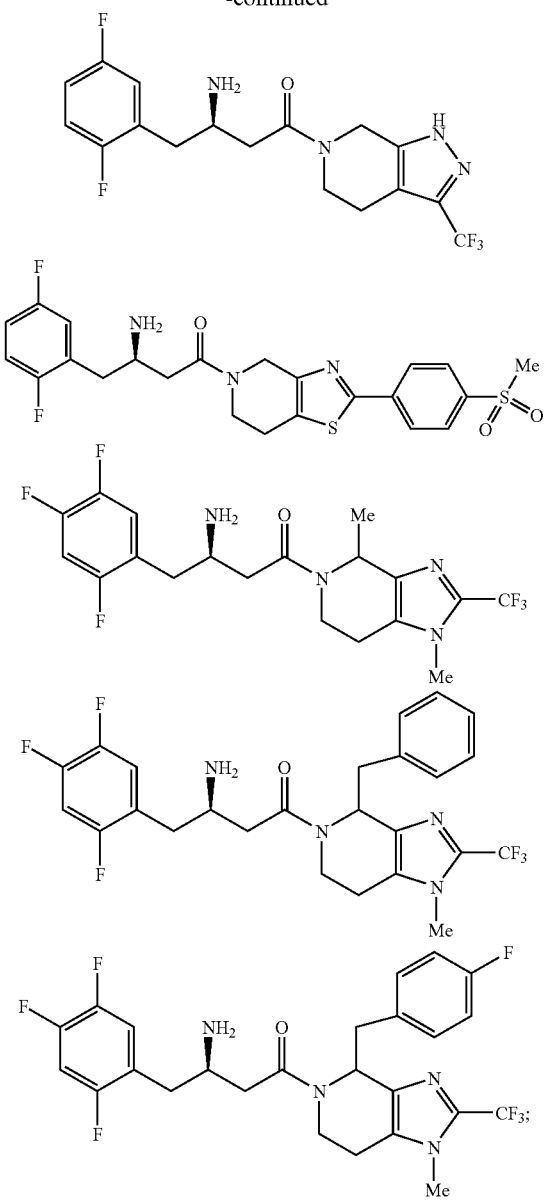

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ $\mu M$; $k_{cat}=75$ s$^{-1}$; $k_{cat}/K_m=1.5\times10^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors of the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DP-IV inhibitors may also be useful to treat hypertension associated with this condition.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides*. 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation*, 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DP-IV would be expected to decrease MV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ M$^{-1}$s$^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)). Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MOP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety

Rats naturally deficient in DP-IV have an anxiolytic phenotype (WO 02/34243; Karl et al., *Physiol. Behav.* 2003). DP-IV deficient mice also have an anxiolytic phenotype using the Porsolt and light/dark models. Thus DP-IV inhibitors may prove useful for treating anxiety and related disorders.

Memory and Cognition

GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DP-IV inhibitors are expected to show similar effects.

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.* 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, balaglitazone, and the like) and other PPAR ligands, including PPARα/γ dual agonists, such as KRP-297 and muraglitazar, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepilide, and meglitinides, such as nateglinide and repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, such as Exendin 4, and liraglutide, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors;

(o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers; and (p) glucokinase activators (GKAs).

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/0708 (27 Sep. 2001); and WO 01/0337 (27 Sep. 2001) as well as those disclosed in J. D. Speake et al., "Recent advances in the development of melanocortin-4 receptor agonists," *Expert Opin. Ther. Patents*, 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted heterocyclic intermediates such as those of formula III, using standard peptide coupling conditions followed by deprotection. The preparation of these intermediates is described in the following schemes.

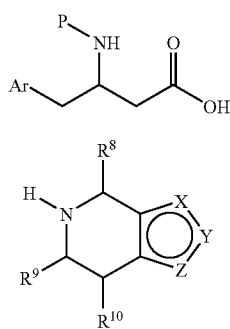

where Ar, X, Y, Z, $R^8$, $R^9$ and $R^{10}$ are as defined above and P is a suitable nitrogen protecting group such as tert-butoxycarbonyl, benzyloxycarbonyl, and 9-fluorenylmethoxycarbonyl.

SCHEME 1

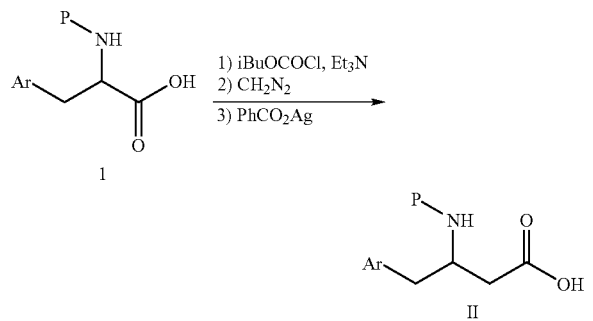

Compounds of formula II are commercially available, known in the literature or may be conveniently prepared by a variety of methods familiar to those skilled in the art. One common route is illustrated in Scheme 1. Protected alpha-amino acid 1, which may be commercially available or readily prepared from the corresponding amino acid by protection using, for example, di-tert-butyl dicarbonate (for P=BOC), carbobenzyloxy chloride (for P=Cbz), or N-(9-fluorenylmethoxycarbonyloxy)succinimide (for P=Fmoc), is treated with isobutyl chloroformate and a base such as triethylamine or N,N-diisopropylethylamine (DIEA), followed by diazomethane. The resultant diazoketone is then treated with silver benzoate in a solvent such as methanol or aqueous dioxane which may be subjected to sonication following the procedure of Sewald et al., *Synthesis*, 837 (1997) in order to provide the beta amino acid II. As will be understood by those skilled in the art, for the preparation of enantiomerically pure beta amino acids II, enantiomerically pure alpha amino acids 1 may be used. Alternate routes to the protected beta-amino acid intermediates II can be found in the following reviews: E. Juaristi, *Enantioselective Synthesis of β-Amino Acids*, Ed., Wiley-VCH, New York: 1997; Juaristi et al., *Aldrichimica Acta* 27: 3 (1994); and Cole et al., *Tetrahedron*, 32: 9517 (1994).

SCHEME 2

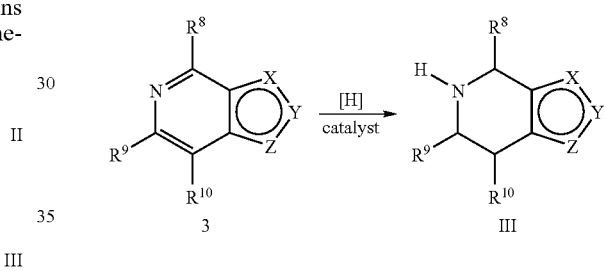

Compounds in are commercially available, known in the literature or may be conveniently prepared by a variety of methods familiar to those skilled in the art. One convenient method is shown in Scheme 2. Unsaturated derivative 3 is reduced, for example, by treatment with hydrogen gas and a catalyst such as palladium on carbon or platinum oxide in a solvent such as methanol or ethanol to provide Compound III.

SCHEME 3

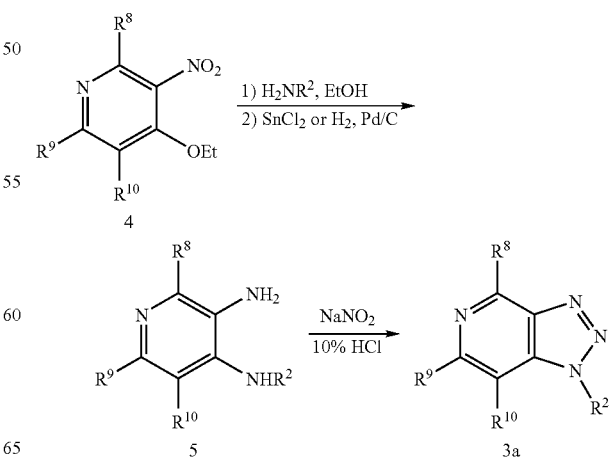

Intermediates 3, from Scheme 2, are themselves commercially available, known in the literature or may be conveniently prepared by a variety of methods familiar to those skilled in the art. One such method when X and Y are N and Z is $NR^2$ is illustrated in Scheme 3. Pyridine 4 is treated with a primary amine in a solvent such as ethanol typically with heating followed by reduction of the nitro group with tin(II) chloride, for example, in dimethylformamide at elevated temperature, or by catalytic hydrogenation to provide diamine 5. Treatment of diamine 5 with sodium nitrite in hydrochloric acid provides intermediate 3a, wherein X and Y are N and Z is $NR^2$.

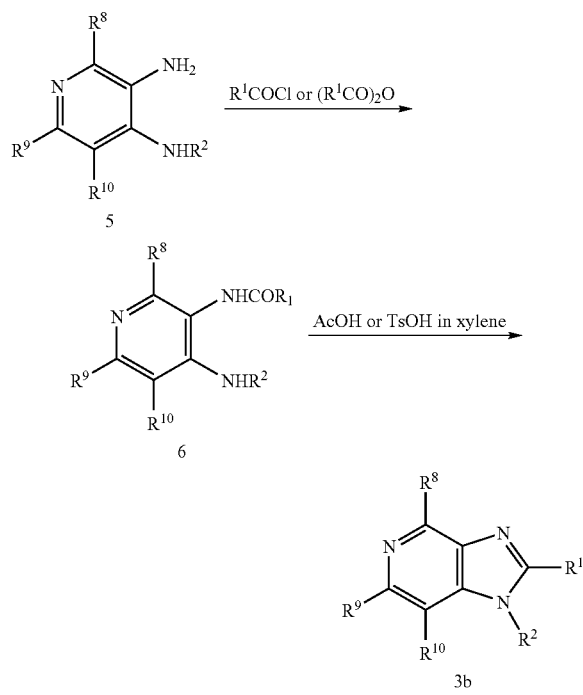

Intermediates 3b, wherein X is N, Y is $CR^1$ and Z is $NR^2$ may be prepared as illustrated in Scheme 4. Diamine 5, prepared as described in Scheme 3, is acylated with an appropriate acid chloride or anhydride to provide amide 6. Treatment at elevated temperature with acetic acid or with p-toluenesulfonic acid in a solvent such as xylene provides intermediate 3b, wherein X is N, Y is $CR^1$ and Z is $NR^2$. When $R^1$ is $CF_3$, diamine 5 may be converted directly to 3b by treatment with trifluoroacetic acid.

Intermediates 3c, wherein X is $NR^2$, Y is N and Z is N may be prepared as illustrated in Scheme 5. Fluoropyridine 7 is treated with hydrogen peroxide and the resultant N-oxide nitrated under standard conditions to provide nitro analog 8. The fluoride is displaced with an appropriate amine followed by treatment with phosphorus trichloride to give aminopyridine 9. Reduction of the nitro group with tin(II) chloride, for example in dimethylformamide at elevated temperature, or by catalytic hydrogenation provides diamine 10. Treatment of diamine 10 with sodium nitrite in hydrochloric acid provides intermediate 3c, wherein X is $NR^2$, Y is N and Z is N.

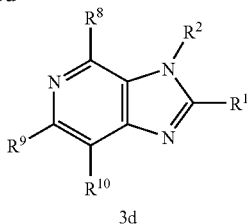

3d

Intermediates 3d, wherein X is NR², Y is CR¹ and Z is N may be prepared as illustrated in Scheme 6. Diamine 10, prepared as described in Scheme 5, is acylated with an appropriate acid chloride or anhydride to provide amide 11. Treatment at elevated temperature with acetic acid or with p-toluenesulfonic acid in a solvent such as xylene provides intermediate 3d, wherein X is NR², Y is CR¹ and Z is N. When R¹ is CF₃, diamine 11 may be converted directly to 3d by treatment with trifluoroacetic acid.

ethylsilyl chloride. Enol ether 13 may then be treated with methyllithium, and the resultant lithium enolate acylated by treatment with an appropriate acid chloride or anhydride to provide diketone 14. Treatment with a reagent HY-ZH, such as hydrazine (Y=Z=NH), N-methylhydrazine, or hydroxylamine under appropriate conditions such as refluxing ethanol, refluxing acetic acid, or in some cases sodium hydroxide in ethanol at elevated temperature, followed by deprotection, in the case of BOC, conveniently using hydrogen chloride in dioxane, provides compounds IIIa, wherein X is CR¹. In some cases, a hydrated analog of IIIa (or BOC-protected IIIa) may be isolated from this series of reactions. This hydrated derivative may be converted to IIIa (or BOC-protected IIIa), for example, by treatment with refluxing acetic acid. Alternatively, the hydrated analog of IIIa may be used as is and may undergo dehydration in the coupling reaction.

SCHEME 7

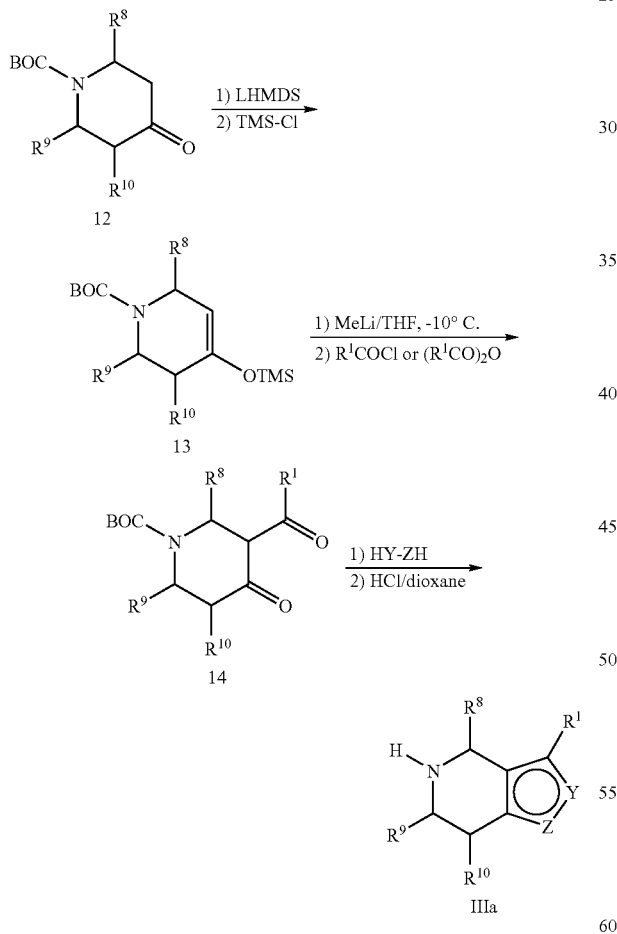

SCHEME 8

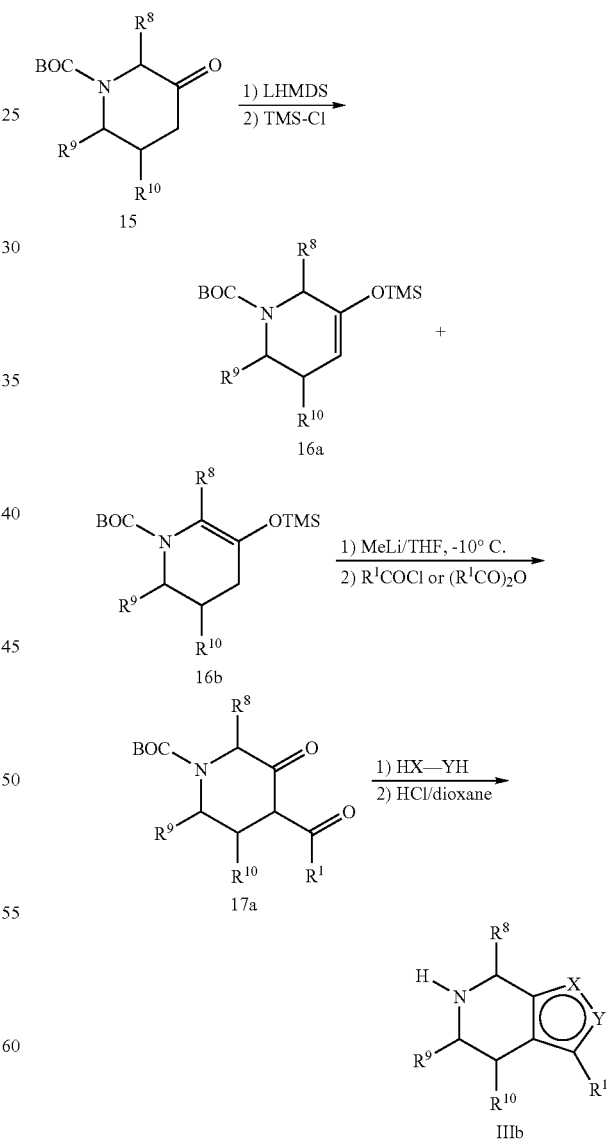

A useful route for the preparation of Compound IIIa wherein X is CR¹ is illustrated in Scheme 7. The N-protected 4-ketopiperidine derivative 12 is converted to trimethylsilyl enol ether 13, conveniently by treatment with a base such as lithium hexamethyldisilazide in an aprotic solvent such as THF at low temperature followed by quenching with trim- The synthesis of compound IIIb wherein Z is CR¹ is illustrated in Scheme 8. The N-protected 4-ketopiperidine derivative 15 is converted to trimethylsilyl enol ether 16a and its regioisomer 16b as described for the synthesis of enol ether 13 above. Conveniently, the mixture is used in the next steps and the undesired isomer separated chromatographically. Enol ether 16a may then be treated with methyllithium, and the resultant lithium enolate acylated by treatment with an appropriate acid chloride or anhydride to provide diketone 17a. Treatment with a reagent HX—YH, such as hydrazine (X=Y=NM, N-methylhydrazine, or hydroxylamine under appropriate conditions such as refluxing ethanol, refluxing acetic acid, or in some cases sodium hydroxide in ethanol at elevated temperature, followed by deprotection, in the case of BOC, conveniently using hydrogen chloride in dioxane, provides compounds IIIb, wherein Z is $CR^1$. In some cases, a hydrated analog of IIIb (or BOC-protected IIIb) may be isolated from this series of reactions. This hydrated derivative may be converted to IIIb (or BOC-protected IIIb), for example, by treatment with refluxing acetic acid. Alternatively, the hydrated analog of IIIb may be used as is and may undergo dehydration in the coupling reaction.

SCHEME 9

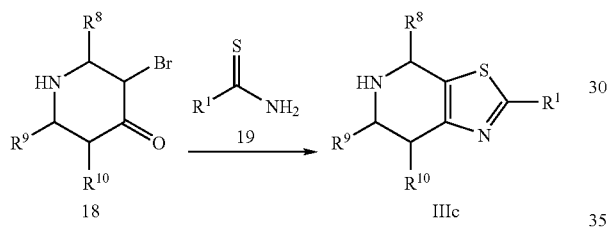

Compound IIIc, wherein X is S, Y is $CR^1$ and Z is N may be prepared from bromoketopiperidine 18 as illustrated in Scheme 9. Treatment of 18, which is commercially available, known in the literature or may be conveniently prepared by a variety of methods familiar to those skilled in the art, with thioamide 19, conveniently in a solvent such as DMF at elevated temperatures, for example, 100° C., provides IIIc. In some cases, a protecting group on nitrogen may be employed. One such protecting group is the 2-(trimethylsilyl)ethylsulfonyl group. Following reaction with thioamide 19, typically in refluxing benzene or toluene, this group may be removed by treatment with cesium fluoride.

SCHEME 10

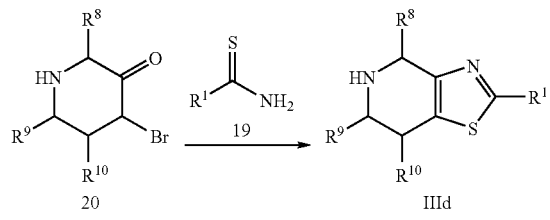

As illustrated in Scheme 10, compound IIId, wherein X is N, Y is $CR^1$ and Z is S may be prepared in an analogous fashion from the isomeric bromoketopiperidine 20 as described for the synthesis of IIIc in Scheme 9.

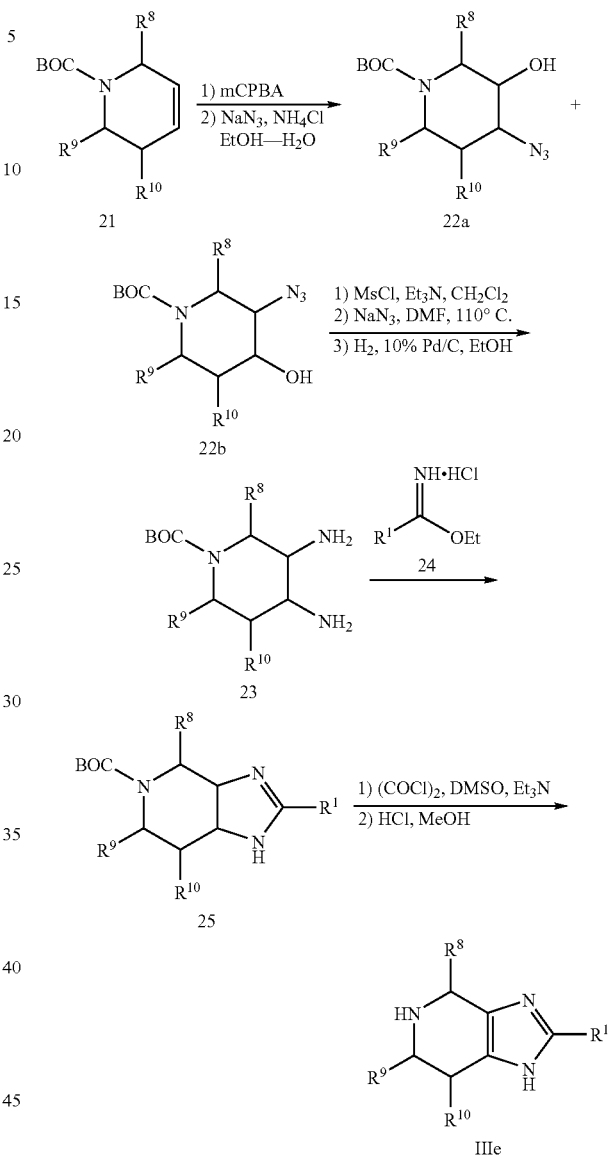

A useful method for the preparation of compound IIIe, wherein X is N, Y is C—$R^1$, and Z is N—H (and its tautomer) is illustrated in Scheme 11. The N-protected tetrahydropyridine 21 is epoxidized, conveniently using m-chloroperbenzoic acid, and the resultant epoxide opened with azide, for example by treatment with sodium azide and ammonium chloride in a polar solvent such as ethanol-water, to provide azidoalcohols 22a and 22b. Conversion to the corresponding diamine 23 may be achieved by treatment with methanesulfonyl chloride in the presence of a base such as triethylamine, then displacement of the resultant mesylate with sodium azide, conveniently in DMF at elevated temperatures, followed by reduction of the diazide, for example, by treatment with a catalyst such as palladium on carbon under an atmosphere of hydrogen. Treatment of 23 with imidate 24 provides hexahydroimidazopyridine 25. Oxidation, conveniently using Swern conditions, followed by deprotection, for example, in the case of BOC by treatment with methanolic hydrogen chloride, provides IIIe, wherein X is N, Y is C—$R^1$, and Z is N—H, and its tautomer.

SCHEME 12

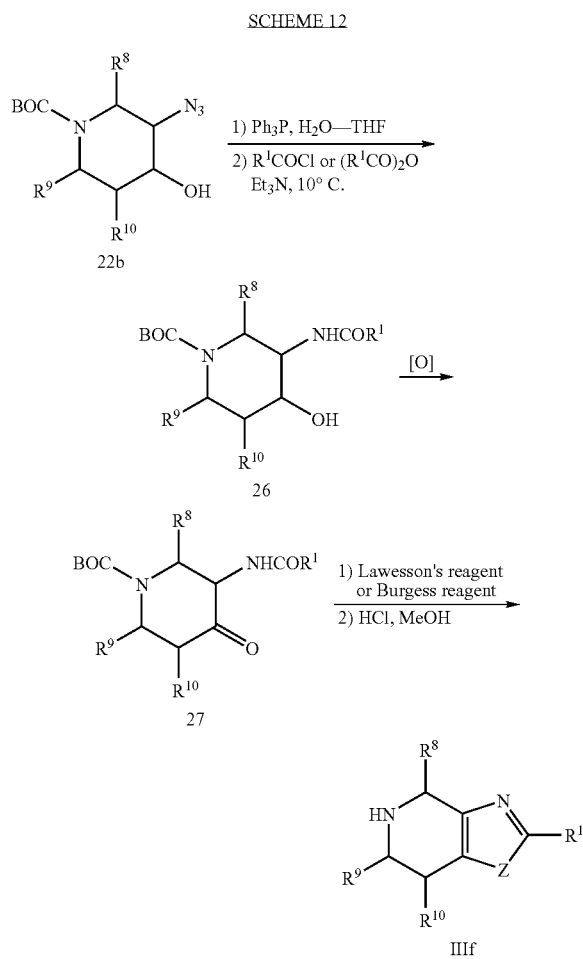

The synthesis of compound IIIf, wherein X is N, Y is C—R¹, and Z is either S or O is illustrated in Scheme 12. Azidoalcohol 22b, from Scheme 11, is reduced, for example by catalytic hydrogenation or by treatment with triphenylphosphine in a solvent such as aqueous tetrahydrofuran with warming, and the resultant amine acylated to provide amidoalcohol 26. Oxidation to ketone 27 may be achieved conveniently using Dess-Martin periodinane conditions to give ketone 27. Treatment of 27 with 2,4-bis(4-methoxyphenyl)-1,3-dithia-2,4-diphosphetane-2,4-disulfide (Lawesson's reagent) followed by deprotection under acidic conditions provides IIIf wherein Z is S. Alternatively, ketone 27 may be treated with (methoxycarbonylsulfamoyl)triethylammonium hydroxide (Burgess reagent) to give, following deprotection, IIIf wherein Z is O.

SCHEME 13

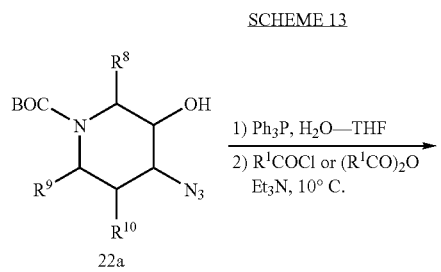

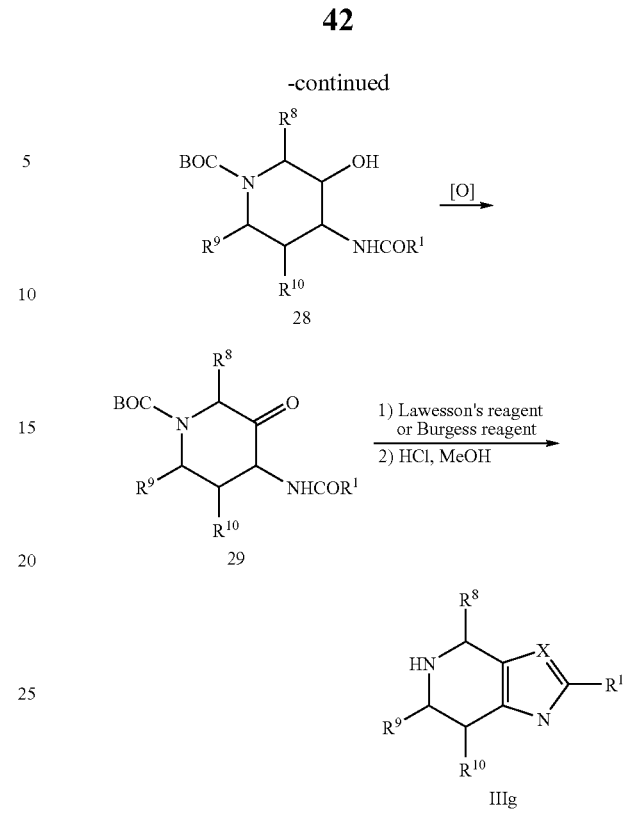

In an analogous fashion, compound IIIg, wherein X is either S or O, Y is C—R¹, and Z is N may be prepared from azidoalcohol 22a (Scheme 11) as illustrated in Scheme 13, following the route described above for Scheme 12. Treatment of ketone 29 with Lawesson's reagent followed by deprotection under acidic conditions provides IIIg wherein X is S. Treatment of ketone 29 with Burgess reagent gives, following deprotection, IIIg wherein X is O.

SCHEME 14

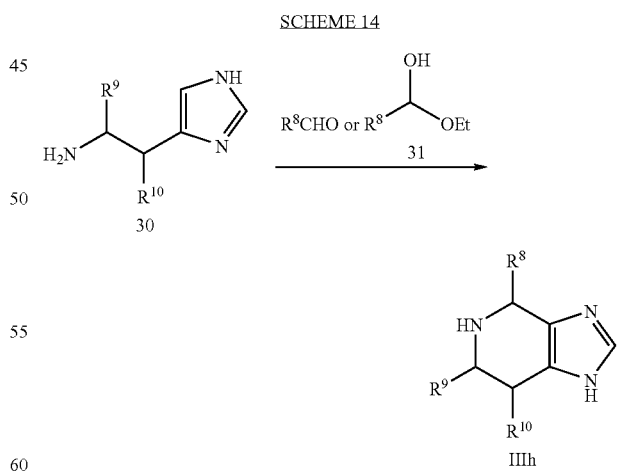

Compound IIIh, wherein X is N, Y is C—H, and Z is N—H (and its tautomer) is illustrated in Scheme 14. Histamine derivative 30 may be treated with an aldehyde or a hemiacetal 31, typically at elevated temperature, to provide IIIh and its tautomer.

SCHEME 15

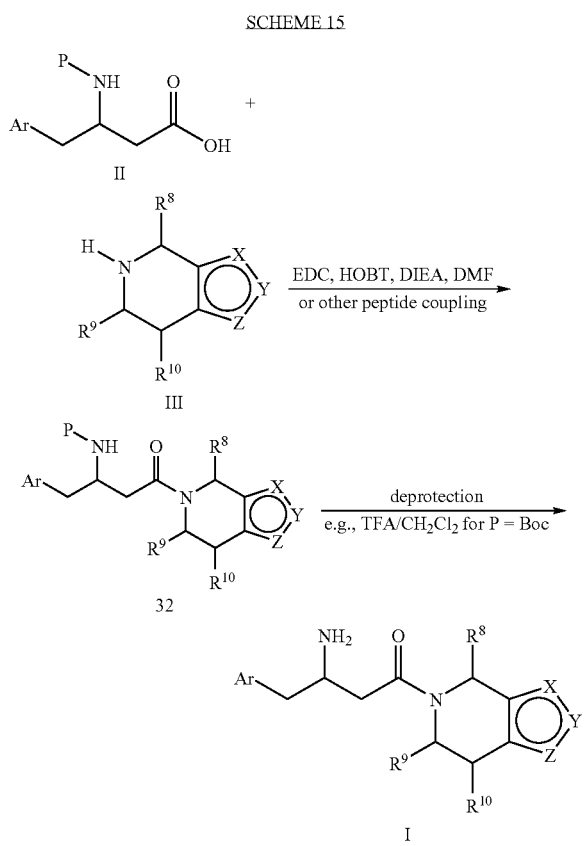

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N′,N′-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 32 as shown in Scheme 15. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I, prepared as described in Scheme 15, may be further modified, for example, by manipulation of substituents on Ar, $R^8$, $R^9$, $R^{10}$, X, Y, or Z These manipulations may include, but are not limited to, reduction, oxidation, alkylation, acylation, and hydrolysis reactions that are commonly known to those skilled in the art.

In some cases intermediates described in the above schemes may be further modified before the sequences are completed, for example, by manipulation of substituents on Ar, $R^8$, $R^9$, $R^{10}$, X, Y, or Z. These manipulations may include, but are not limited to, reduction, oxidation, alkylation, acylation, and hydrolysis reactions that are commonly known to those skilled in the art.

SCHEME 16

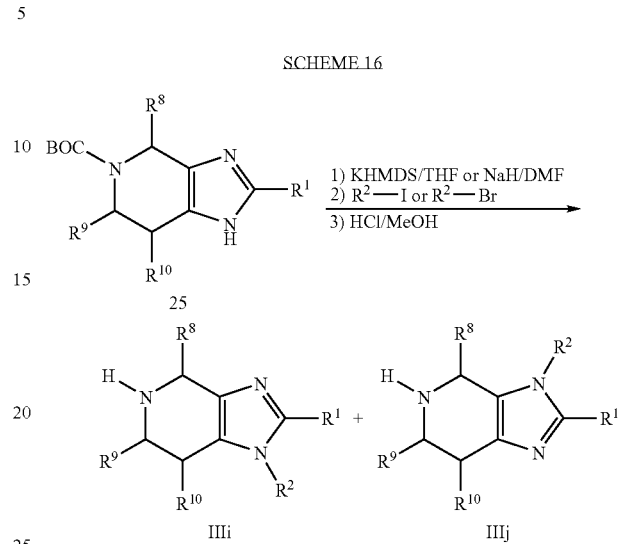

One such example is illustrated in Scheme 16. Intermediate 25, prepared as described in Scheme 11, or by N-protection of compound IIIh (Scheme 14), may be deprotonated with a strong base such as potassium hexamethyldisilazide in tetrahydrofuran or sodium hydride in dimethylformamide as shown in Scheme 16. Treatment of the resultant anion with an alkyl halide followed by deprotection under acidic conditions provides the alkylated derivatives IIIi and IIIj.

SCHEME 17

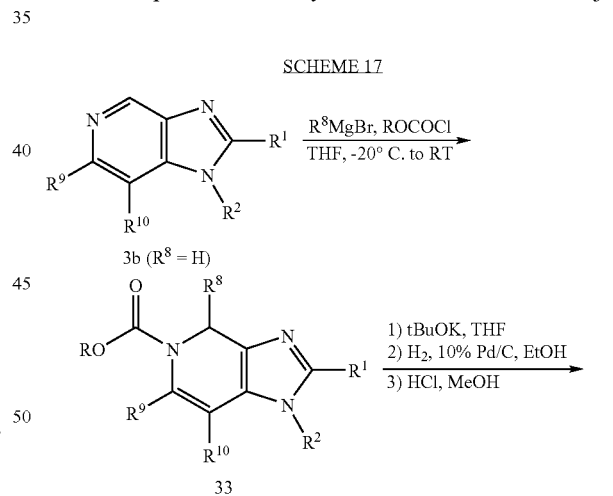

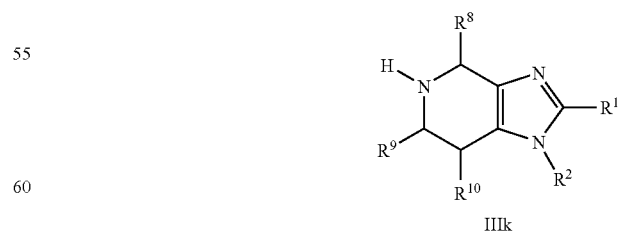

Another such example is shown in Scheme 17. Intermediate 3b, wherein $R^8$ is H, is prepared as described in Scheme 4. Treatment of 3b with a Grignard reagent and a chloroformate, conveniently phenylchloroformate, in a solvent such as tetrahydrofuran provides the alkylated carbamate 33. This may be converted to compound IIIk by treatment with potassium tert-butoxide to give the corresponding BOC derivative. Reduction followed by deprotection under acidic conditions provides IIIk.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

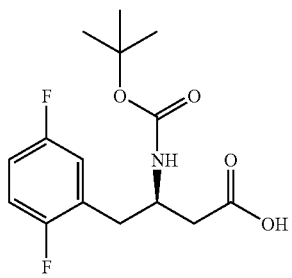

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane:methanol:acetic acid) to afford 671 mg of the title compound. LC/MS 302 (M+1).

Step B: (R,S)-3-[(tert-Butoxycarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded 1.5 g of the diazoketone.

$^1$H NMR (500 MHz, CDCl$_3$): δ 7.03-6.95 (m, 1H), 6.95-6.88 (m, 2H), 5.43 (bs, 1H), 5.18 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid

To a solution of 2.14 g (6.58 mmol) of (R,S)-3-[(tert-butoxycarbonyl)-amino]-1-diazo-4-(2,5-difluorophenyl)butan-2-one dissolved in 100 mL of methanol at −30° C. were added sequentially 3.3 mL (19 mmol) of N,N-diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate solution, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol:1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 360 mg of the title compound as a white foamy solid.

$^1$H NMR (500 MHz, CDCl$_3$): δ 7.21 (m, 1H), 6.98 (m, 2H), 6.10 (bs, 1H), 5.05 (m,1H), 4.21 (m, 1H), 2.98 (m, 2H), 2.60 (m, 2H), 1.38 (s, 9H).

INTERMEDIATE 2

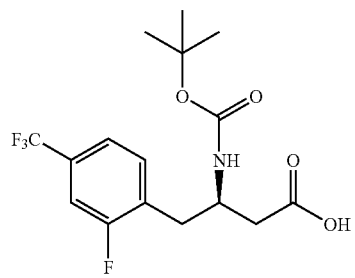

(3R)-3-[(tert-Butoxycarbonyl)amino]-4-[2-fluoro-4-(trifluoromethyl)phenyl]-butanoic acid Step A: (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded 5.5 g of the title compound.

$^1$H NMR (500 MHz, CDCl$_3$): δ 7.33-7.25 (m, 3H), 4.35-4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25-2.15 (m, 1H), 1.0 (d, 3H, J=7 Hz), 0.66 (d, 3H, J=7 Hz).

Step B: (R)-N-(tert-Butoxycarbonyl)-2-fluoro-4-trifluoromethyl-phenylalanine methyl ester To a solution of 5.5 g (15 mmol) of (2R,5S)-2,5-dihydro-3,6-dimethoxy-2-(2'-fluoro-4'-(trifluoromethyl)benzyl)-5- isopropylpyrazine in 50 mL of a mixture of acetonitrile: dichloromethane (10:1) was added 80 mL of 1N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resultant slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded 5.1 g of the title compound.

$^1$H NMR (500 MHz, CDCl$_3$) δ 7.38-7.28 (m, 3H), 5.10 (bd, 1H), 4.65-3.98 (m, 1H), 3.76 (s, 3H), 3.32-3.25 (m, 1H), 3.13-3.05 (m, 1H), 1.40 (s, 9H).

Step C: (R)-N-(tert-Butoxycarbonyl)-2-fluoro-4-trifluoromethyl)phenylalanine

A solution of 5.1 g (14 mmol) of (R,S)-N-(tert-butoxycarbonyl)-2-fluoro-4-trifluoromethyl)phenylalanine methyl ester in 350 mL of a mixture of tetrahydrofuran:methanol:1N lithium hydroxide (3:1:1) was stirred at 50° C. for 4 h. The reaction was cooled, acidified with 5% hydrochloric acid and extracted with ethyl acetate. The combined organic phases were washed with brine, dried over magnesium sulfate and concentrated in vacuo to give 4.8 g of the title compound.

$^1$H NMR (500 MHz, CD$_3$OD): δ 7.45-7.38 (m, 3H), 4.44-4.40 (m, 1H), 3.38-3.33 (m, 1H), 2.98 (dd, 1H, J=9.6, 13.5 Hz), 1.44 (s, 9H).

Step D: (3R)-3-[(tert-Butoxycarbonyl)amino]-4-[2-fluoro-4-(trifluoromethyl)-phenyl]-butanoic acid To a solution of 3.4 g (9.7 mmol) of the product from Step C in 60 mL of tetrahydrofuran at 0° C. were added sequentially 2.3 mL (13 mmol) of N,N-diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane:ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of N,N-diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate solution, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% hydrochloric acid and extracted with ethyl acetate. The combined organic phases were washed with brine, dried over magnesium sulfate and concentrated in vacuo to give 410 mg of the title compound as a white foamy solid.

$^1$H NMR (500 MHz, CD$_3$OD): δ 7.47-7.33 (m, 3H), 4.88 (bs, 1H), 4.26-3.98 (m, 1H), 3.06-3.01 (m, 1H), 2.83-2.77 (m, 1H), 2.58-2.50 (m, 2H), 1.29 (s, 9H).

INTERMEDIATE 3

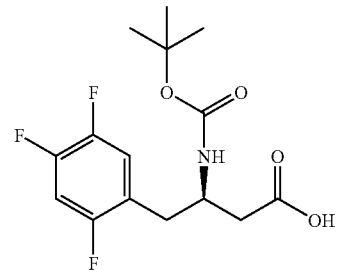

(3R)-3-[(tert-Butoxycarbonyl)amino]-4-(2,4,5-trifluorophenyl)butanoic acid

Step A: (2S,5R)-2,5-Dihydro-3,6-dimethoxy-2-isopropyl-5-(2',4',5'trifluorobenzyl)-pyrazine The title compound (3.81 g) was prepared from 3.42 g (18.5 mmol) of (2S)-2,5-dihydro-3,6-dimethoxy-2-isopropylpyrazine and 5 g (22.3 mmol) of 2,4,5-trifluorobenzyl bromide using the procedure described for Intermediate 2, Step A.

$^1$H NMR (500 MHz, CDCl$_3$): δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B: (R)-N-(tert-Butoxycarbonyl)-2,4,5-trifluorophenylalanine methyl ester

To a solution of 3.81 g (11.6 mmol) of (2S,5R)-2,5-dihydro-3,6-dimethoxy-2-isopropyl-5-(2',4',5'trifluorobenzyl)pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford 2.41 g of the title compound.

$^1$H NMR (500 MHz, CDCl$_3$): δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

The title compound (2.01 g) was prepared from 2.41 g (7.5 mmol) of (R)-N-(tert-butoxycarbonyl)-2,4,5-trifluorophenylalanine methyl ester using the procedure described for Intermediate 2, Step C.

LC/MS 220.9 (M+1-BOC).

Step D: (3R)-3-[(tert-Butoxycarbonyl)amino]-4-(2,4,5-trifluorophenyl)-butanoic acid To a solution of 0.37 g (1.16 mmol) of (R)-N-(1,1-dimethylethoxy-carbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane:water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded 401 mg of the title compound.

$^1$H NMR (500 MHz, CDCl$_3$): δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

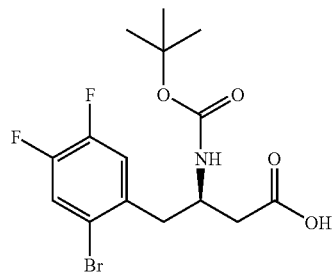

(3R)-4-(2-Bromo-4,5-difluorophenyl)-3-[(tert-butoxycarbonyl)amino]-butanoic acid To a solution of 2.4 g (10 mmol) of 2-bromo-4,5-difluorobenzoic acid [prepared according to the procedure of Braish et al., *Syn. Comm.*, 3067-3074 (1992)] in 75 mL of tetrahydrofuran was added 2.43 g (15 mmol) of carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2.9 g of 2-bromo-4,5-difluorobenzyl bromide contaminated with carbon tetrabromide which was used without further purification. Using the procedures outlined for the preparation of Intermediates 2-4, the benzyl bromide derivative was converted to the title compound.

LC/MS 394 and 396 (M+1).

Essentially following the procedures outlined for the preparation of Intermediates 1-4, the Intermediates in Table 1 were prepared.

TABLE 1

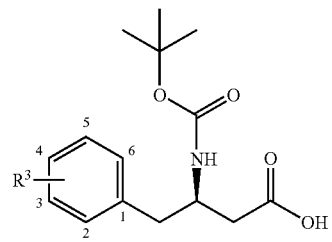

| Intermediate | R$^3$ | Selected $^1$H NMR data (CD$_3$OD) |
|---|---|---|
| 5 | 2-F, 4-Cl, 5-F | 7.11(dd, 1H, J=8.9, 6.4Hz), 7.03(dd, 1H, J=9.0, 6.6) |
| 6 | 2-F, 5-Cl | 7.27(dd, 1H, J=6.4, 2.5Hz), 7.21(m, 1H), 7.03(t, 1H, J=9.2Hz) |
| 7 | 2-Me, 5-Cl | 7.16(d, 1H, J=1.8Hz), 7.11-7.07(m, 2H), 2.34(s, 3H) |
| 8 | 2-Cl, 5-Cl | 7.34(d, 1H, J=9.0), 7.33(d, 1H, J=2.1Hz), 7.21(dd, 1H, J=8.5, 2.5Hz) |
| 9 | 2-F, 3-Cl, 6-F | 7.35(td, 1H, J=8.5, 5.8Hz), 6.95(t, 1H, J=8.5Hz) |
| 10 | 3-Cl, 4-F | 7.33(d, 1H, J=6.9Hz), 7.19-7.11(m, 2H) |
| 11 | 2-F, 3-F, 6-F | 7.18-7.12(m, 1H), 6.91(m, 1H) |
| 12 | 2-F, 4-F, 6-F | 6.81(t, 2H, J=8.4Hz) |
| 13 | 2-OCH$_2$Ph, 5-F | 7.49(d, 2H, J=7.6Hz), 7.38(t, 2H, J=7.3Hz), 7.30(t, 1H, J=7.3Hz), 6.96-6.89(m, 3H), 5.11(d, 1H, J=11.7Hz), 5.08(d, 1H, J=11.9Hz) |

PIPERIDINE INTERMEDIATE 14

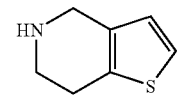

4,5,6,7-Tetrahydrothieno[3,2-c]pyridine, hydrochloride

This compound was prepared by a previously described route (S. Gronowitz and E. Sandberg, *Arkiv. foer Kemi*, 1970, 32, 217).

PIPERIDINE INTERMEDIATE 15

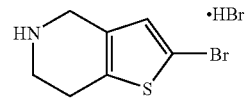

2-Bromo-4,5,6,7-tetrahydrothieno[3,2-c]pyridine, hydrobromide

Step A: N-(tert-Butoxycarbonyl)-4,5,6,7-tetrahydrothieno[3,2-c]pyridine

A suspension of 4,5,6,7-tetrahydrothieno[3,2-c]pyridine hydrochloride in 150 mL of dichloromethane was treated sequentially with triethylamine (11.70 mL, 84 mmol) and di-tert-butyl dicarbonate (10.1 g, 46 mmol). The resultant solution was allowed to stir at room temperature for 5 h. The solvent was removed under reduced pressure, and the residue was dissolved in 500 mL of ethyl acetate. The solution was washed sequentially with water (75 mL), 10% aqueous potassium hydrogen sulfate solution (75 mL), saturated aqueous sodium bicarbonate solution (75 mL) and saturated brine (75 mL), dried over sodium sulfate and concentrated under reduced pressure to afford the title compound as a viscous oil which crystallized on standing.

Step B: 2-Bromo-4,5,6,7-tetrahydrothieno[3,2-c]pyridine, hydrobromide

To a stirred, ice-cold solution of the product (9.57 g, 40 mmol) from Step A above in 150 mL of chloroform was added bromine (2.1 mL, 40 mmol) dropwise. The resultant cloudy mixture was allowed to warm to room temperature overnight. The precipitated solid was filtered, washed with ether, and dried in vacuo to afford the title compound as an off-white powder.

PIPERIDINE INTERMEDIATE 16

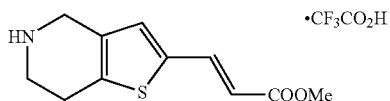

Methyl (2E)-3-(4,5,6,7-Tetrahydrothieno[3,2-c]pyridin-2-yl)prop-2-enoate, trifluoroacetic acid salt Step A: N-(tert-Butoxycarbonyl)-2-bromo-4,5,6,7-tetrahydrothieno[3,2-c]pyridine An ice-cold suspension of the product (6.1 g, 23 mmol) from piperidine intermediate 15, Step B in 150 mL of chloroform was treated sequentially with triethylamine (6.4 mL, 46 mmol) and di-tert-butyl dicarbonate (5.0 g, 23 mmol). The resultant solution was allowed to warm to room temperature and, after 18 h, the solvent was removed under reduced pressure. The residue was partitioned between 150 mL of ethyl acetate and 100 mL of water, and the aqueous layer was further extracted with additional ethyl acetate. The combined organic extracts were washed sequentially three times with 10% aqueous potassium bisulfate solution (75 mL) and once with saturated brine (75 mL), dried over sodium sulfate and concentrated under reduced pressure to afford the title compound as a pale yellow solid.

Step B: Methyl N-(tert-butoxycarbonyl)-(2E)-3-(4,5,6,7)-tetrahydrothieno[3,2-c]pyridin-2-yl)prop-2-enoate A mixture of the compound (3.18 g, 10 mmol) from Step A above, methyl acrylate (4.30 g, 50 mmol), palladium (II) acetate (0.224 g, 1.0 mmol), tri-o-tolylphosphine (1.83 g, 6 mmol) and triethylamine (2.8 mL, 20 mmol) in 15 mL of anhydrous acetonitrile was warmed at 90° C. in a resealable glass tube for 20 h. The reaction mixture was cooled to room temperature, diluted with 300 mL of ethyl acetate, filtered to remove the insoluble material, washed sequentially with two portions of 10% aqueous potassium bisulfate solution and one portion of saturated brine, dried over sodium sulfate and concentrated under reduced pressure. The resultant yellow solid was purified by flash chromatography (silica gel, 15% ethyl acetate/hexanes) to afford the title compound as a pale yellow solid.

Step C: Methyl (2E)-3-(4,5,6,7-Tetrahydrothieno[3,2-c]pyridin-2-yl)prop-2-enoate trifluoroacetic acid salt To a solution of the product (100 mg) from Step B above in 1.5 mL of dichloromethane was added 0.5 mL of trifluoroacetic acid. The solution was kept at room temperature for 1 h and was then concentrated under a stream of nitrogen and dried in vacuo to afford the title compound.

PIPERIDINE INTERMEDIATE 17

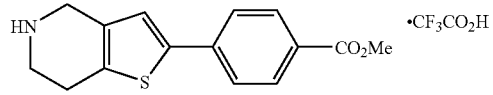

Methyl 4-(4,5,6,7-Tetrahydrothieno[3,2-c]pyridin-2-yl)benzoate, trifluoroacetic acid salt Step A: N-(t-butoxycarbonyl)-4-(4,5,6,7-Tetrahydrothieno[3,2-c]pyridin-2-yl)benzoic acid To a solution of the product (3.18 g, 10 mmol) from PIPERIDINE INTERMEDIATE 16, Step A in 100 mL of 1,4-dioxane was added sequentially para-carboxyphenylboronic acid (1.66 g, 10 mmol), 0.3M aqueous sodium carbonate solution (100 mL), and palladium(II) acetate (0.20 g), and the reaction mixture was stirred at room temperature for 7 h. The volatiles were removed under reduced pressure, and the resultant aqueous mixture was diluted with an additional 50 mL of water and filtered through a pad of Celite. The filtrate was acidified with 10% aqueous potassium bisulfate solution, and the mixture was extracted three times with ethyl acetate (150 mL). The combined organic extracts were washed with saturated brine, dried over sodium sulfate, and concentrated to afford a dark oil, which was purified by flash chromatography (silica gel, 97:2:1 chloroform/methanol/acetic acid eluant). The resultant tan, sticky solid was triturated with hexanes (50 mL) and ether (15 mL), and the precipitate was collected and dried in vacuo to afford the title compound as a beige powder.

Step B: Methyl 4-(4,5,6,7-Tetrahydrothieno[3,2-c]pyridin-2-yl)benzoate, trifluoroacetic acid salt To 0.100 g of the product from Step A above was added 1.0 mL each of methanol and dichloromethane. Trimethylsilyldiazomethane (2.0M in hexanes, 0.28 mL, 0.56 mmol) was added dropwise and the yellow solution was allowed to stir for 2 h at room temperature. Acetic acid (3 drops) was added, and the solution was then diluted with toluene and concentrated under reduced pressure. The residue was dissolved in 1.5 mL of dichloromethane and treated with 0.5 mL of trifluoroacetic acid. After 1 h, the solution was concentrated under a stream of nitrogen and dried in vacuo to afford the title compound.

PIPERIDINE INTERMEDIATE 18

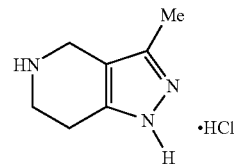

3-Methyl-4,5,6,7-tetrahydro-1H-pyrazolo[4,3-c]pyridine, hydrochloride

Step A: tert-Butyl 4-[(trimethylsilyl)oxy]-3,6-dihydropyridine-1-(2H)-carboxylate A dried flask was purged with nitrogen and charged with 23 mL (23 mmol) of 1M lithium bis(trimethylsilyl)amide in tetrahydrofuran and an additional 72 mL of anhydrous tetrahydrofuran. The solution was stirred under nitrogen at −78° C. as a solution of 4.0 g (20 mmol) of commercially available tert-butyl 4-oxopiperidine-1-carboxylate in 43 mL of anhydrous tetrahydrofuran was added gradually over 40 min. After completion of the addition, the mixture was stirred at −78° C. for 30 min. Then 3.6 mL (3.08 g, 28.4 mmol) of chlorotrimethylsilane was added. After being stirred at −78° C. for 15 min, the reaction mixture was rapidly warmed to room temperature. After a further 15 min, the solvent was removed by concentration in vacuo. The residue was partitioned between hexanes and a 2:1 mixture of saturated aqueous sodium carbonate solution and water. The aqueous phase was extracted with an additional portion of hexanes. The combined organic fractions were washed twice with brine and then dried over sodium sulfate. The filtered solution was concentrated in vacuo to yield the title compound, suitable for use without further purification. [For an alternative preparation, see Castro et al., *J. Med. Chem.*, 41, 2667-2670 (1998).]

$^1$H NMR (500 MHz, CDCl$_3$) δ 4.82 (br apparent s, 1H), 3.90 (br apparent s, 2H), 3.56 (br apparent s, 2H), 2.14 (br apparent s, 2H), 1.50 (s, 9H), 0.23 (s, 9H).

Step B: tert-Butyl 3-acetyl-4-oxopiperidine-1-carboxylate

A dried flask was purged with nitrogen and charged with 2.64 mL of 1.4M methyllithium in diethyl ether. Without exposure to air, the diethyl ether was removed by evaporation in vacuo and replaced by 10 mL of anhydrous tetrahydrofuran. The resultant solution was stirred at −15° C. and treated dropwise over 10 min with a solution of 1.00 g (3.68 mmol) of tert-butyl 4-[(trimethylsilyl)oxy]-3,6-dihydropyridine-1-(2H)-carboxylate from Step A in 10 mL of anhydrous tetrahydrofuran. After being stirred at −15° C. for 40 min, the reaction mixture was cooled to −78° C. and then slowly transferred via cannula to a solution of 0.265 mL (293 mg, 3.73 mmol) of acetyl chloride in 16 mL of anhydrous tetrahydrofuran, which had been pre-cooled to −78° C. The reaction mixture was stirred at this temperature for 3 h and then quenched with saturated aqueous ammonium chloride solution. The mixture was extracted with two portions of ethyl acetate. The combined organic fractions were dried over sodium sulfate, filtered, and concentrated in vacuo. Purification of the residue by flash chromatography (silica gel, 10-30% ethyl acetate/hexanes) provided the title compound, which exists as a mixture of keto and enol tautomers.

$^1$H NMR (500 MHz, CDCl$_3$) δ 5.4 (br s, <1H), 4.22 (br apparent s, 1H), 4.01 (br apparent s, 1H), 3.62 (br apparent t, J=6 Hz, 2H), 2.48 (br apparent t, J=5.6 Hz, 1H), 2.31 (br m, 1H), 2.17 (s, 3H), 1.52, 1.51 (overlapping s, total 9H). LC/MS 264 (M+Na).

Step C: tert-Butyl 3-methyl-1,4,6,7-tetrahydro-5H-pyrazolo[4,3-c]pyridine-5-carboxylate A mixture of 100 mg (0.414 mmol) of tert-butyl 3-acetyl-4-oxopiperidine-1-carboxylate from Step B, 0.0246 mL (25.4 mg, 0.497 mmol) of 98% hydrazine monohydrate, and 1.5 mL of ethanol was stirred at reflux temperature for 1 h. The cooled solution was partitioned between dichloromethane and water. The aqueous phase was extracted with dichloromethane. The combined organic fractions were dried over sodium sulfate, filtered, and concentrated in vacuo. Purification of the residue by flash chromatography (silica gel, 20-90% ethyl acetate/hexanes) afforded the title compound.

$^1$H NMR (500 MHz, CDCl$_3$) δ 4.41 (br s, 2M), 3.73 (br m, 2H), 2.78 (br m, 2H), 2.27 (s, 3H), 1.53 (s, 9H). LC/MS 238 (M+1).

Step D: 3-Methyl-4,5,6,7-tetrahydro-1H-pyrazolo[4,3-c]pyridine, hydrochloride tert-Butyl 3-methyl-1,4,6,7-tetrahydro-5H-pyrazolo[4,3-c]pyridine-5-carboxylate (53 mg, 0.22 mmol) from Step C was treated with 2 mL of 4M hydrogen chloride in anhydrous dioxane. The mixture was stirred under nitrogen at room temperature for 45 min. The product was precipitated by addition of diethyl ether. The solid was collected on a filter and washed sequentially with diethyl ether and petroleum ether to yield the title compound as a hydrochloride salt.

$^1$H NR (500 MHz, CDCl$_3$+some CD$_3$OD) δ 3.41 (br apparent s, 2H), 3.23 (s, 2H), 3.06 (br apparent s, 2H), 2.25 (s, 3H). LC/MS 138 (M+1).

PIPERIDINE INTERMEDIATE 19

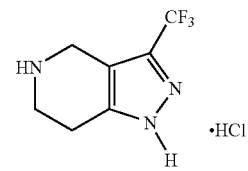

3-(Trifluoromethyl)-4,5,6,7-tetrahydro-1H-pyrazolo[4,3-c]pyridine, hydrochloride Step A: tert-Butyl 4-oxo-3-(trifluoroacetyl)piperidine-1-carboxylate Essentially following the procedure used for PIPERIDINE INTERMEDIATE 18, Step B, tert-butyl 4-[(trimethylsilyl)oxy]-3,6-dihydropyridine-1-(2H)-carboxylate from PIPERIDINE INTERMEDIATE 18, Step A, was reacted with trifluoroacetic anhydride to yield the title compound.

$^1$H NMR (500 MHz, CDCl$_3$) δ 4.40 (br apparent s, 2H), 3.68 (apparent t, J=6 Hz, 2H), 2.64 (br apparent t, J=6 Hz, 2H), 1.52 (s, 9H).

Step B: tert-Butyl 3-(trifluoromethyl)-1,4,6,7-tetrahydro-5H-pyrazolo[4,3-c]pyridine-5-carboxylate Essentially following the procedure used for PIPERIDINE INTERMEDIATE 18, Step C, tert-butyl 4-oxo-3-(trifluoroacetyl)piperidine-1-carboxylate from Step A above was reacted with hydrazine monohydrate to give, after work-up, a mixture of the title compound and the deprotected product. This mixture was used directly, without purification, in the next step.

Step C: 3-Methyl-4,5,6,7-tetrahydro-1H-pyrazolo[4,3-c]pyridine, hydrochloride

Essentially following the procedure used for PIPERIDINE INTERMEDIATE 18, Step D, crude tert-butyl 3-(trifluoromethyl)-1,4,6,7-tetrahydro-5H-pyrazolo[4,3-c]pyridine-5-carboxylate from Step B above was deprotected with 4M hydrogen chloride in anhydrous dioxane to afford the title compound as a hydrochloride salt.

$^1$H NMR (500 MHz, CDCl$_3$+some CD$_3$OD): δ 3.76 (br m, 2H), 3.63 (m, 2H), 3.40 (br m, 2H). LC/MS 192 (M+1).

PIPERIDINE INTERMEDIATE 20

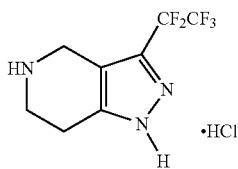

3-(Pentafluoroethyl)-4,5,6,7-tetrahydro-1H-pyrazolo[4,3-c]pyridine, hydrochloride Step A: tert-Butyl 4-oxo-3-(2,2,3,3,3-pentafluoropropanoyl)piperidine-1-carboxylate Essentially following the procedure used for PIPERIDINE INTERMEDIATE 18, Step B, tert-butyl 4-[(trimethylsilyl)oxy]-3,6-dihydropyridine-1-(2H)-carboxylate from PIPERIDINE INTERMEDIATE 18, Step A, was reacted with pentafluoropropionic anhydride to yield the title compound.

$^1$H NMR (500 MHz, CDCl$_3$) δ 4.44 (br apparent s, 2H), 3.67 (apparent t, J=6 Hz, 2H), 2.66 (br apparent t, J=5.9 Hz, 2H), 1.51 (s, 9H). LC/MS 246 (M+1-Boc).

Step B: tert-Butyl 3-(pentafluoroethyl)-1,4,6,7-tetrahydro-5H-pyrazolo[4,3-c]pyridine-5-carboxylate Essentially following the procedure used for PIPERIDINE INTERMEDIATE 18, Step C, tert-butyl 4-oxo-3-(2,2,3,3,3-pentafluoropropanoyl)piperidine-1-carboxylate from Step A above was reacted with hydrazine monohydrate to give the title compound. The crude product was used directly, without purification, in the next step.

Step C: 3-(Pentafluoroethyl)-4,5,6,7-tetrahydro-1H-pyrazolo[4,3-c]pyridine

Essentially following the procedure used for PIPERIDINE INTERMEDIATE 18, Step D, crude tert-butyl 3-(2,2,3,3,3-pentafluoropropanoyl)-1,4,6,7-tetrahydro-5H-pyrazolo[4,3-c]pyridine-5-carboxylate from Step B above was deprotected with 4M hydrogen chloride in anhydrous dioxane to afford the title compound as a hydrochloride salt.

$^1$H NMR (500 MHz, CD$_3$OD) δ 4.35 (s, 2H), 3.59 (t, J=6 Hz, 2H), 3.14 (t, J=6 Hz, 2H). LC/MS 242 (M+1).

PIPERIDINE INTERMEDIATE 21

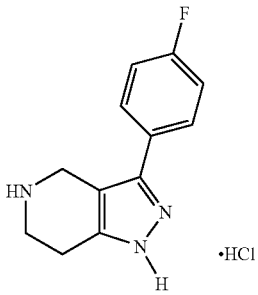

3-(4-Fluorophenyl)-4,5,6,7-tetrahydro-1H-pyrazolo[4,3-c]pyridine, hydrochloride

Step A: tert-Butyl 3-(4-fluorobenzoyl)-4-oxopiperidine-1-carboxylate

Essentially following the procedure used for PIPERIDINE INTERMEDIATE 18, Step B, tert-butyl 4-[(trimethylsilyl)oxy]-3,6-dihydropyridine-1-(2H)-carboxylate from PIPERIDINE INTERMEDIATE 18, Step A, was reacted with 4-fluorobenzoyl chloride to yield the title compound.

$^1$H NMR (500 MHz, CDCl$_3$) δ 7.95 (br m, 1H), 7.57 (m, 1H), 7.16 (m, 2H), 4.30 (s, 2H), 3.68 (apparent t, J=6 Hz, 2H), 2.63 (m, 2H), 1.45 (s, 9H). LC/MS 222 (M+1-Boc).

Step B: tert-Butyl 3-(4-fluorophenyl)-1,4,6,7-tetrahydro-5H-pyrazolo[4,3-c]pyridine-5-carboxylate Essentially following the procedure used for PIPERIDINE INTERMEDIATE 18, Step C, tert-butyl 3-(4-fluorobenzoyl)-4-oxopiperidine-1-carboxylate from Step A above was reacted with hydrazine monohydrate to give the title compound. The crude product was used directly, without purification, in the next step.

Step C: 3-(4-Fluorophenyl)-4,5,6,7-tetrahydro-1H-pyrazolo[4,3-c]pyridine, hydrochloride Essentially following the procedure used for PIPERIDINE INTERMEDIATE 18, Step D, crude tert-butyl 3-(4-fluorophenyl)-1,4,6,7-tetrahydro-5H-pyrazolo[4,3-c]pyridine-5-carboxylate from Step B above was deprotected with 4M hydrogen chloride in anhydrous dioxane to afford the title compound as a hydrochloride salt.

$^1$H NMR (500 MHz, CD$_3$OD) δ 7.62 J(m, 2H), 7.27 (m, 2H), 4.47 (s, 2H), 3.62 (t, J=6 Hz, 2H), 3.14 (t, J=6 Hz, 2H). LC/MS 218 (M+1).

PIPERIDINE INTERMEDIATE 22

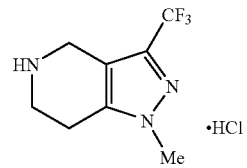

1-Methyl-3-(trifluoromethyl)-4,5,6,7-tetrahydro-1H-pyrazolo[4,3-c]pyridine hydrochloride Step A: tert-Butyl 1-methyl-3-(trifluoromethyl)-1,4,6,7-tetrahydro-5H-pyrazolo[4,3-c]pyridine-5-carboxylate A mixture of 150 mg (0.508 mmol) of tert-butyl 4-oxo-3-(trifluoroacetyl)piperidine-1-carboxylate from PIPERIDINE INTERMEDIATE 19, Step B, 0.033 mL (28.6 mg, 0.608 mmol) of 98% methylhydrazine, and 2 mL of absolute ethanol was stirred at reflux temperature 4 h. The solution was partitioned between ethyl acetate and half-saturated aqueous sodium chloride solution. The aqueous phase was extracted with ethyl acetate. The combined organic fractions were dried over sodium sulfate, filtered, and concentrated in vacuo. Purification of the residue by flash chromatography (silica gel, 7:3 hexane/ethyl acetate) afforded the title compound, the regiochemistry of which was confirmed by nuclear Overhauser effect between the 1-methyl group and the adjacent ring protons at the 7-position.

$^1$H NMR (500 MHz, CDCl$_3$) δ 4.53 (br apparent s, 2H), 3.84 (s, 3H), 3.77 (br apparent s, 2H), 2.73 (br apparent t, J=5.4 Hz, 2H), 1.53 (s, 9H). LC/MS 306 (M+1).

Step B: 1-Methyl-3-(trifluoromethyl)-4,5,6,7-tetrahydro-1H-pyrazolo[4,3-c]pyridine, hydrochloride Essentially following the procedure for PIPERIDINE INTERMEDIATE 18, Step D, tert-butyl 1-methyl-3-(trifluoromethyl)-1,4,6,7-tetrahydro-5H-pyrazolo[4,3-c]pyridine-5-carboxylate from Step A above was deprotected with 4M hydrogen chloride in anhydrous dioxane to afford the title compound as a hydrochloride salt. LC/MS 206 (M+1). This material was used directly in the coupling reaction with Intermediates 1-13 without further purification.

PIPERIDINE INTERMEDIATE 23

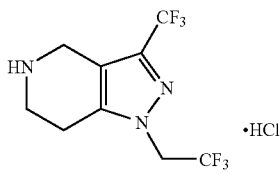

1-(2,2,2-Trifluoroethyl)-3-(trifluoromethyl)-4,5,6,7-tetrahydro-1H-pyrazolo[4,3-c]pyridine, hydrochloride Step A: tert-Butyl 1-(2,2,2-trifluoroethyl)-3-(trifluoromethyl)-1,4,6,7-tetrahydro-5H-pyrazolo[4,3-c]pyridine-5-carboxylate A mixture of 200 mg (0.677 mmol) of tert-butyl 4-oxo-3-(trifluoroacetyl)piperidine-1-carboxylate from PIPERIDINE INTERMEDIATE 19, Step B, 0.103 mL (133 mg, 0.818 mmol) of (2,2,2-trifluoroethyl)hydrazine (70% w/w solution in water), and 3 mL of absolute ethanol was stirred at reflux overnight. Because the reaction was incomplete, the ethanol was removed by evaporation in vacuo and replaced with 2-methoxyethanol. The resultant solution was stirred at reflux for an additional day. The solution was concentrated in vacuo, and the residue was purified by flash chromatography (silica gel, 10-40% ethyl acetate/hexanes) to yield the title compound. The regiochemistry was assigned in analogy to the product from PIPERIDINE INTERMEDIATE 22, Step A, on the basis of NMR and TLC evidence.

$^1$H NMR (500 MHz, CDCl$_3$) δ 4.68 (q, J=8 Hz), 4.55 (br apparent s, 2H), 3.79 (br apparent s, 2H), 2.77 (br m, 2H), 1.53 (s, 9H). LC/MS 374 (M+1).

Step B: 1-(2,2,2-Trifluoroethyl)-3-(trifluoromethyl)-4,5,6,7-tetrahydro-1H-pyrazolo[4,3-c]pyridine, hydrochloride Essentially following the procedure for PIPERIDINE INTERMEDIATE 18, Step D, tert-butyl 1-(2,2,2-trifluoroethyl)-3-(trifluoromethyl)-1,4,6,7-tetrahydro-5H-pyrazolo[4,3-c]pyridine-5-carboxylate from Step A above was deprotected with 4M hydrogen chloride in anhydrous dioxane to afford the title compound as a hydrochloride salt. LC/MS 274 (M+1). This material was used directly in the coupling reaction with Intermediates 1-13 without further purification.

PIPERIDINE INTERMEDIATE 24

3-(Trifluoromethyl)-4,5,6,7-tetrahydro-1H-pyrazolo[3,4-c]pyridine, hydrochloride Step A: tert-Butyl 5-[(trimethylsilyl)oxy]-3,6-dihydropyridine-1-(2H)-carboxylate Commercially available tert-butyl 4-oxopiperidine-1-carboxylate was deprotonated with lithium bis(trimethylsilyl) amide, reacted with chlorotrimethylsilane, and worked up according to the procedure used for PIPERIDINE INTERMEDIATE 18, Step A to give a mixture of the title compound and its isomer, tert-butyl 5-[(trimethylsilyl)oxy]-3,4-dihydropyridine-1-(2H)-carboxylate. This mixture was used directly in the next step without purification.

$^1$H NMR (500 MHz, CDCl$_3$; peaks attributable to title compound) δ 5.0 (br apparent s, 1H), 3.76 (br apparent s, 2H), 3.45 (br apparent s, 2H), 2.15 (br apparent s, 2H), 1.51 (s, 9H), 0.22 (s, 9H). LC/MS 172 (M+1-Boc).

Step B: tert-Butyl 3-oxo-4-(trifluoroacetyl)piperidine-1-carboxylate

Essentially following the procedure for PIPERIDINE INTERMEDIATE 18, Step B, crude tert-butyl 5-[(trimethylsilyl)oxy]-3,6-dihydropyridine-1-(2H)-carboxylate from Step A was reacted with trifluoroacetic anhydride. Purification by flash chromatography (10-90% ethyl acetate/hexanes) yielded the title compound.

$^1$H NMR (500 MHz, CDCl$_3$) δ 4.29 (br apparent s, 2H), 3.63 (br apparent t, J=5.6 Hz, 2H), 2.64 (br m, 2H), 1.54 (s, 9H). LC/MS 196 (M+1-Boc).

Step C: tert-Butyl 3-(trifluoromethyl)-1,4,5,7-tetrahydro-6H-pyrazolo[3,4-c]pyridine-6-carboxylate Essentially following the procedure for PIPERIDINE INTERMEDIATE 18, Step C, tert-butyl 3-oxo-4-(trifluoroacetyl)piperidine-1-carboxylate from Step B above was reacted with hydrazine monohydrate, except that heating at reflux temperature was continued overnight. Purification of the residue by successive flash chromatography (first column: silica gel, 0-2% methanol and 0-0.2% ammonium hydroxide in dichloromethane; second column: silica gel, 30-50% ethyl acetate/hexanes) gave the title compound.

$^1$H NMR (500 MHz, CDCl$_3$) δ 4.68 (s, 2H), 3.74 (br apparent s, 2H), 2.78 (br apparent s, 2H), 1.56 (s, 9H). LC/MS 236 (M+1-isobutene).

Step D: 3-(Trifluoromethyl)-4,5,6,7-tetrahydro-1H-pyrazolo[3,4-c]pyridine, hydrochloride Essentially following the procedure for PIPERIDINE INTERMEDIATE 18, Step D, crude tert-butyl 3-(trifluoromethyl)-1,4,6,7-tetrahydro-5H-pyrazolo[4,3-c]pyridine-5-carboxylate from Step B above was deprotected with 4M hydrogen chloride in anhydrous dioxane to afford the title compound as a hydrochloride salt. This material was used directly in the coupling reaction with Intermediates 1-13 without further purification.

PIPERIDINE INTERMEDIATE 25

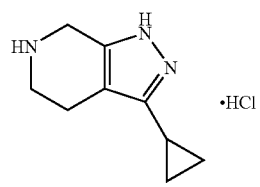

3-Cyclopropyl-4,5,6,7-tetrahydro-1H-pyrazolo[3,4-c]pyridine, hydrochloride

Step A: tert-Butyl 4-(cyclopropylcarbonyl)-3-oxopiperidine-1-carboxylate

Essentially following the procedure for PIPERIDINE INTERMEDIATE 18, Step B, crude tert-butyl 5-[(trimethylsilyl)oxy]-3,6-dihydropyridine-1-(2H)-carboxylate from PIPERIDINE INTERMEDIATE 24, Step A, was reacted with cyclopropanecarbonyl chloride to yield the title compound, which could not be separated from its isomer, tert-butyl 2-(cyclopropylcarbonyl)-3-oxopiperidine-1-carboxylate.

$^1$H NMR (500 MHz, CDCl$_3$; peaks attributable to the title compound) δ 4.15 (br apparent s, 2H), 3.63 (br m, 2H), 2.63 (br m, 2H), 2.29 (m, 1H), 1.52 (s, 9H), 1.2-0.8 (complex m, 4H). LC/MS 212 (M+1-isobutene).

Step B: tert-Butyl 3-cyclopropyl-1,4,5,7-tetrahydro-6H-pyrazolo[3,4-c]pyridine-6-carboxylate Essentially following the procedure for PIPERIDINE INTERMEDIATE 18, Step C, crude tert-butyl 4-(cyclopropylcarbonyl)-3-oxopiperidine-1-carboxylate from Step A above was reacted with hydrazine monohydrate to give the title compound, which was purified by preparative HPLC (YMC Pro-C18 column, gradient elution, 20-45% acetonitrile/water).

$^1$H NMR (500 MHz, CDCl$_3$) δ 4.74 (s, 2H), 3.77 (br apparent s, 2H), 2.71 (br apparent s, 2H), 1.98 (m, 1H), 1.54 (s, 9H), 1.24 (m, 2H), 1.09 (m, 2H). LC/MS 208 (M+1-isobutene).

Step C: 3-(Trifluoromethyl)-4,5,6,7-tetrahydro-1H-pyrazolo[3,4-c]pyridine, hydrochloride Essentially following the procedure for PIPERIDINE INTERMEDIATE 18, Step D, tert-butyl 3-cyclopropyl-1,4,6,7-tetrahydro-6H-pyrazolo[3,4-c]pyridine-6-carboxylate from Step B above was deprotected with 4M hydrogen chloride in anhydrous dioxane to afford the title compound as a hydrochloride salt. LC/MS 164 (M+1). This material was used directly in the coupling reaction with Intermediates 1-13 without further purification.

PIPERIDINE INTERMEDIATE 26

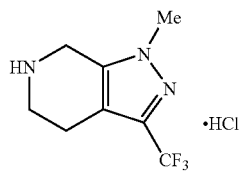

1-Methyl-3-(trifluoromethyl)-4,5,6,7-tetrahydro-1H-pyrazolo[3,4-c]pyridine, hydrochloride Step A: tert-Butyl 1-methyl-3-(trifluoromethyl)-1,4,5,7-tetrahydro-6H-pyrazolo[4,3-c]pyridine-6-carboxylate Essentially following the procedure for PIPERIDINE INTERMEDIATE 22, Step A, tert-butyl 3-oxo-4-(trifluoroacetyl)piperidine-1-carboxylate from PIPERIDINE INTERMEDIATE 24, Step B, was reacted with methylhydrazine to afford the title compound. The regiochemistry was assigned by analogy to the product from PIPERIDINE INTERMEDIATE 22, Step A, on the basis of NMR and TLC evidence.

$^1$H NMR (500 MHz, CDCl$_3$) δ 4.56 (br apparent s, 2H), 3.84 (s, 3H), 3.67 (br apparent s, 2H), 2.72 (br apparent t, J=5 Hz, 2H), 1.54 (s, 9H). LC/MS 306 (M+1).

Step B: 1-Methyl-3-(trifluoromethyl)-4,5,6,7-tetrahydro-1H-pyrazolo[3,4-c]pyridine, hydrochloride Essentially following the procedure for PIPERIDINE INTERMEDIATE 18, Step D, tert-butyl 1-methyl-3-(trifluoromethyl)-1,4,5,7-tetrahydro-6H-pyrazolo[4,3-c]pyridine-6-carboxylate from Step A above was deprotected with 4M hydrogen chloride in anhydrous dioxane to afford the title compound as a hydrochloride salt. LC/MS 206 (M+1). This material was used directly in the coupling reaction with Intermediates 1-13 without further purification.

PIPERIDINE INTERMEDIATE 27

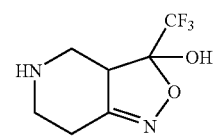

3-(Trifluoromethyl)-3,3a,4,5,6,7-hexahydroisoxazolo[4,3-c]pyridin-3-ol

Analogous to literature conditions for a related (but dehydrated) compound [Umada et al., *Synthesis*, 1457-1462 (1994)], a mixture of 80 mg (0.271 mmol) of tert-butyl 4-oxo-3-(trifluoroacetyl)-piperidine-1-carboxylate from PIPERIDINE INTERMEDIATE 19, Step B, 23.3 mg (0.335 mmol) of hydroxylamine hydrochloride, and 1.5 mL of glacial acetic acid was stirred at reflux for 3.5 h. Removal of the BOC protecting group accompanied ring closure. The cooled reaction mixture was partitioned between ethyl acetate and saturated sodium bicarbonate solution. The ethyl acetate phase was dried over sodium sulfate and concentrated to give some impure 3-(trifluoromethyl)-4,5,6,7-tetrahydroisoxazolo[4,3-c]pyridine. The aqueous phase was extracted several times with ethyl acetate containing some methanol. The combined organic fractions were washed with brine and then dried over sodium sulfate. Concentration of the filtered solution in vacuo afforded the title compound in satisfactory purity. In the next step, dehydration of the isoxazole ring was achieved along with acylation according to Procedure 1, Method E.

$^1$H NMR (500 MHz, CDCl$_3$ containing CD$_3$OD) δ 3.26-3.20 (complex m, 2H), 3.14 (m, 1H), 2.87 (m, 1H), 2.65 (m, 1H), 2.44 (m, 1H), 2.22 (m, 1H). LC/MS 211 (M+1).

PIPERIDINE INTERMEDIATE 28

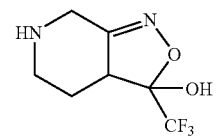

3-(Trifluoromethyl)-3,3a,4,5,6,7-hexahydroisoxazolo[3,4-c]pyridin-3-ol

Essentially following the procedure for PIPERIDINE INTERMEDIATE 27, tert-butyl 3-oxo-4-(trifluoroacetyl)-piperidine-1-carboxylate from PIPERIDINE INTERMEDIATE 24, Step B, was reacted with hydroxylamine hydrochloride in glacial acetic acid (heating time 6 h). Removal of the BOC protecting group accompanied ring closure. The crude product was purified by flash chromatography (silica gel, 5-10% methanol and 0.5-1% ammonium hydroxide in dichloromethane). In the next step, dehydration of the isoxazole ring was achieved along with acylation according to Procedure 1, Method D.

$^1$H NMR (500 MHz, CD$_3$OD) δ 3.85 (d, J=15 Hz, 1H), 3.48 (m, 1H), 3.44 (d, J=15 Hz, 1H), 3.16 (m, 1H), 2.67 (m, 1H), 1.95 (m, 2H). LC/MS 211 (M+1). The regiochemistry was established by $^{19}$F NMR studies on the final β-aminoacyl amide product and also on a sample of amine precursor prepared using $^{15}$N-labeled hydroxylamine.

PIPERIDINE INTERMEDIATE 29

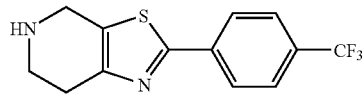

2-[4-(Trifluoromethyl)phenyl]-4,5,6,7-tetrahydro[1,3]thiazolo[5,4-c]pyridine

A mixture of 200 mg (0.773 mmol) of 3-bromopiperidin-4-one hydrobromide (prepared according to the procedure of Gangjee et al., *J. Med. Chem.*, 41, 1409-1416 (1998)), 180 mg (0.85 mmol) of commercially available 4-(trifluoromethyl)benzenecarbothioamide, and 1.6 mL of N,N-dimethylformamide was stirred at 100° C. for 4 h. The solvent was removed in vacuo, and the residue was purified by flash chromatography (silica gel, 95:5:0.5 dichloromethane/methanol/ammonium hydroxide) to yield the title compound.

$^1$H NMR (500 MHz, CD$_3$OD) δ 8.14 (d, J=8 Hz, 2H), 7.81 (d, J=8 Hz, 2H), 4.55 (m, 2H), 3.64 (m, 2H), 3.21 (m, 2H). LC/MS 285 (M+1).

PIPERIDINE INTERMEDIATE 30

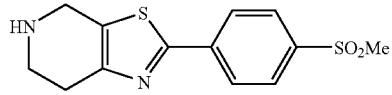

2-[4-(Methylsulfonyl)phenyl]-4,5,6,7-tetrahydro[1,3]thiazolo[5,4-c]pyridine

Step A: Benzyl 3-bromo-4-oxopiperidine-1-carboxylate

To a solution of 6.0 mL (7.13 g, 30.6 mmol) of commercially available benzyl 4-oxopiperidine-1-carboxylate in 60 mL of chloroform at 5° C. under nitrogen was gradually added 1.56 mL (4.89 g, 30.6 mmol) of bromine, and the solution was allowed to warm to room temperature. After 30 min, the solution was shaken with brine, and the aqueous phase was extracted with four portions of dichloromethane. The combined organic fractions were dried over magnesium sulfate, filtered, and concentrated in vacuo. The residue was purified by flash chromatography (silica gel, 10-20% ethyl acetate/hexanes) to give the title compound.

$^1$H NMR (500 MHz, CDCl$_3$) δ 7.37 (m, 5H), 5.22-5.13 (complex m, 3H), 4.6-3.2 (m, 6H).

Step B: Benzyl 2-[4-(methylthio)phenyl]-6,7-dihydro[1,3]thiazolo[5,4-c]pyridine-5(4H)-carboxylate A mixture of 520 mg (1.67 mmol) of benzyl 3-bromo-4-oxopiperidine-1-carboxylate from Step A, 459 mg (2.51 mmol) of 4-(methylthio)benzenecarbothioamide [prepared according to the procedure of Ohkawa et al., PCT Application WO 01/74811 (2001)], and approximately 2 mL of N,N-dimethylformamide was stirred at 100° C. for 2.5 h. The solvent was removed in vacuo, and the residue was partitioned between diethyl ether and aqueous sodium carbonate solution. The organic phase was dried over magnesium sulfate, filtered, and concentrated in vacuo. The residue was purified by flash chromatography (silica gel, 0-20% ethyl acetate in hexanes) to yield the title compound.

$^1$H NMR (500 MHz, CDCl$_3$): δ 7.83 (d, J=8 Hz, 2H), 7.42-7.37 (complex m, 5H), 7.30 (d, J=8 Hz, 2H), 5.23 (s, 2H), 4.78 (s, 2H), 3.90 (br apparent s, 2H), 2.99 (br apparent s, 2H), 2.55 (s, 3H). LC/MS 397 (M+1).

Step C: Benzyl 2-[4-(methylsulfonyl)phenyl]-6,7-dihydro[1,3]thiazolo[5,4-c]pyridine-5(4H)-carboxylate To a solution of 74 mg (0.187 mmol) of benzyl 2-[4-(methylthio)phenyl]-6,7-dihydro[1,3]thiazolo[5,4-c]pyridine-5(4H)-carboxylate from Step B in 1.5 mL of N,N-dimethylformamide was added 81 mg (0.468 mmol) of 3-chloroperoxybenzoic acid, and stirring was continued at room temperature. After 40 min, the mixture was partitioned between ethyl acetate and saturated sodium bicarbonate solution. The organic phase was dried over sodium sulfate, filtered, and concentrated in vacuo. Flash chromatography of the residue (silica gel, 99:1 dichloromethane:methanol) afforded the title compound.

$^1$H NMR (500 MHz, CDCl$_3$): δ 8.09 (d, J=8.5 Hz, 2H), 8.00 (d, J=8.5 Hz, 2H), 7.40 (m, 5H), 5.21 (s, 2H), 4.81 (s, 2H), 3.89 (br apparent s, 2H), 3.10 (s, 3H), 3.00 (br apparent s, 2H). LC/MS 429 (M+1).

Step D: 2-[4-(Methylsulfonyl)phenyl]-4,5,6,7-tetrahydro[1,3]thiazolo[5,4-c]pyridine A 59 mg (0.138 mmol) sample of benzyl 2-[4-(methylsulfonyl)phenyl]-6,7-dihydro[1,3]thiazolo[5,4-c]pyridine-5(4H)-carboxylate from Step C was treated with 2 mL of 30% hydrogen bromide in acetic acid, and the solution was stirred at room temperature. After 30 min, the solution was carefully partitioned between dichloromethane and saturated sodium carbonate solution. The organic phase was dried over sodium sulfate, filtered, and concentrated in vacuo. Purification of the residue by radial chromatography (silica gel, 3-10% methanol in dichloromethane) gave the title compound.

$^1$H NMR (500 MHz, CD$_3$OD): δ8.20 (d, J=8 Hz, 2H), 8.08 (d, J=8 Hz, 2H), 4.59 (s, 2H), 3.67 (m, 2H), 3.23 (m, 2H), 3.18 (s, 3H). LC/MS 295 (M+1).

PIPERIDINE INTERMEDIATE 31

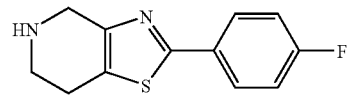

2-(4-Fluorophenyl)-4,5,6,7-tetrahydro[1,3]thiazolo[4,5-c]pyridine

Step A: 4-Bromo-3-oxopiperidine-1-carboxylate hydrobromide

To a solution of 4.00 g (20.1 mmol) of commercially available tert-butyl 3-oxopiperidine-1-carboxylate in 140 mL of chloroform vigorously stirred under nitrogen at 15° C. was added dropwise over 1 h 1.02 mL (3.21 g, 20.1 mmol) of bromine. During the addition, the red bromine color quickly dissipated, and precipitation occurred. The precipitate was collected on a filter, washed with dichloromethane, and dried to give the title compound, which was used without further purification.

Step B: 2-(4-Fluorophenyl)-4,5,6,7-tetrahydro[1,3]thiazolo[4,5-c]pyridine

A mixture of 315 mg (1.2 mmol) of crude 4-bromo-3-oxopiperidine-1-carboxylate hydrobromide from Step A, 283 mg (1.83 mmol) of 4-fluorobenzenecarbothioamide (prepared according to the procedure of Yu et al., U.S. Pat. No. 6,156,776 (2000)), and 6 mL of N,N-dimethylformamide was stirred at 100° C. for 2.5 h. The solvent was removed in vacuo, and the residue was partitioned between dichloromethane and aqueous sodium carbonate solution. The organic phase was dried over magnesium sulfate, filtered, and concentrated in vacuo. The residue was purified by flash chromatography (silica gel, 2-10% methanol and 0-1% ammonium hydroxide in dichloromethane) to yield the title compound.

$^1$H NMR (500 MHz, CD$_3$OD) δ 7.90 (m, 2H), 7.20 (apparent t, J=8.7 Hz, 2H), 3.98 (s, 2H), 3.13 (apparent t, J=5.7 Hz, 2H), 2.89 (m, 2H). LC/MS 235 (M+1).

PIPERIDINE INTERMEDIATE 32

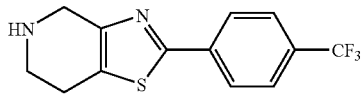

2-[4-(Trifluoromethyl)phenyl]4,5,6,7-tetrahydro[1,3]thiazolo[4,5-c]pyridine

Essentially following the procedure for PIPERIDINE INTERMEDIATE 31, Step B, crude 4-bromo-3-oxopiperidine-1-carboxylate hydrobromide from PIPERIDINE INTERMEDIATE 31, Step A, and commercially available 4-(trifluoromethyl)benzenecarbothioamide were reacted to give the title compound.

$^1$H NMR (500 MHz, CD$_3$OD) δ 8.08 (d, J=8 Hz, 2H), 7.77 (d, J=8 z, 2H), 4.06 (s, 2H), 3.19 (apparent t, J=5.7 Hz, 2H), 2.97 (m, 2H). LC/MS 285 (M+1).

PIPERIDINE INTERMEDIATE 33

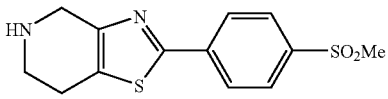

2-[4-(Methylsulfonyl)phenyl]4,5,6,7-tetrahydro[1,3]thiazolo[4,5-c]pyridine

Step A: 2-[4-(Methylthio)phenyl]-4,5,6,7-tetrahydro[1,3]thiazolo[4,5-c]pyridine

Essentially following the procedure for PIPERIDINE INTERMEDIATE 31, Step B, crude 4-bromo-3-oxopiperidine-1-carboxylate hydrobromide from PIPERIDINE INTERMEDIATE 31, Step A, and 4-(methylthio)benzenecarbothioamide (prepared according to the procedure of Ohkawa et al., WO 01/74811 (2001)) were reacted to give the title compound.

$^1$H NMR (500 MHz, CD$_3$OD) δ 7.79 (d, J=8.5 Hz, 2, 7.32 (d, J=8.5 Hz, 2, 3.97 (s, 2H), 3.13 (m, 2H), 2.89 (m, 21, 2.53 (s, 3H). LC/MS 263 (M+1).

Step B: Benzyl 2-[4-(methylthio)phenyl]-6,7-dihydro[1,3]thiazolo[4,5-c]pyridine-5(4H)-carboxylate A solution of 150 mg (0.572 mmol) of 2-[4-(methylthio)phenyl]4,5,6,7-tetrahydro[1,3]thiazolo[4,5-c]pyridine from Step A and 0.219 mL (162 mg, 1.25 mmol) of N,N-diisopropylethylamine in 6 mL of dichloromethane and 12 mL of tetrahydrofuran was stirred under nitrogen at −78° C. as 0.090 mL (108 mg, 0.629 mmol) of benzyl chloroformate was added dropwise by syringe. After completion of the addition, the reaction mixture was allowed to warm gradually to room temperature. After 1 h, the mixture was concentrated in vacuo, and the residue was purified by flash chromatography (silica gel, 0-2% methanol/dichloromethane) to afford the title compound, which was used directly in the next step. LC/MS 397 (M+1).

Step C: Benzyl 2-[4-(methylsulfonyl)phenyl]-6,7-dihydro[1,3]thiazolo[4,5-c]pyridine-5(4H)-carboxylate Essentially following the procedure for PIPERIDINE INTERMEDIATE 30, Step C, benzyl 2-[4-(methylthio)phenyl]-6,7-dihydro[1,3]thiazolo[4,5-c]pyridine-5(4H)-carboxylate from Step B above was reacted with 3-chloroperoxybenzoic acid to yield the title compound.

$^1$H NMR (500 MHz, CDCl$_3$) δ 8.10 (d, J=8 Hz, 2H), 8.02 (d, J=8 Hz, 2H), 7.42-7.37 (m, 5H), 5.23 (s, 2H), 4.81 (s, 2H), 3.91 (br apparent s, 2H), 3.11 (s, 3H), 3.0-2.9 (br m, 2H). LC/MS 429 (M+1).

Step D: 2-[4-(Methylsulfonyl)phenyl]-4,5,6,7-tetrahydro[1,3]thiazolo[4,5-c]pyridine Essentially following the procedure for PIPERIDINE INTERMEDIATE 30, Step D, benzyl 2-[4-(methylsulfonyl)phenyl]-6,7-dihydro[1,3]thiazolo[4,5-c]pyridine-5(4H)-carboxylate from Step B above was deprotected with 30% hydrogen bromide in acetic acid. The crude product was purified by flash chromatography (silica gel, 95:5 dichloromethane:methanol) to afford the title compound.

$^1$H NMR (500 MHz, CDCl$_3$) δ 8.11 (d, J=8.5 Hz, 2H), 8.012 (d, J=8.5 Hz, 2H), 4.17 (s, 2H), 3.26 (m, 2H), 3.11 (s, 3H), 2.96 (m, 2H). LC/MS 295 (M+1).

PIPERIDINE INTERMEDIATE 34

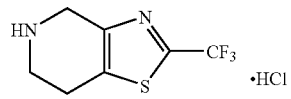

2-(Trifluoromethyl)-4,5,6,7-tetrahydro[1,3]thiazolo[4,5-c]pyridine hydrochloride Step A: tert-Butyl 4-hydroxy-3-[(trifluoroacetyl)amino]piperidine-1-carboxylate To a solution of 265 mg (1.23 mmol) of tert-butyl 3-amino-4-hydroxypiperidine-1-carboxylate (prepared according to the procedure of Marquis et al., J. Med. Chem., 41, 3563-3567 (1998)) and 0.342 mL (248 mg, 2.45 mmol) of triethylamine in 1 mL of anhydrous dichloromethane under nitrogen at 10-15° C. was added gradually 0.20 mL (297 mg, 1.41 mmol) of trifluoroacetic anhydride. After 30 min, the reaction mixture was concentrated in vacuo, and the residue was partitioned between ethyl acetate and 5% citric acid aqueous solution. The organic phase was washed with saturated sodium bicarbonate solution and dried over sodium sulfate. The filtered solution was concentrated in vacuo to give the title compound, suitable for use without further purification.

$^1$H NMR (500 MHz, CDCl$_3$) δ 7.1 J(br s, 1H), 5.25 (br s, 1H), 4.2-3.3 (complex m, 6H), 2.08 (m, 1H), 1.86 (m, 1H), 1.50 (s, 9H). LC/MS 213 (M+1-Boc).

Step B: tert-Butyl 4-oxo-3-[(trifluoroacetyl)amino]piperidine-1-carboxylate

To a solution of 362 mg (1.16 mmol) of tert-butyl 4-hydroxy-3-[(trifluoroacetyl)amino]piperidine-1-carboxylate from Step A in 10 mL of anhydrous dichloromethane was added 591 mg (1.39 mmol) of Dess-Martin periodinane (1,1,1-tris(acetyloxy)-1,1-dihydro-1,2-benziodoxol-3-(1H)-one), and the mixture was stirred at room temperature. After 4 h, an additional 500 mg (1.18 mmol) of Dess-Martin periodinane was added along with another 10 mL of dichloromethane. The next day the mixture was filtered through Celite, and the filtrate was concentrated in vacuo. Purification of the residue by flash chromatography (silica gel, 0-20% ethyl acetate/hexanes) afforded the title compound.

$^1$H NMR (500 MHz, CDCl$_3$) δ 7.34 (br s, 1H), 4.99 (m, 1H), 4.6-4.4 (complex m, 2H), 3.05 (m, 1H), 2.74-2.59 (complex m, 3H), 1.55 (s, 9H). LC/MS 211 (M+1-Boc).

Step C: tert-Butyl 2-(trifluoromethyl)-6,7-dihydro[1,3]thiazolo[4,5-c]pyridine-5(4H)-carboxylate A mixture of 167 mg (0.538 mmol) of tert-butyl 4-oxo-3-[(trifluoroacetyl)amino]piperidine-1-carboxylate from Step B, 405 mg (1 mmol) of Lawesson's Reagent, and 10 mL of anhydrous toluene was stirred at reflux under nitrogen. After 1 day, the mixture was concentrated in vacuo. The residue was purified by flash chromatography (silica gel, 0-10% ethyl acetate/hexanes) to yield the title compound.

$^1$H NMR (500 MHz, CDCl$_3$) δ 4.72 (s, 2H), 3.81 (m, 2H), 2.97 (m, 2H), 1.52 (s, 9H). LC/MS 309 (M+1).

Step D: 2-(Trifluoromethyl)-4,5,6,7-tetrahydro[1,3]thiazolo[4,5-c]pyridine, hydrochloride A mixture of 39 mg (0.127 mmol) of tert-butyl 2-(trifluoromethyl)-6,7-dihydro[1,3]thiazolo[4,5-c]pyridine-5(4H)-carboxylate from Step C and 2 mL of 4M hydrogen chloride in anhydrous dioxane was stirred at room temperature for 1 h. The reaction mixture was then concentrated in vacuo. Repeated trituration of the residue with diethyl ether gave a solid, which was collected on a filter and washed with diethyl ether to give the title compound as a hydrochloride salt, mp 185-186° C.

$^1$H NMR (500 MHz, CDCl$_3$) δ 4.52 (br apparent s, 2H), 3.64 (br apparent s, 2H), 3.41 (br apparent s, 2H). LC/MS 209 (M+1).

PIPERIDINE INTERMEDIATE 35

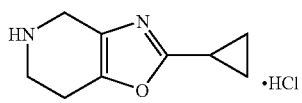

2-Cyclopropyl-4,5,6,7-tetrahydro[1,3]oxazolo[4,5-c]pyridine, hydrochloride

Step A: tert-Butyl 3-[(cyclopropylcarbonyl)amino]-4-hydroxypiperidine-1-carboxylate To a solution of 265 mg (1.23 mmol) of tert-butyl 3-amino-4-hydroxypiperidine-1-carboxylate (prepared according to the procedure of Marquis et al., *J. Med. Chem.*, 41, 3563-3567 (1998)) and 0.258 mL (187 mg, 1.85 mmol) of triethylamine in 3 mL of anhydrous dichloromethane under nitrogen at 10° C. was added gradually 0.112 mL (129 mg, 1.23 mmol) of cyclopropanecarbonyl chloride. After 1 h, the reaction mixture was concentrated in vacuo, and the residue was partitioned between ethyl acetate and 5% citric acid aqueous solution. The organic phase was washed with saturated sodium carbonate solution and then dried over sodium sulfate. The filtered solution was concentrated in vacuo to give the title compound, suitable for use without further purification.

$^1$H NMR (500 MHz, CDCl$_3$) δ 6.23 (br s, 1H), 3.98 (dd, J=13 Hz, 3.5 Hz, 1H), 3.88 (br s, 1H), 3.8-3.65 (complex m, 4H), 3.10 (m, 1H), 3.02 (m, 1H), 1.95 (m, 1H), 1.57 (m, 1H), 1.48 (s, 9H), 1.41 (m, 1H), 0.98 (m, 2H), 0.78 (m, 2H). LC/MS 285 (M+1).

Step B: tert-Butyl 3-[(cyclopropylcarbonyl)amino]-4-oxopiperidine-1-carboxylate

Essentially following the procedure for PIPERIDINE INTERMEDIATE 34, Step B, tert-butyl 3-[(cyclopropylcarbonyl)amino]-4-hydroxypiperidine-1-carboxylate from Step A above was reacted with Dess-Martin periodinane. Purification of the residue by flash chromatography (silica gel, 0-33% ethyl acetate/hexanes) afforded the title compound.

$^1$H NMR (500 MHz, CDCl$_3$) δ 6.55 (br s, 1H), 4.85 (m, 1H), 4.53 (br m, 2H), 3.05 (br m, 1H), 2.69-2.61 (complex m, 2H), 2.54 (m, 1H), 1.53 (s, 9H), 1.47 (m, 1H), 1.00 (m, 2H), 0.81 (m, 2H). LC/MS 283 (M+1).

Step C: tert-Butyl 2-cyclopropyl-6,7-dihydro[1,3]oxazolo[4,5-c]pyridine-5(4H)-carboxylate A mixture of 59 mg (0.209 mmol) of tert-butyl 3-[(cyclopropylcarbonyl)amino]-4-oxopiperidine-1-carboxylate from Step B, 100 mg (0.418 mmol) of Burgess reagent, and 3 mL of anhydrous tetrahydrofuran was stirred at reflux overnight. The tetrahydrofuran phase was then decanted, leaving behind an oily phase, which was discarded. The solvent was removed in vacuo, and the residue was purified by flash chromatography (silica gel, 0-20% ethyl acetate/hexanes) to yield the title compound.

$^1$H NMR (500 MHz, CDCl$_3$) δ 4.30 (s, 2H), 3.73 (m, 2H), 2.68 (m, 2H), 2.06 (m, 1H), 1.48 (s, 9H), 1.05 (m, 2H), 1.00 (m, 2H). LC/MS 265 (M+1).

Step D: 2-Cyclopropyl-4,5,6,7-tetrahydro[1,3]oxazolo[4,5-c]pyridine hydrochloride Essentially following the procedure for PIPERIDINE INTERMEDIATE 34, Step D, tert-butyl 2-cyclopropyl-6,7-dihydro[1,3]oxazolo[4,5-c]pyridine-5(4H)-carboxylate from Step C above was deprotected with 4M hydrogen chloride in anhydrous dioxane to give the title compound as a hydrochloride salt.

$^1$H NMR (500 MHz, CD$_3$OD) δ 4.14 (s, 2H), 3.58 (m, 2H), 3.00 (m, 2H), 2.11 (m, 1H), 1.10 (m, 2H), 1.02 (m, 2H). LC/MS 165 (M+1).

PIPERIDINE INTERMEDIATE 36

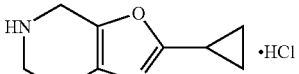

2-Cyclopropyl-4,5,6,7-tetrahydro[1,3]oxazolo[5,4-c]pyridine, hydrochloride

Step A: tert-Butyl 4-[(cyclopropylcarbonyl)amino]-3-hydroxypiperidine-1-carboxylate Essentially following the procedure for PIPERIDINE INTERMEDIATE 35, Step A, tert-butyl 4-amino-3-hydroxypiperidine-1-carboxylate (prepared according to the procedure of Marquis et al., *J. Med. Chem.*, 41, 3563-3567 (1998)) was reacted with cyclopropanecarbonyl chloride to give the title compound, suitable for use without further purification.

¹H NMR (500 MHz, CDCl₃) δ 6.07 (br s, 1H), 4.3-4.0 (complex m, 3H), 3.74 (m, 1H), 3.40 (m, 1H), 2.74 (m, 1H), 2.60 (apparent t, J=11.7 Hz, 1H), 1.94 (br d, J=11.7 Hz, 1H), 1.47 (s, 9H), 1.5-1.4 (partially obscured m, 2H), 1.03 (m, 2H), 0.82 (m, 2H). LC/MS 185 (M+1-Boc).

Step B: tert-Butyl 4-[(cyclopropylcarbonyl)amino]-3-oxopiperidine-1-carboxylate

A dried flask was charged with 0.38 mL of anhydrous dichloromethane and 0.116 mL (0.232 mmol) of 2M oxalyl chloride in anhydrous tetrahydrofuran. The solution was stirred under nitrogen at −60° C. as a solution of 0.036 mL (40 mg, 0.506 mmol) of dimethyl sulfoxide in 0.105 mL of dichloromethane was added dropwise over 5 min. Stirring was continued at −60° C. for an additional 10 min. Then a solution of 60 mg of tert-butyl 4-[(cyclopropylcarbonyl) amino]-3-hydroxypiperidine-1-carboxylate from Step A was added. After 15 min at 60° C., 0.161 mL (117 mg, 1.16 mmol) of triethylamine was added. After an additional 30 min at −60° C., the reaction was quenched with brine and extracted with diethyl ether. The organic phase was concentrated in vacuo. Purification of the residue by flash chromatography (silica gel, 33-50% ethyl acetate/hexanes) afforded the title compound.

¹H NMR (500 MHz, CDCl₃) δ 6.52 (br s, 1H), 4.65 (m, 1H), 4.36 (d, J=7.4 Hz, 1H), 4.02 (br m, 3H), 3.55 (br m, 1H), 2.72 (m, 1H), 1.66 (m, 1H), 1.51 (s, 9H), 1.01 (m, 2H), 0.83 (m, 2H). LC/MS 183 (M+1-Boc).

Step C: tert-Butyl 2-cyclopropyl-6,7-dihydro[1,3]oxazolo[5,4-c]pyridine-5(4H)-carboxylate Essentially following the procedure for PIPERIDINE INTERMEDIATE 35, Step C, tert-butyl 4-[(cyclopropylcarbonyl)amino]-3-oxopiperidine-1-carboxylate from Step B above was reacted with Burgess reagent to afford the title compound.

¹H NMR (500 MHz, CDCl₃) δ 4.45 (s, 2H), 3.69 (br apparent s, 2H), 2.59 (br apparent s, 2H), 2.04 (m, 1H), 1.50 (s, 9H), 1.06-1.02 (complex m, 4H). LC/MS 265 (M+1).

Step D: 2-Cyclopropyl-4,5,6,7-tetrahydro[1,3]oxazolo[5,4-c]pyridine, hydrochloride Essentially following the procedure for PIPERIDINE INTERMEDIATE 34, Step D, tert-butyl 2-cyclopropyl-6,7-dihydro[1,3]oxazolo[4,5-c]pyridine-5(4H)-carboxylate from Step C above was deprotected with 4M hydrogen chloride in anhydrous dioxane in the presence of some anhydrous methanol for solubility to give the title compound as a hydrochloride salt.

¹H NMR (500 MHz, CD₃OD) δ 4.44 (br s, 2H), 3.65 (br m, 2H), 3.00 (br apparent s, 2H), 2.26 (br apparent s, 1H), 1.10 (m, 2H), 1.3-1.15 (br m, 4H). LC/MS 165 (M+1).

PIPERIDINE INTERMEDIATE 37

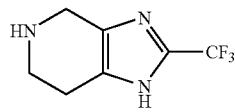

2-(Trifluoromethyl)-4,5,6,7-tetrahydro-1H-imidazo[4,5-c]pyridine

Platinum oxide (0.25 g) was added to a solution of 1.25 g (6.68 mmol) 2-(trifluoromethyl)-1H-imidazo[4,5-c]pyridine (prepared according to the procedure of B. G. Jones, et al., *J. Chem. Soc. Perkin Trans. I*, 2685-2691 (1996)) in 35 mL of ethanol. The mixture was hydrogenated for 18 h at 1000 psi. After filtration and evaporation, the residue was purified by flash column chromatography (silica gel, 10-22% methanol/dichloromethane) to give the title compound.

¹H NMR (500 MHz, CD₃OD) δ 3.82 (s, 2H), 3.10 (t, 2H, J=6 Hz), 2.69 (t, 2H, J=6 Hz). LC/MS 192 (M+1).

PIPERIDINE INTERMEDIATE 38

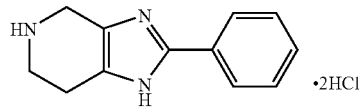

2-Phenyl-4,5,6,7-tetrahydro-1H-imidazo[4,5-c]pyridine dihydrochloride

Step A: tert-Butyl trans-4-azido-3-hydroxy-1-piperidinecarboxylate

Sodium azide (1.67 g, 25.7 mmol) and ammonium chloride (0.98 g, 18 mmol) were added to a solution of 1.85 g (9.28 mmol) of tert-butyl 7-oxa-3-azabicyclo[4.1.0]heptane-3-carboxylate (prepared according to the procedure of S. Zhao, et al., *Heterocycles*, 39: 163-170 (1994)) in ethanol (36 mL) and water (12 mL). The resultant mixture was stirred and heated in an oil bath at 70° C. for 16 h. After cooling to room temperature, the mixture was partitioned between ethyl ether (100 mL) and a mixture of brine (25 mL) and water (7 mL). The aqueous layer was extracted with ethyl ether (50 mL) and the organic layers were washed with brine (25 mL). The organic layers were dried over sodium sulfate, decanted, and evaporated. The residue was dissolved in ethyl acetate (25 mL) and the resultant solution was washed sequentially with saturated aqueous sodium bicarbonate solution (10 mL) and brine (10 mL), dried over sodium sulfate, decanted, and evaporated. Purification by flash column chromatography (silica gel, 10-20% ethyl acetate/hexanes) gave the title compound as a colorless oil.

¹H NMR (500 MHz, CD₃OD) δ 4.05 (bd, 1H, J=12 Hz), 3.93 (dm, 1H, J=14 Hz), 3.38-3.31 (m, 2H), 2.93-2.80 (bm, 1H), 2.77-2.60 (bm, 1H), 1.93 (dq, 1H, J=14, 3 Hz), 1.45 s, 9H), 1.40-1.29 (m, 1H). LC/MS 143 (M+1-Boc).

Continued elution of the silica gel column gave the isomeric product tert-butyl trans-3-azido-4-hydroxy-1-piperidinecarboxylate.

¹H NMR (500 MHz, CD₃OD) δ 4.40-3.73 (bm, 2H), 3.61-3.54 (bm, 1H), 3.27-3.20 (bm, 1H), 3.04-2.93 (bm, 1H), 1.89 (dtd, 1H, J=13.5, 5, 4 Hz), 1.40-1.40 (m, 1H), 1.46 (s, 9H).

Step B: tert-Butyl cis-3,4-diazido-1-piperidinecarboxylate

Methanesulfonyl chloride (0.505 mL, 747 mg, 6.52 mmol) was added dropwise over 8 min to a solution of tert-butyl trans-4-azido-3-hydroxy-1-piperidinecarboxylate (1.43 g, 5.90 mmol) and triethylamine (1.25 mL, 0.91 g, 8.97 mmol) in dichloromethane (10.0 mL) cooled in an ice bath. After 1.5 h, the mixture was diluted with dichloromethane (35 mL) and washed sequentially with 1N aqueous hydrochloric acid (20 mL), saturated aqueous sodium bicarbonate solution (15 mL), and brine (15 mL). The organic layer was dried over sodium sulfate, decanted, and evaporated to give tert-butyl trans-4-azido-3-[(methylsulfonyl)oxy]-1-piperidinecarboxylate as a light amber syrup.

Sodium azide (1.03 g, 15.8 mmol) was added to N,N-dimethylformamide (50 mL) containing the crude tert-butyl trans-4-azido-3-[(methylsulfonyl)oxy]-1-piperidinecarboxylate. The mixture was heated in an oil bath at 100° C. for 16 h and at 110° C. for 20 h. The solvent was removed on a rotary evaporator at 35-40° C. The residue was partitioned between 1:1 hexanes/ethyl acetate (75 mL) and brine (25 mL) mixed with water (10 mL). The organic layer was washed with water (2×35 mL) followed by brine (15 mL), and then dried over sodium sulfate, decanted, and evaporated. Purification by flash column chromatography (silica gel, 15-25% ethyl acetate/hexanes) gave the title compound.
$^1$H NMR (500 MHz, CD$_3$OD) δ 4.08-3.68 (m, 4H), 3.30-2.90 (m, 3H), 1.86-1.71 (m, 2H), 1.47 (s, 9).

Step C: tert-Butyl cis-3,4-diamino-1-piperidinecarboxylate

10% Palladium on carbon (0.10 g) was added to a solution of tert-butyl cis-3,4-diazido-1-piperidinecarboxylate (0.90 g, 3.4 mmol) in 95% ethanol and the mixture was stirred under hydrogen (1 atm) for 30 h. Filtration through a pad of Celite® and evaporation of the solvent gave the title compound as a colorless syrup.
$^1$H NMR (500 MHz, CD$_3$OD) δ 3.75 (dt, 1H, J=13, 5 Hz), 3.69 (dd, 1H, J=13, 4 Hz), 3.18 (d, 1H, J=13 Hz), 3.09-2.98 (bm, 1H), 2.91-2.86 (m, 1H), 2.86-2.80 (bm, 1H), 1.60-1.54 (m, 2H), 1.45 (s, 9H). LC/MS 160 (M+1-56).

Step D: tert-Butyl 2-phenyl-1,3a,4,6,7,7a-hexahydro-5H-imidazo[4,5-c]pyridine-5-carboxylate Ethyl benzimidate hydrochloride (43 mg, 0.23 mmol) was added to a solution of tert-butyl cis-3,4-diamino-1-piperidinecarboxylate (50 mg, 0.23 mmol) in anhydrous ethanol (1.0 mL). After 1.5 h at room temperature, the mixture was heated in a 75° C. oil bath for 30 min. After cooling to room temperature and standing for 1 h, the mixture was concentrated under vacuum and the residue was partitioned between dichloromethane (15 mL) and 5% aqueous sodium bicarbonate solution (10 mL). The aqueous layer was extracted with dichloromethane (2×15 mL) and the organic layers were dried over sodium sulfate, decanted, and evaporated to give the title compound as an amber syrup. LC/MS 302 (M+1).

Step F: tert-Butyl 2-phenyl-4,5,6,7-tetrahydro-1H-imidazo[4,5-c]pyridine-5-carboxylate Dimethyl sulfoxide (0.012 mL, 14 mg, 0.17 mmol) in dichloromethane (0.050 mL) was added slowly to a solution of oxalyl chloride (0.008 mL, 12 mg, 0.09 mmol) in dichloromethane (1.0 mL) cooled to −70° C. After 5 min, a solution of tert-butyl 2-phenyl-1,3a,4,6,7,7a-hexahydro-5H-imidazo[4,5-c]pyridine-5-carboxylate (37 mg, 0.12 mmol) in dichloromethane (0.6 mL) was added slowly, followed 1 h later by triethylamine (0.060 mL, 44 mg, 0.43 mmol). After 1 h, the cooling bath was removed and the mixture was allowed to warm to room temperature. The mixture was added to water (20 mL) and extracted with dichloromethane (3×25 mL). The organic layers were washed with brine (20 mL), dried over sodium sulfate, decanted, and evaporated. Purification by flash column chromatography (silica gel, 2.5-5% methanol/0.5-1% concentrated ammonium hydroxide/dichloromethane) gave the title compound as an amber syrup. LC/MS 300 (M+1).

Step G: 2-Phenyl-4,5,6,7-tetrahydro-1H-imidazo[4,5-c]pyridine dihydrochloride

A solution of methanolic hydrogen chloride (approx. 1.6M, 1.0 mL) was added to tert-butyl 2-phenyl-4,5,6,7-tetrahydro-1H-imidazo[4,5-c]pyridine-5-carboxylate (24 mg, 0.080 mmol) in 0.20 mL of methanol. After 3 h, the solution was concentrated under vacuum. Methanol (two portions) was added, with evaporation of the solvent after each addition. The title compound was obtained as a white solid. LC/MS 200 (M+1).

PIPERIDINE INTERMEDIATE 39

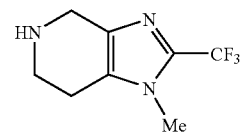

1-Methyl-2-(trifluoromethyl)-4,5,6,7-tetrahydro-1H-imidazo[4,5-c]pyridine

Step A: N-Methyl-3-nitro-4-pyridinamine

A small portion of 40% aqueous methylamine was added to acetic acid (2.2 mL) and the solution was cooled in an ice bath. Additional 40% aqueous methylamine (total of 3.4 mL, 39 mmol) was then added followed by 4-ethoxy-3-nitropyridine hydrochloride (2.00 g, 9.77 mmol). The mixture was heated in a 105° C. oil bath for 8 h and stirred at room temperature for an additional 10 h. The mixture was partitioned between ethyl acetate (50 mL) and 2.5N aqueous sodium hydroxide solution (25 mL). Sodium chloride was added to the aqueous layer, which was then extracted with additional ethyl acetate (5×50 mL). The organic layers were washed with brine (10 mL), dried over sodium sulfate, decanted, and evaporated. Purification by flash column chromatography (silica gel, 15% ethyl acetate/dichloromethane) gave the title compound as yellow crystals.
$^1$H NMR (500 MHz, CD$_3$OD) δ 9.06 (s, 1H), 8.22 (d, 1H, J=7 Hz), 6.95 (d, 1H, J=7 Hz), 3.05 (s, 3H). LC/MS 154 (M+1).

Step B: N$^4$-Methyl-3,4-pyridinediamine

10% Palladium on carbon (100 mg) was added to a suspension of N-methyl-3-nitro-4-pyridinamine (1.23 g, 8.03 mmol) in 95% ethanol (15 mL) and the mixture was stirred under hydrogen at 1 atm. After 3.5 h, additional 10% palladium on carbon (100 mg) was added and stirring was continued for 4 h. Filtration through Celite® and evaporation of the solvent gave the title compound as a tan solid.
$^1$H NMR (500 MHz, CD$_3$OD) δ 7.71 (d, 1H, J=6 Hz), 7.69 (s, 1H), 6.46 (d, 1H, J=6 Hz), 2.88 (s, 3H). LC/MS 124 (M+1).

Step C: 1-Methyl-2-(trifluoromethyl)-1H-imidazo[4,5-c]pyridine

Trifluoroacetic acid (5.0 mL) was added to N$^4$-methyl-3,4-pyridinediamine (450 mg, 3.65 mmol) and the mixture was heated at reflux for 48 h. After cooling to room temperature, the excess trifluoroacetic acid was removed on a rotary evaporator. The residue was distilled at reduced pressure using a Kugelrohr apparatus heated to an oven temperature of 190° C. The distillate was partitioned between dichloromethane (30 mL) and 2.5N aqueous sodium hydroxide solution (15 mL). The aqueous layer was extracted with dichloromethane (30 mL) and the organic layers were washed with brine (15 mL), dried over sodium sulfate, decanted, and evaporated to give the title compound as a white solid.

¹H NMR (500 MHz, CD₃OD) δ 9.06 (s, 1H), 8.51 (d, 1H, J=6 Hz), 7.78 (d, 1H, J=6 Hz), 4.04 (s, 3H). LC/MS 202 (M+1).

Step D: 1-Methyl-2-(trifluoromethyl)-4,5,6,7-tetrahydro-1H-imidazo[4,5-c]pyridine Platinum oxide (0.050 g) was added to a solution of 1-methyl-2-(trifluoromethyl)-1H-imidazo[4,5-c]pyridine (0.250 g, 1.24 mmol) in ethanol (8.0 mL). The mixture was hydrogenated for 14.5 h at 1000 psi and 39° C. Filtration and evaporation gave the title compound.

¹H NMR (500 MHz, CD₃OD) δ 3.75 (s, 2H), 3.68 (s, 3H), 3.10 (t, 2H, J=6 Hz), 2.67 (t, 2H, J=6 Hz). LC/MS 206 (M+1).

PIPERIDINE INTERMEDIATE 40

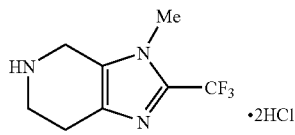

3-Methyl-2-(trifluoromethyl)-4,5,6,7-tetrahydro-3H-imidazo[4,5-c]pyridine, dihydrochloride Step A: tert-Butyl 2-(trifluoromethyl)-1,4,6,7-tetrahydro-5H-imidazo[4,5-c]pyridine-5-carboxylate Di-tert-butyl-dicarbonate (720 mg, 3.30 mmol) was added to a stirred suspension of 2-(trifluoromethyl)-4,5,6,7-tetrahydro-1H-imidazo[4,5-c]pyridine (PIPERIDINE INTERMEDIATE 37, 600 mg, 3.14 mmol) in 1,4-dioxane (12 mL). After 15 h, the solvent was evaporated and the residue was partitioned between ethyl acetate (40 mL) and saturated aqueous sodium bicarbonate solution (25 mL). The organic layer was washed with brine (25 mL) and the aqueous layers were extracted with ethyl acetate (2×40 mL). The organic layers were dried over sodium sulfate, decanted, and evaporated. Toluene (three portions) was added, with concentration under vacuum after each addition. Purification by flash column chromatography (silica gel, 10-20% ethyl acetate/hexanes) gave the title compound.

Step B: tert-Butyl 3-methyl-2-(trifluoromethyl)-3,4,6,7-tetrahydro-5H-imidazo[4,5-c]pyridine-5-carboxylate Potassium bis(trimethylsilyl)amide (0.5M in toluene, 0.90 mL, 0.45 mmol) was added to a solution of tert-butyl 2-(trifluoromethyl)-1,4,6,7-tetrahydro-5H-imidazo[4,5-c]pyridine-5-carboxylate (120 mg, 0.41 mmol) in tetrahydrofuran (2.0 mL) at −20 to −25° C. After 30 min, iodomethane (0.030 mL, 68 mg, 0.48 mmol) was added and the mixture was allowed to warm slowly to room temperature. After 1.5 h, the mixture was partitioned between ethyl acetate (25 mL) and saturated aqueous sodium bicarbonate solution (15 mL). The aqueous layer was extracted with ethyl acetate (2×25 mL) and the organic layers were washed with brine (10 mL). The organic layers were dried over sodium sulfate, decanted, and evaporated. Purification by flash column chromatography (silica gel, 20-40% ethyl ether/hexanes) gave the title compound as the first isomer eluted. LC/MS 306 (M+1).

The second isomer eluted was the isomeric product, tert-butyl 1-methyl-2-(trifluoromethyl)-1,4,6,7-tetrahydro-5H-imidazo[4,5-c]pyridine-5-carboxylate. LC/MS 306 (M+1).

Step C: 3-Methyl-2-(trifluoromethyl)-4,5,6,7-tetrahydro-3H-imidazo[4,5-c]pyridine, dihydrochloride A solution of methanolic hydrogen chloride (about 1.6M, 0.95 mL) was added to tert-butyl 3-methyl-2-(trifluoromethyl)-3,4,6,7-tetrahydro-5H-imidazo[4,5-c]pyridine-5-carboxylate (23 mg, 0.076 mmol) in 0.20 mL of methanol. After 3 h, the solution was concentrated under vacuum. Methanol was added and the solvent was evaporated to give the title compound as a white glass. LC/MS 206 (M+1).

PIPERIDINE INTERMEDIATE 41

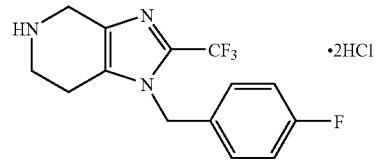

1-(4-Fluorobenzyl)-2-(trifluoromethyl)-4,5,6,7-tetrahydro-1H-imidazo[4,5-c]pyridine dihydrochloride Step A: tert-Butyl 1-(4-fluorobenzyl)-2-(trifluoromethyl)-1,4,6,7-tetrahydro-5H-imidazo[4,5-c]pyridine-5-carboxylate A solution of tert-butyl 2-(trifluoromethyl)-1,4,6,7-tetrahydro-5H-imidazo[4,5-c]pyridine-5-carboxylate (PIPERIDINE INTERMEDIATE 40, Step A, 197 mg, 0.676 mmol) in N,N-dimethylformamide (1.0 mL) was added to a stirred suspension of sodium hydride (32 mg of 60% oil dispersion, 0.80 mmol) in N,N-dimethylformamide at 0° C. in an ice bath. The ice bath was then removed and the reaction mixture was stirred until the sodium hydride had been consumed (30-40 min). 4-Fluorobenzylbromide (0.140 mL, 212 mg, 1.12 mmol) was added and the reaction was stirred for 4 h at room temperature. After standing overnight at −20° C., the reaction mixture was partitioned between water (15 mL) and ethyl acetate (30 mL). The aqueous layer was extracted with ethyl acetate (2×30 mL) and the organic layers were washed with brine (15 mL), dried over sodium sulfate, decanted, and evaporated to give an amber syrup. Purification by flash column chromatography (silica gel, 5% ethyl ether/dichloromethane) gave the title compound as the first regioisomer eluted. LC/MS 400 (M+1).

The second isomer eluted was the isomeric product tert-butyl 3-(4-fluorobenzyl)-2-(trifluoromethyl)-3,4,6,7-tetrahydro-5H-imidazo[4,5-c]pyridine-5-carboxylate. LC/MS 400 (M+1).

Step B: 1-(4-Fluorobenzyl)-2-(trifluoromethyl)-4,5,6,7-tetrahydro-1H-imidazo[4,5-c]pyridine dihydrochloride A solution of methanolic hydrogen chloride (about 1.6M, 2.5 mL) was added to tert-butyl 1-(4-fluorobenzyl)-2-(trifluoromethyl)-1,4,6,7-tetrahydro-5H-imidazo[4,5-c]pyridine-5-carboxylate (81 mg, 0.20 mmol) in 0.20 mL of methanol. After 5 h, the solution was concentrated under vacuum. Methanol (five portions) was added, with evaporation of the solvent after each addition. The title compound was obtained as a light amber syrup. LC/MS 300 (M+1).

PIPERIDINE INTERMEDIATE 42

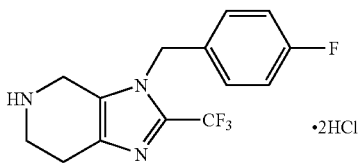

3-(4-Fluorobenzyl)-2-(trifluoromethyl)-4,5,6,7-tetrahydro-3H-imidazo[4,5-c]pyridine dihydrochloride A solution of methanolic hydrogen chloride (about 1.6M, 1.6 mL) was added to tert-butyl 3-(4-fluorobenzyl)-2-(trifluoromethyl)-3,4,6,7-tetrahydro-5H-imidazo[4,5-c]pyridine-5-carboxylate (PIPERIDINE INTERMEDIATE 41, Step A, 52 mg, 0.13 mmol) in 0.20 mL of methanol. After 5 h, the solution was concentrated under vacuum. Methanol (five portions) was added, with evaporation of the solvent after each addition. The title compound was obtained as a light amber syrup. LC/MS 300 (M+1).

PIPERIDINE INTERMEDIATE 43

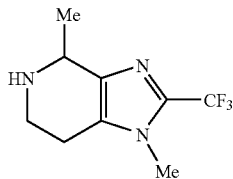

1,4-Dimethyl-2-(trifluoromethyl)-4,56,7-tetrahydro-1H-imidazo[4,5-c]pyridine

Step A: Phenyl 1,4-dimethyl-2-(trifluoromethyl)-1,4-dihydro-5H-imidazo[4,5-c]pyridine-5-carboxylate Methylmagnesium bromide (1.4 M solution in 75:25 toluene/tetrahydrofuran, 0.20 mL, 2.8 mmol) was added to a solution of 50 mg (0.25 mmol) of 1-methyl-2-(trifluoromethyl)-1H-imidazo[4,5-c]pyridine (from PIPERIDINE INTERMEDIATE 39, Step C) in tetrahydrofuran (1.5 mL) stirred in a −20° C. cooling bath. A solution of phenyl chloroformate (0.031 mL, 39 mg, 0.25 mmol) in tetrahydrofuran (0.6 mL) was then added over 15 min. After 30 min, the bath temperature was allowed to increase to 0° C. over 1 h. The reaction mixture was partitioned between water (20 mL) and ethyl acetate (25 mL). The organic layer was washed sequentially with saturated aqueous sodium bicarbonate solution (20 mL) and brine (20 mL). The aqueous layers were extracted with ethyl acetate (25 mL). The organic layers were dried over sodium sulfate, decanted, and evaporated to give the title compound as an amber syrup. LC/MS 338 (M+1).

Step B: tert-Butyl 1,4-dimethyl-2-(trifluoromethyl)-1,4-dihydro-5H-imidazo[4,5-c]pyridine-5-carboxylate Potassium tert-butoxide (about 8 M in tetrahydrofuran, 0.125 mL) was added over 15 min to a solution of phenyl 1,4-dimethyl-2-(trifluoromethyl)-1,4-dihydro-5H-imidazo[4,5-c]pyridine-5-carboxylate (83 mg, 0.25 mmol) in tetrahydrofuran (3.0 mL) stirred in a −45° C. bath. After 30 min, the solution was allowed to warm to room temperature over 1.5 h. The reaction mixture was partitioned between water (20 mL) and ethyl acetate (25 mL), and the aqueous layer was extracted with ethyl acetate (2×25 mL). The organic layers were washed sequentially with 1.25N aqueous sodium hydroxide solution (20 mL) and brine (20 mL), dried over sodium sulfate, decanted, and evaporated. Purification by flash column chromatography (silica gel, 5-10% ethyl acetate/hexanes) gave the title compound as a colorless syrup. LC/MS 318 (M+1).

Step C: tert-Butyl 1,4-dimethyl-2-(trifluoromethyl)-1,4,6,7-tetrahydro-5H-imidazo[4,5-c]pyridine-5-carboxylate 10% Palladium on carbon (11 mg) was added to a solution of tert-butyl 1,4-dimethyl-2-(trifluoromethyl)-1,4-dihydro-5H-imidazo[4,5-c]pyridine-5-carboxylate (55 mg, 0.17 mmol) in ethanol (2.0 mL), and the resultant mixture was stirred under hydrogen (1 atm) for 2.5 h. Filtration and evaporation of the solvent gave the crude product. Purification by flash column chromatography (silica gel, 5-10% ethyl acetate/hexanes) gave the racemic title compound as a colorless oil. LC/MS 320 (M+1).

Separation of the enantiomers of the title compound was accomplished by HPLC using a CHIRALCEL OD column, eluting with 10% 2-propanol/hexanes. The second enantiomer eluted from the column yielded the more active diastereomer listed in Table 2.

Step D: 1,4-Dimethyl-2-(trifluoromethyl)-4,5,6,7-tetrahydro-1H-imidazo[4,5-c]pyridine A solution of methanolic hydrogen chloride (about 1.6M, 1.8 mL) was added to tert-butyl 1,4-dimethyl-2-(trifluoromethyl)-1,4,6,7-tetrahydro-5H-imidazo[4,5-c]pyridine-5-carboxylate (45 mg, 0.14 mmol) in 0.20 mL of methanol. After 2 h, the solution was concentrated under vacuum. The residue was dissolved in methanol and the solution was evaporated again to provide the title compound. LC/MS 220 (M+1).

PIPERIDINE INTERMEDIATE 44

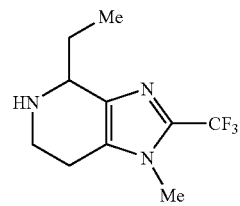

4-Ethyl-1-methyl-2-(trifluoromethyl)-4,5,6,7-tetrahydro-1H-imidazo[4,5-c]pyridine The title compound was prepared essentially as described for PIPERIDINE INTERMEDIATE 43 (Steps A-D), except that ethylmagnesium bromide was used instead of methylmagnesium bromide in Step A. The separation of the enantiomers in Step C was accomplished using a CHIRALCEL OD column, eluting with 3% 2-propanol/hexanes. The first-eluting enantiomer was used to prepare the more active diastereomer listed in Table 2. LC/MS 234 (M+1).

PIPERIDINE INTERMEDIATE 45

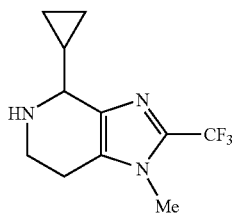

4-Cyclopropyl-1-methyl-2-(trifluoromethyl)-4,5,6,7-tetrahydro-1H-imidazo[4,5-c]pyridine The title compound was prepared essentially as described for PIPERIDINE INTERMEDIATE 43 (Steps A-D), except that cyclopropylmagnesium bromide was used instead of methylmagnesium bromide in Step A. The separation of the enantiomers in Step C was accomplished using a CHIRALCEL OD column, eluting with 12% 2-propanol/hexanes. The second-eluting enantiomer was used to prepare the more active diastereomer listed in Table 2. LC/MS 246 (M+1).

PIPERIDINE INTERMEDIATE 46

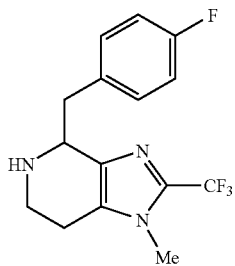

4-(4-Fluorobenzyl)-1-methyl-2-(trifluoromethyl)-4,5,6,7-tetrahydro-1H-imidazo[4,5-c]pyridine The title compound was prepared essentially as described for PIPERIDINE INTERMEDIATE 43 (Steps A-D), except that in Step A 4-fluorobenzylmagnesium chloride was instead of methylmagnesium bromide, and the phenyl chloroformate was added before the Grignard reagent. The separation of the enantiomers in Step C was accomplished using a CHIRALCEL OD column, eluting with 9% ethanol/hexanes. The second-eluting enantiomer was used to prepare the more active diastereomer listed in Table 2. LC/MS 314 (M+1).

PIPERIDINE INTERMEDIATE 47

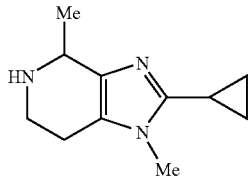

1,4-Dimethyl-2-cyclopropyl-4,5,6,7-tetrahydro-1H-imidazo[4,5-c]pyridine

Step A: 2-Cyclopropyl-1-methyl-1H-imidazo[4,5-c]pyridine

Cyclopropanecarbonyl chloride (0.105 mL, 121 mg, 1.16 mmol) was added over 5 min to a stirred mixture of $N^4$-methyl-3,4-pyridinediamine (123 mg, 1.00 mmol) and triethylamine (0.420 mL, 305 mg, 3.0 mmol) in dichloromethane (3.5 mL). The mixture was stirred 1 h at room temperature and was then evaporated. The residue was dissolved in 4 mL of acetic acid and stirred for 2 h at room temperature. The mixture was evaporated and the residue was partitioned between ethyl acetate (25 mL) and saturated aqueous sodium bicarbonate solution (10 mL) along with 2.5N aqueous sodium hydroxide solution to adjust the pH of the aqueous layer to 9. The aqueous layer was extracted with additional ethyl acetate (3×25 mL). The organic layers were washed with brine (10 mL), dried over sodium sulfate, decanted and evaporated.

The residue was dissolved in acetic acid (5 mL) and the mixture was heated at reflux temperature for 3 d. After evaporation of the acetic acid, the residue was dissolved in dichloromethane (30 mL) and washed with 2.5N aqueous sodium hydroxide solution. The aqueous layer was extracted with dichloromethane (30 mL) and the organic layers were dried over sodium sulfate, decanted, and evaporated. Purification by flash column chromatography (silica gel, 2.5-3.5% methanol/0.5-0.7% conc. aqueous ammonium hydroxide/dichloromethane) gave the title compound as a solid.

$^1$H NMR (500 MHz, CD$_3$OD) δ 8.71 (s, 1H), 8.28 (d, 1H, J=7 Hz), 7.54 (d, 1H, J=7 Hz), 3.93, s, 3H), 2.31-2.24 (m, 1H), 1.25-1.15 (m, 4H). LC/MS 174 (M+1).

Steps B-E: 1,4-Dimethyl-2-cyclopropyl-4,5,6,7-tetrahydro-1H-imidazo[4,5-c]pyridine The title compound was prepared essentially as described for PIPERIDINE INTERMEDIATE 43 (Steps A-D), except that 2-cyclopropyl-1-methyl-1H-imidazo[4,5-c]pyridine was used instead of 1-methyl-2-(trifluoromethyl)-1H-imidazo[4,5-c]pyridine. The separation of the enantiomers was accomplished using a CHIRALCEL OD column, eluting with 3.5% ethanol in hexanes. The second-eluting enantiomer was used to prepare the more active diastereomer listed in Table 2. LC/MS 192 (M+1).

PIPERIDINE INTERMEDIATE 48

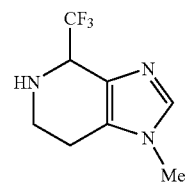

1-Methyl-4-(trifluoromethyl)-4,5,6,7-tetrahydro-1H-imidazo[4,5-c]pyridine

Step A: tert-Butyl 4-(trifluoromethyl)-1,4,6,7-tetrahydro-5H-imidazo[4,5-c]pyridine-5-carboxylate Di-tert-butyl dicarbonate (120 mg, 0.55 mmol) in dichloromethane (0.40 mL) was added to a stirred suspension of 100 mg (0.52 mmol) of 4-(trifluoromethyl)-4,5,6,7-tetrahydro-1H-imidazo[4,5-c]pyridine (prepared according to the procedure of S. Fuji, et al., *J. Fluorine Chem.*, 35: 581-589 (1987)) in a mixture of dichloromethane (2.0 mL) and tetrahydrofuran (1.0 mL). After 4 d, additional di-tert-butyl dicarbonate (120 mg, 0.55 mmol) was added and stirring was continued. After another 3 d, the mixture was concentrated under vacuum and the residue was dissolved in methanol (0.75 mL). Methanolic ammonia (2N, 0.75 mL, 1.5 mmol) was added and the solution was stirred for 48 h before being concentrated under vacuum. Purification by flash column chromatography (silica gel, 20% ethyl acetate/hexanes) gave the title compound. LC/MS 292 (M+1).

Step B: tert-Butyl 1-methyl-4-(trifluoromethyl)-1,4,6,7-tetrahydro-5H-imidazo[4,5-c]pyridine-5-carboxylate Potassium bis(trimethylsilyl)amide (0.5M in toluene, 1.05 mL, 0.53 mmol) was added to a solution of tert-butyl 4-(trifluoromethyl)-1,4,6,7-tetrahydro-5H-imidazo[4,5-c]pyridine-5-carboxylate (134 mg, 0.46 mmol) in tetrahydrofuran (2.0 mL) at –20 to –25° C. After 25 min, iodomethane (0.032 mL, 73 mg, 0.51 mmol) was added. The reaction mixture was allowed to warm to room temperature over 2 h, and then was added to brine (10 mL) and extracted with ethyl acetate (2×25 mL). The organic layers were dried over sodium sulfate, decanted, and evaporated. Purification by flash column chromatography (silica gel, 3% methanol/dichloromethane) gave a racemic mixture of regioisomeric methylation products. The first-eluting enantiomer of the major regioisomer was isolated by preparative HPLC on a CHIRALCEL OD column, eluting with 12% 2-propanol/hexanes. Further purification by preparative HPLC on a CHIRALPAK AD column, eluting with 7% ethanol in hexanes, gave the enantiomer of the title compound used to prepare the more active diastereomer listed in Table 2. LC/MS 306 (M+1).

Step C: 1-Methyl-4-(trifluoromethyl)-4,5,6,7-tetrahydro-1H-imidazo[4,5-c]pyridine A solution of methanolic hydrogen chloride (about 1.6M, 3.0 mL) was added to tert-butyl 1-methyl-4-(trifluoromethyl)-1,4,6,7-tetrahydro-5H-imidazo[4,5-c]pyridine-5-carboxylate (42 mg, 0.14 mmol) dissolved in 0.50 mL of methanol. After 3 h, the solution was concentrated under a stream of nitrogen. Methanol (two portions) was added, with evaporation of the solvent after each addition. The residue was loaded onto a Varian SCX ion exchange column which was then washed with methanol. Elution with 1M methanolic ammonia and concentration of the resultant fractions yielded the title compound.

$^1$H NMR (500 MHz, CD$_3$OD) δ 7.55 (s, 1H), 4.33 (q, 1H, J=8 Hz), 3.60 (s, 3H), 3.24-3.17 (m, 1H), 3.11 (dt, 1H, J=13, 5 Hz), 2.66-2.57 (m, 2H). LC/MS 206 (M+1).

PIPERIDINE INTERMEDIATE 49

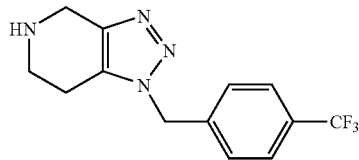

1-[4-(Trifluoromethyl)benzyl]-4,5,6,7-tetrahydro-1H-[1,2,3]triazolo[4,5-c]pyridine Step A: 3-Nitro-N-{[4-(trifluoromethyl)benzyl]amino}pyridin-4-amine To a solution of 1.4 g (8.3 mmol) of 4-ethoxy-3-nitropyridine in 30 mL of ethanol was added 1.45 g (1.18 mL, 8.3 mmol) of 4-(trifluoromethyl)benzylamine and the mixture was heated at reflux temperature for 20 h. The reaction was cooled and resultant yellow sold was collected and washed with a small amount of ethanol to give the title compound. LC/MS 298 (M+1).

Step B: N$^4$-[4-(trifluoromethyl)benzyl]pyridine-3,4-diamine

To a solution of 592 mg (2.0 mmol) of 3-nitro-N-[4-(trifluoromethyl)benzyl]pyridin-4-amine in 5 mL of dry N,N-dimethylformamide was added 1.3 g (6.0 mmol, 3 eq.) of tin (II) chloride dihydrate, and the mixture was heated in an oil bath at 60° C. for 4 h. The solvent was removed under vacuum and the residue was partitioned between ethyl acetate and water. The solid was filtered off. The filtrate was made basic by the addition of ammonium hydroxide and the solid formed was filtered off. The filtrate was evaporated to give the title compound. LC/MS 268 (M+1).

Step C: 1-[4-(trifluoromethyl)benzyl]-1H-[1,2,3]triazolo[4,5-c]pyridine

To a solution of 550 mg (2.06 mmol) of 3-amino-N-[4-(trifluoromethyl)benzyl]pyridinamine in 10 mL of 10% hydrochloric acid at 0° C. was added dropwise a solution of 1.5 g (21.7 mmol) of sodium nitrite in 10 mL of water. The mixture was stirred at 0° C. for 1 h and then concentrated to dryness. The residue was partitioned between chloroform and a small amount of water and the solution was made basic by the addition of ammonium hydroxide. The organics were separated and the water layer was extracted with two portions of chloroform. The combined organics were washed with brine, dried over magnesium sulfate, and filtered. Concentration of the filtrate gave the title compound as an off-white solid. LC/MS 279 (M+1).

Step D: 1-[4-(Trifluoromethyl)benzyl]-4,5,6,7-tetrahydro-1H-[1,2,3]triazolo[4,5-c]pyridine To a solution of 200 mg (0.75 mmol) of 1-[4-(trifluoromethyl)benzyl]-1H-[1,2,3]triazolo[4,5-c]pyridine in 10 mL of ethanol was added 50 mg of platinum(IV) oxide and the mixture was hydrogenated at 40 psi for 3 d. The mixture was filtered through a pad of Celite, and the Celite was washed with a small amount of ethanol. Concentration of the filtrate gave the title compound. LC/MS 283 (M+1).

PIPERIDINE INTERMEDIATE 50

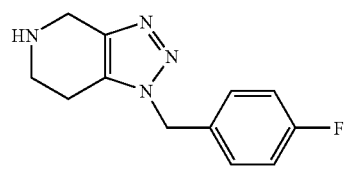

1-(4-Fluorobenzyl)-4,5,6,7-tetrahydro-1H-[1,2,3]triazolo[4,5-c]pyridine

The title compound was prepared essentially following the procedures described for the synthesis of PIPERIDINE INTERMEDIATE 49. LC/MS 233 (M+1).

PIPERIDINE INTERMEDIATE 51

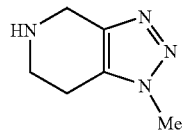

1-Methyl-4,5,6,7-tetrahydro-1H-[1,2,3]triazolo[4,5-c]pyridine

The title compound was prepared essentially following the procedures described for the synthesis of PIPERIDINE INTERMEDIATE 49. LC/MS 139 (M+1).

PIPERIDINE INTERMEDIATE 52

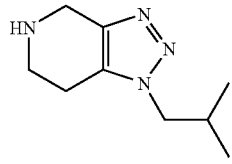

1-Isobutyl-4,5,6,7-tetrahydro-1H-[1,2,3]triazolo[4,5-c]pyridine

The title compound was prepared essentially following the procedures described for the synthesis of PIPERIDINE INTERMEDIATE 49. LC/MS 181 (M+1)

PIPERIDINE INTERMEDIATE 53

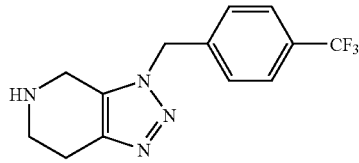

3-[4-(Trifluoromethyl)benzyl]-4,5,6,7-tetrahydro-3H-[1,2,3]triazolo[4,5-c]pyridine Step A: 3-fluoro-4-nitro-1$\lambda^5$-pyridin-1-ol To a solution of 5 g (51 mmol) of 3-fluoropyridine in 30 mL of acetic acid was added 11 mL (103 mmol) of 30% aqueous hydrogen peroxide. The mixture was heated at 70° C. for 9 h and then kept overnight at ambient temperature. After concentration under reduced pressure, the residue was made alkaline with excess sodium carbonate (solid) and then diluted with 30 mL of chloroform and stirred for 30 min. The solid was filtered off and the organics were dried over anhydrous sodium sulfate. Evaporation of the solvent gave the desired N-oxide. The N-oxide (4.87 g. 34 mmol) was dissolved in 20 mL of sulfuric acid and cooled to 0° C. To this cooled solution was added with caution a mixture of 33 mL of fuming nitric acid and 20 mL of sulfuric acid. After heating at 90° C. for 1.5 h, the mixture was poured into ice and then neutralized by the addition of ammonium carbonate. The organics were extracted with three portions of ethyl acetate and dried over magnesium sulfate. Evaporation of the solvent gave the title compound.

Step B: 4-nitro-3-[[4-(trifluoromethyl)benzyl]amino]-1$\lambda^5$-pyridin-1-ol

To a solution of 1 g (7 mmol) of 3-fluoro-4-nitro-1$\lambda^5$-pyridin-1-ol in 30 mL of ethanol was added 1.23 g (7 mmol) of 4-(trifluoromethyl)benzylamine and the mixture was heated at reflux temperature for 2 d. The reaction was cooled and concentrated. Purification by flash chromatography (silica gel, 45% ethyl acetate/hexane) afforded the title compound. LC/MS 314 (M+1).

Step C: 4-Nitro-3-[[4-(trifluoromethyl)benzyl]amino]pyridine

To a solution of 890 mg (2.84 mmol) of 4-nitro-3-[[4-(trifluoromethyl)benzyl]amino]-1$\lambda^5$-pyridin-1-ol in 20 mL of chloroform was added 3 mL (excess) of phosphorus trichloride and the mixture was heated at reflux temperature for 1 h. The mixture was concentrated and the residue was dissolved in a mixture of ice and water. The solution was neutralized with potassium carbonate (solid) and then extracted with three portions of ether. The combined organics were dried over magnesium sulfate and concentrated. The crude material was used in the next step without purification. LC/MS 298 (M+1).

Step D. 3-[4-(Trifluoromethyl)benzyl]-4,5,6,7-tetrahydro-3H-[1,2,3]triazolo[4,5-c]pyridine The title compound was prepared from 594 mg (2 mmol) of 4-nitro-3-[[4-(trifluoromethyl)benzyl]amino]pyridine essentially following the procedures described for PIPERIDINE INTERMEDIATE 49, Step B, C and D. LC/MS 283 (M+1).

PIPERIDINE INTERMEDIATE 54

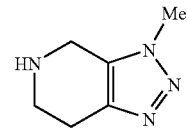

3-Methyl-4,5,6,7-tetrahydro-3H-[1,2,3]triazolo[4,5-c]pyridine

The title compound was essentially following the procedures described for the synthesis of PIPERIDINE INTERMEDIATE 53. LC/MS 139 (M+1).

Procedure 1:

Coupling of Acid Intermediates 1-13 with Fused Piperidine Intermediates 14-54 to Give N-Boc Amide Method A To a solution of about 1 equiv of fused piperidine intermediate, about 1 equiv of N-BOC acid intermediate, and, if the fused piperidine intermediate is a salt, 1-3 equiv of N,N-diisopropylethylamine in DMF or dichloromethane was added about 1.2 equiv of HOBT and about 1.2 equiv of EDC. The resultant mixture was stirred at ambient temperature overnight, and then partitioned between ethyl acetate and saturated aqueous sodium bicarbonate solution. The aqueous phase was extracted with several portions of ethyl acetate. The combined organic phases were washed with brine, dried over magnesium sulfate, and concentrated. Purification by flash chromatography (silica gel), HPLC, or preparative TLC gave the coupled product.

Method B

To a solution of about 1 equiv of fused piperidine in DMF is added about 1.1 equiv of N-BOC acid intermediate, followed by excess N,N-diisopropylethylamine, about 1.1 equiv of 1-hydroxy-7-azabenzotriazole, and about 1.1 equiv of HATU reagent. After 1-16 h at ambient temperature, the reaction was diluted with aqueous sodium bicarbonate solution and extracted with ethyl acetate. The organic layer was washed with brine, dried over magnesium sulfate, and concentrated in vacuo. Purification by flash chromatography (silica gel), HPLC, or preparative TLC afforded the coupled product.

Method C

To a solution of 1 equiv of N-Boc acid intermediate and about 1.1 equiv of N-methylmorpholine in dichloromethane at 0° C. was added 1 equiv of pivaloyl chloride. After 1 h, a solution of about 1 equiv of fused piperidine intermediate, about 1.1 equiv of N-methylmorpholine, and about 0.25 equiv of 4-(dimethylamino)pyridine in dichloromethane was added. The mixture was allowed to warm to room temperature and stirred overnight. The reaction was diluted with aqueous sodium bicarbonate solution and extracted with ethyl acetate. The organic layer was washed with brine, dried over sodium sulfate, and concentrated in vacuo. Purification by flash chromatography (silica gel), HPLC, or preparative TLC afforded the coupled product.

Method D

In a variation of Method A, a solution of about 1 equiv of fused piperidine intermediate and about 1 equiv of N-BOC acid intermediate in dichloromethane (about 6-9 mL/mmol of fused piperidine) was treated with about 1.5 equiv of HOBT, about 1.2 equiv of EDC, and about 3 equiv of N,N-diisopropylethylamine. The resultant mixture was stirred at ambient temperature for 3-24 h. Then additional quantities of HOBT (about 1 equiv), EDC (about 0.75 equiv), and N,N-diisopropylethylamine (about 20-25% by volume relative to dichloromethane) were added, and the solution was stirred at reflux temperature for about 1-3 days. The reaction mixture was then concentrated in vacuo. Purification by flash chromatography (silica gel), HPLC, or preparative TLC afforded the coupled product.

Method E

In a variation of Method B, a solution of about 1 equiv of fused piperidine in dichloromethane (about 6-9 mL/mmol of fused piperidine) was treated with about 1 equiv. of N-BOC acid intermediate, followed by about 1.2 equiv. of 1-hydroxy-7-azabenzotriazole, about 1.5 equiv of HATU reagent, and about 2.5-3 equiv of N,N-diisopropylethylamine. After about 1.5-3 h, a large excess of additional N,N-diisopropylethylamine (about 20-40% by volume relative to dichloromethane) was added, and stirring at ambient temperature was continued for 1-3 days. The reaction mixture was then concentrated in vacuo. Purification by flash chromatography (silica gel), HPLC, or preparative TLC afforded the coupled product.

Procedure 2:

Deprotection of N-Boc Amides from Procedure 1 to Give Final Products

Method A

A solution of N-BOC coupled product from Procedure 1 in 1:1 trifluoroacetic acid/dichloromethane was stirred at ambient temperature for 0.5-2 h. Concentration gave the deprotected product as its TFA salt.

The product may be further purified by reverse-phase HPLC (YMC Pro-C18 column, gradient elution, typically 10-90% acetonitrile/water with 0.1% TFA) to give the product as its TFA salt.

Method B

A solution of N-BOC coupled product from Procedure 1 in saturated methanolic hydrogen chloride was stirred at ambient temperature for 1-2 h. Concentration gave the deprotected product as its HCl salt.

The product may be further purified by reverse-phase HPLC (YMC Pro-C18 column, gradient elution, typically 10-90% acetonitrile/water with 0.1% TFA) to give the product as its TFA salt.

Method C

The N-BOC coupled product from Procedure 1 was treated with 4M hydrogen chloride in anhydrous dioxane. The mixture was stirred at room temperature for 0.5-2 h. Concentration gave the deprotected product as its HCl salt.

The product may be further purified by reverse-phase HPLC (YMC Pro-C18 column, gradient elution, typically 10-90% acetonitrile/water with 0.1% TFA) to give the product as its TFA salt.

Essentially following Procedures 1 and 2, the compounds listed in Table 2 were prepared.

TABLE 2

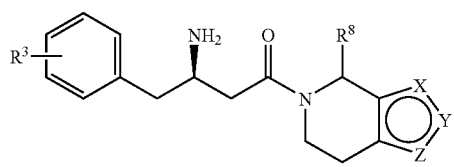

| Ex. | $R^3$ | $R^8$ | X | Y | Z | MS (M + 1) |
|---|---|---|---|---|---|---|
| 1 | 2-F | H | CH | CH | S | 319.2 |
| 2 | 2-F | H | CH | Br | S | 397.1, 399.1 |

TABLE 2-continued

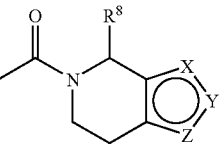

| Ex. | R³ | R⁸ | X | Y | Z | MS (M + 1) |
|---|---|---|---|---|---|---|
| 3 | 2-F, 5-F | H | CH | 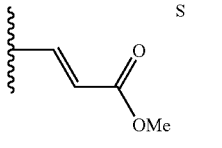 | S | 421.2 |
| 4 | 2-F, 5-F | H | CH | 4-COOMe—Ph | S | 471.2 |
| 5 | 2-F, 5-F | H | C—CH₃ | N | NH | 335 |
| 6 | 2-F, 5-F | H | C—CF₃ | N | NH | 389 |
| 7 | 2-F, 5-F | H | C—CF₂CF₃ | N | NH | 439 |
| 8 | 2-F, 5-F | H | C-(4-F—Ph) | N | NH | 415 |
| 9 | 2-F, 5-F | H | C—CF₃ | N | N—Me | 403 |
| 10 | 2-F, 5-F | H | C—CF₃ | N | N—CH₂CF₃ | 471 |
| 11 | 2-F, 5-F | H | NH | N | C—CF₃ | 389 |
| 12 | 2-F, 5-F | H | NH | N | C-cyclopropyl | 361 |
| 13 | 2-F, 5-F | H | N—Me | N | C—CF₃ | 403 |
| 14 | 2-F, 5-F | H | C—CF₃ | O | N | 390 |
| 15 | 2-F, 5-F | H | N | O | C—CF₃ | 390 |
| 16 | 2-F, 5-F | H | S | C-(4-CF₃—Ph) | N | 482 |
| 17 | 2-F, 5-F | H | S | C-(4-SO₂Me—Ph) | N | 492 |
| 18 | 2-F, 5-F | H | N | C-(4-F—Ph) | S | 432 |
| 20 | 2-F, 5-F | H | N | C-(4-CF₃—Ph) | S | 482 |
| 21 | 2-F, 5-F | H | N | C-(4-SO₂Me—Ph) | S | 492 |
| 22 | 2-F, 5-F | H | N | C—CF₃ | S | 406 |
| 23 | 2-F, 5-F | H | N | C-cyclopropyl | O | 362 |
| 24 | 2-F, 5-F | H | O | C—CF₃ | N | 362 |
| 25 | 2-F, 5-F | H | N | C—CF₃ | NH | 390 |
| 26 | 2-F, 5-F | H | N | C—Ph | NH | 397 |
| 27 | 2-F, 5-F | H | N | C—CF₃ | N—Me | 403 |
| 28 | 2-F, 5-F | H | N—Me | C—CF₃ | N | 403 |
| 29 | 2-F, 5-F | H | N | C—CF₃ | N—CH₂(4-F—Ph) | 497 |
| 30 | 2-F, 5-F | H | N-[CH₂(4-F—Ph)] | C—CF₃ | N | 497 |
| 31 | 2-F, 5-F | Me | N | C—CF₃ | N—Me | 417 |
| 32 | 2-F, 4-F, 5-F | Me | N | C—CF₃ | N—Me | 435 |
| 33 | 2-F, 4-F, 5-F | Et | N | C—CF₃ | N—Me | 449 |
| 34 | 2-F, 4-F, 5-F | Cyclopropyl | N | C—CF₃ | N—Me | 461 |
| 35 | 2-F, 4-F, 5-F | CH₂(4-F—Ph) | N | C—CF₃ | N—Me | 529 |
| 36 | 2-F, 4-F, 5-F | Me | N | C-cyclopropyl | N—Me | 407 |
| 37 | 2-F, 4-F, 5-F | CF₃ | N | CH | N—Me | 421 |
| 38 | 2-F, 4-F, 5-F | H | N | N | N—CH₂(4-CF₃—Ph) | 498 |
| 39 | 2-F, 5-F | H | N | N | N—CH₂(4-F—Ph) | 430 |
| 40 | 2-F, 4-F, 5-F | H | N | N | N—Me | 336 |
| 41 | 2-F, 5-F | H | N | N | N—CH₂CHMe₂ | 378 |
| 42 | 2-F, 4-F, 5-F | H | N—CH₂(4-CF₃—Ph) | N | N | 498 |
| 43 | 2-F, 4-F, 5-F | H | N—Me | N | N | 354 |

EXAMPLE OF A PHARMACEUTICAL FORMULATION

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

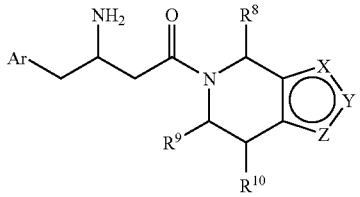

or a pharmaceutically acceptable salt thereof; wherein
each n is independently 0, 1, or 2;
X, Y and Z are independently selected from the group consisting of:
(1) $CR^1$,
(2) $NR^2$,
(3) N,
(4) O, and
(5) S;
with the provisos that at least one of X, Y and Z is not $CR^1$ and two of X, Y, and Z cannot be O and/or S;
Ar is phenyl substituted with one to five $R^3$ substituents;
each $R^1$ is independently selected from the group consisting of
hydrogen,
halogen,
hydroxy,
cyano,
$C_{1-10}$ alkyl, wherein alkyl is unsubstituted or substituted with one to five substituents independently selected from halogen or hydroxy,
$C_{1-10}$ alkoxy, wherein alkoxy is unsubstituted or substituted with one to five substituents independently selected from halogen or hydroxy,
$C_{1-10}$ alkylthio, wherein alkylthio is unsubstituted or substituted with one to five substituents independently selected from halogen or hydroxy,
$C_{2-10}$ alkenyl, wherein alkenyl is unsubstituted or substituted with one to five substituents independently selected from halogen, hydroxy, COOH, and $COOC_{1-6}$ alkyl,
$(CH_2)_nCOOH$,
$(CH_2)_nCOOC_{1-6}$ alkyl,
$(CH_2)_nCONR^4R^5$, wherein $R^4$ and $R^5$ are independently selected from the group consisting of hydrogen, tetrazolyl, thiazolyl, $(CH_2)_n$-phenyl, $(CH_2)_n$-$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are substituted with one to five halogens;
$(CH_2)_n$—$NR^4R^5$,
$(CH_2)_n$—$OCONR^4R^5$,
$(CH_2)_n$—$SO_2NR^4R^5$,
$(CH_2)_n$—$SO_2R^6$,
$(CH_2)_n$—$NR^7SO_2R^6$,
$(CH_2)_n$—$NR^7CONR^4R^5$,
$(CH_2)_n$—$NR^7COR^7$,
$(CH_2)_n$—$NR^7CO_2R^6$,
$(CH_2)_n$—$COR^7$,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $COOC_{1-6}$ alkyl, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens;
each $R^2$ is independently selected from the group consisting of
hydrogen,
$C_{1-10}$ alkyl, wherein alkyl is unsubstituted or substituted with one to five substituents independently selected from halogen or hydroxy,
$C_{2-10}$ alkenyl, wherein alkenyl is unsubstituted or substituted with one to five substituents independently selected from halogen or hydroxy,
$(CH_2)_nCOOH$,
$(CH_2)_nCOOC_{1-6}$ alkyl,
$(CH_2)_nCONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_nCOOC_{1-6}$ alkyl, $C_{1-6}$ alkyl, and $C_{1-6}$ alkoxy, wherein alkyl and alkoxy are unsubstituted or substituted with one to five halogens or one phenyl;

$(CH_2)_n$—$COR_7$,
$(CH_2)_n$—$SO_2NR^4R^5$,
$(CH_2)_n$—$SO_2R^6$,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $C_{1-6}$ alkyloxycarbonyl, $C_{1-6}$ alkyl, and
$C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens;
each $R^3$ is independently selected from the group consisting of
hydrogen,
halogen,
cyano,
hydroxy,
$C_{1-6}$ alkyl, unsubstituted or substituted with one to five halogens, and
$C_{1-6}$ alkoxy, unsubstituted or substituted with one to five halogens;
$R^6$ is independently selected from the group consisting of
tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^7$ is hydrogen or $R^6$;
$R^8$, $R^9$ and $R^{10}$ are each independently selected from the group consisting of
hydrogen,
cyano,
$(CH_2)_n COOH$,
$(CH_2)_n COOC_{1-6}$ alkyl,
$C_{1-6}$ alkyloxycarbonyl,
$C_{1-10}$ alkyl, unsubstituted or substituted with one to five substituents independently selected from halogen, hydroxy, $C_{1-6}$ alkoxy, and phenyl-$C_{13}$ alkoxy, wherein alkoxy is unsubstituted or substituted with one to five halogens,
$(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and
$(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $(CH_2)_n COOC_{1-6}$ alkyl, $C_{1-6}$ alkyl, and $C_{1-6}$ alkoxy, wherein alkyl and alkoxy are unsubstituted or substituted with one to five halogens or one phenyl; and
wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

2. The compound of claim 1 of the structural formula Ia wherein the carbon atom marked with an * has the R stereochemical configuration

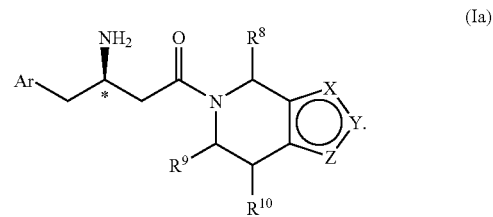

(Ia)

3. The compound of claim 1 of the structural formula Ib

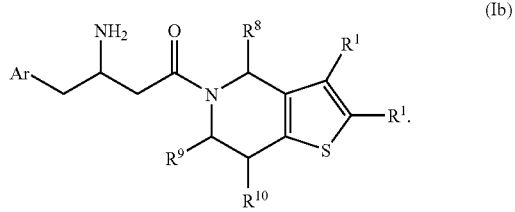

4. The compound of claim 3 of the structural formula Ic wherein the carbon atom marked with an * has the R stereochemical configuration

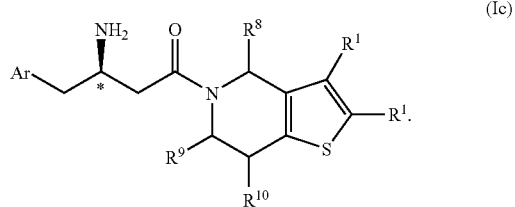

5. The compound of claim 3 wherein $R^9$ and $R^{10}$ are hydrogen.

6. The compound of claim 1 of the structural formula Ie

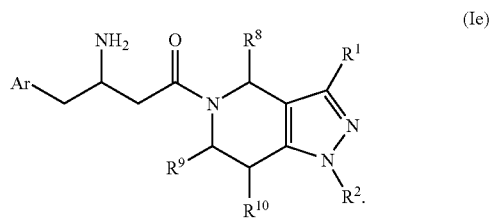

7. The compound of claim 6 of the structural formula If wherein the carbon atom marked with an * has the R stereochemical configuration

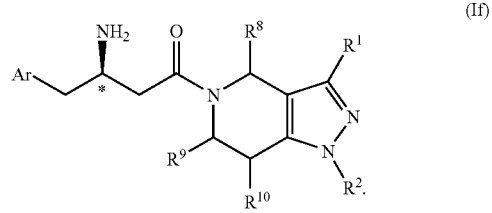

8. The compound of claim 6 wherein $R^9$ and $R^{10}$ are hydrogen.

9. The compound of claim 1 of the structural formula Ih

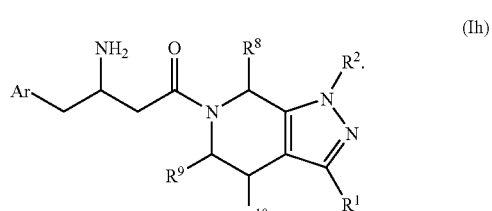

10. The compound of claim 9 of the structural formula Ii wherein the carbon atom marked with an * has the R stereochemical configuration

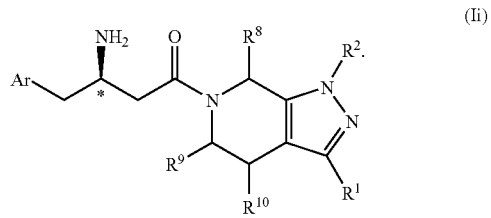

11. The compound of claim 9 wherein $R^9$ and $R^{10}$ are hydrogen.

12. The compound of claim 1 of the structural formula Ik

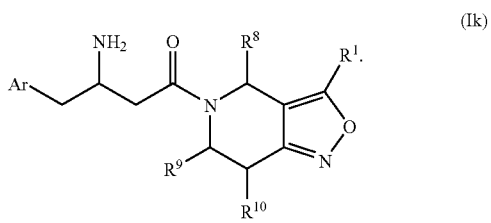

13. The compound of claim 12 of the structural formula Il wherein the carbon atom marked with an * has the R stereochemical configuration

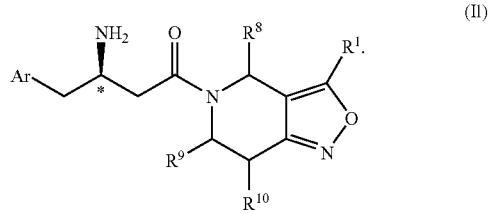

14. The compound of claim 12 wherein $R^9$ and $R^{10}$ are hydrogen.

15. The compound of claim 1 of the structural formula In

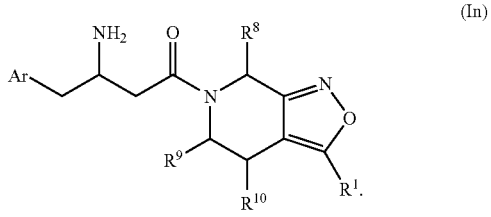

16. The compound of claim 15 of the structural formula Io wherein the carbon atom marked with an * has the R stereochemical configuration

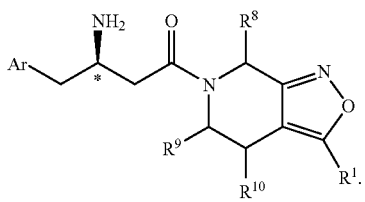

(Io)

17. The compound of claim 15 wherein $R^9$ and $R^{10}$ are hydrogen.

18. The compound of claim 1 of structural formula Iq

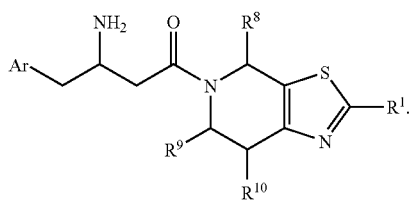

(Iq)

19. The compound of claim 18 of the structural formula Ir wherein the carbon atom marked with an * has the R stereochemical configuration

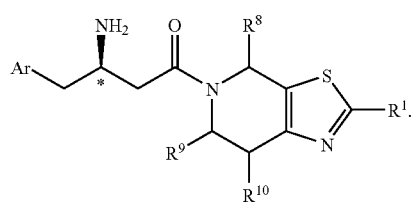

(Ir)

20. The compound of claim 18 wherein $R^9$ and $R^{10}$ are hydrogen.

21. The compound of claim 1 of the structural formula It

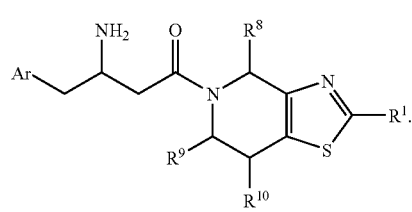

(It)

22. The compound of claim 21 of the structural formula Iu wherein the carbon atom marked with an * has the R stereochemical configuration

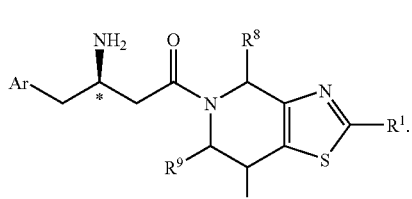

(Iu)

23. The compound of claim 21 wherein $R^9$ and $R^{10}$ are hydrogen.

24. The compound of claim 1 of the structural formula Iw

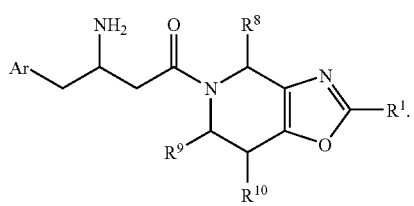

(Iw)

25. The compound of claim 24 of the structural formula Ix wherein the carbon atom marked with an * has the R stereochemical configuration

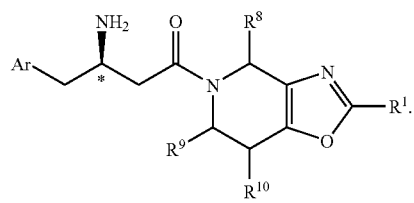

(Ix)

26. The compound of claim 24 wherein $R^9$ and $R^{10}$ are hydrogen.

27. The compound of claim 1 of the structural formula Iz

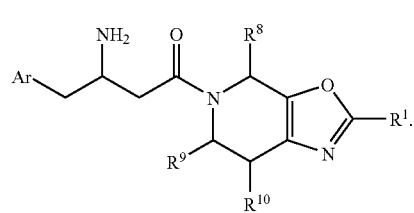

(Iz)

28. The compound of claim 27 of the structural formula Iaa wherein the carbon atom marked with an * has the R stereochemical configuration

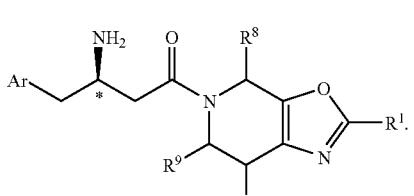

(Iaa)

29. The compound of claim 27 wherein $R^9$ and $R^{10}$ are hydrogen.

30. The compound of claim 1 of the structural formula Iac

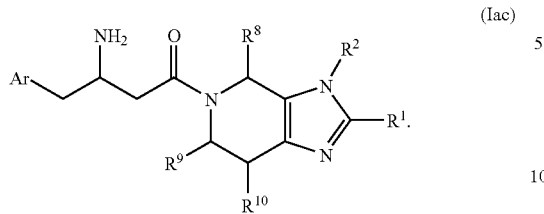
(Iac)

31. The compound of claim 30 of the structural formula Iad wherein the carbon atom marked with an * has the R stereochemical configuration

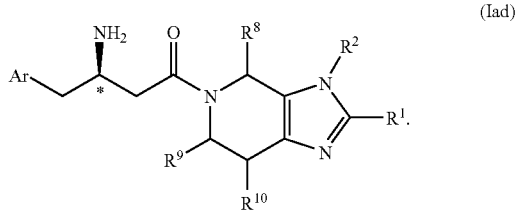
(Iad)

32. The compound of claim 30 wherein $R^9$ and $R^{10}$ are hydrogen.

33. The compound of claim 1 of the structural formula Iaf

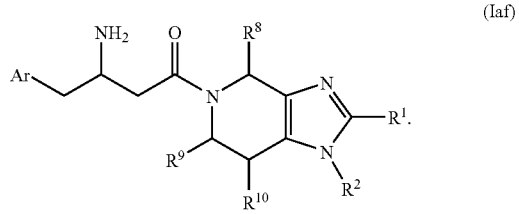
(Iaf)

34. The compound of claim 33 of the structural formula Ig wherein the carbon atom marked with an * has the R stereochemical configuration

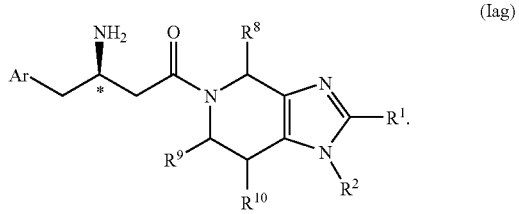
(Iag)

35. The compound of claim 33 wherein $R^9$ and $R^{10}$ are hydrogen.

36. The compound of claim 1 of the structural formula Iai

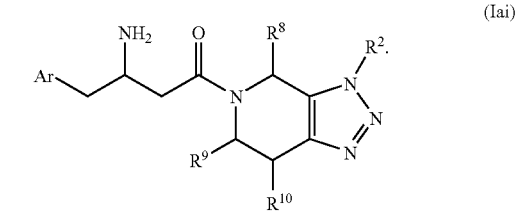
(Iai)

37. The compound of claim 36 of the structural formula Iaj wherein the carbon atom marked with an * has the R stereochemical configuration

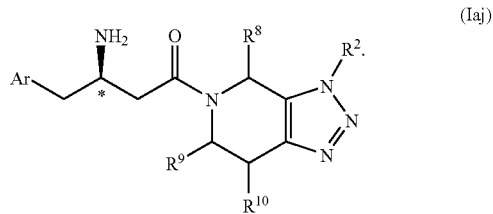
(Iaj)

38. The compound of claim 36 wherein $R^9$ and $R^{10}$ are hydrogen.

39. The compound of claim 1 of the structural formula Ial

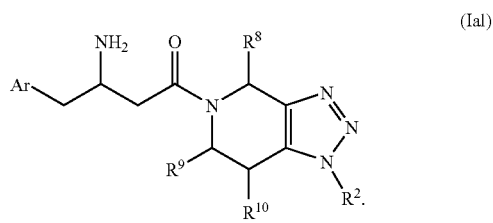
(Ial)

40. The compound of claim 39 of the structural formula Iam wherein the carbon atom marked with an * has the R stereochemical configuration

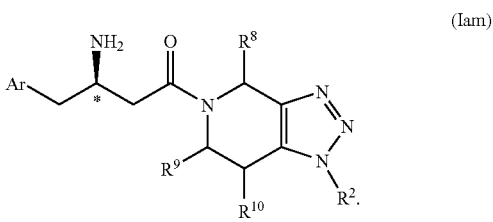
(Iam)

41. The compound of claim 39 wherein $R^9$ and $R^{10}$ are hydrogen.

42. The compound of claim 1 wherein $R^3$ is selected from the group consisting of hydrogen, fluoro, chloro, bromo, trifluoromethyl, and methyl.

43. The compound of claim 1 wherein $R^1$ is selected from the group consisting of:
hydrogen,
halogen,
hydroxy,
$C_{1-10}$ alkyl, wherein alkyl is unsubstituted or substituted with one to five substituents independently selected from halogen or hydroxy,
$C_{2-10}$ alkenyl, wherein alkenyl is unsubstituted or substituted with one to five substituents independently selected from halogen, hydroxy, COOH, and $COOC_{1-6}$ alkyl,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and (CH$_2$)$_n$-aryl, wherein aryl is unsubstituted or substituted with one to five substituents independently selected from halogen, cyano, hydroxy, NR$^7$SO$_2$R$^6$, SO$_2$R$^6$, CO$_2$H, COOC$_{1-6}$ alkyl, C$_{1-6}$ alkyl, and
C$_{1-6}$ alkoxy, wherein alkyl and alkoxy are unsubstituted or substituted with one to five halogens; and wherein any methylene (CH$_2$) carbon atom in R$^1$ is unsubstituted or substituted with one to two groups independently selected from halogen, hydroxy, and C$_{1-4}$ alkyl unsubstituted or substituted with one to five halogens.

44. The compound of claim 43 wherein R$^1$ is selected from the group consisting of
hydrogen,
methyl,
ethyl,
trifluoromethyl,
CH$_2$CF$_3$,
CF$_2$CF$_3$,
phenyl,
4-(methoxycarbonyl)phenyl,
4-fluorophenyl,
4-(trifluoromethyl)phenyl,
4-(methylsulfonyl)phenyl,
cyclopropyl,
fluoro,
chloro,
bromo, and
2-(methoxycarbonyl)vinyl.

45. The compound of claim 1 wherein R$^2$ is selected from the group consisting of
hydrogen,
C$_{1-6}$ alkyl, wherein alkyl is unsubstituted or substituted with one to five substituents independently selected from halogen or hydroxy,
(CH$_2$)$_n$-aryl, wherein aryl is unsubstituted or substituted with one to five substituents independently selected from halogen, CN, hydroxy, NR$^7$SO$_2$R$^6$, SO$_2$R$^6$, CO$_2$H, COOC$_{1-6}$ alkyl, C$_{1-6}$ alkyl, and
C$_{1-6}$ alkoxy, wherein alkyl and alkoxy are unsubstituted or substituted with one to five halogens; and
wherein any methylene (CH$_2$) carbon atom in R$^2$ is unsubstituted or substituted with one to two groups independently selected from halogen, hydroxy, and C$_{1-4}$ alkyl unsubstituted or substituted with one to five halogens.

46. The compound of claim 45 wherein R$^2$ is selected from the group consisting of:
hydrogen,
methyl,
CH$_2$CF$_3$,
isobutyl,
4-(trifluoromethyl)benzyl, and
4-fluorobenzyl.

47. The compound of claim 1 wherein R$^8$, R$^9$, and R$^{10}$ are independently selected from the group consisting of:
hydrogen,
C$_{1-10}$ alkyl, unsubstituted or substituted with one to five substituents independently selected from halogen, hydroxy, C$_{1-6}$ alkoxy,
and phenyl-C$_{13}$ alkoxy, wherein alkoxy is unsubstituted or substituted with one to five halogens,
(CH$_2$)$_n$-aryl, wherein aryl is unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens, (CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, and wherein any methylene (CR$^2$) carbon atom in R$^8$, R$^9$ or R$^{10}$ is unsubstituted or substituted with one to two groups independently selected from halogen, hydroxy, and C$_{1-4}$ alkyl unsubstituted or substituted with one to five halogens.

48. The compound of claim 47 wherein R$^8$, R$^9$, and R$^{10}$ are each independently selected from the group consisting of
hydrogen,
trifluoromethyl,
methyl,
ethyl,
cyclopropyl,
CR$^2$-Ph, and
CR$^2$(4-F-Ph).

49. The compound of claim 48 wherein R$^9$ and R$^{10}$ are hydrogen.

50. The compound of claim 49 which is selected from the group consisting of:

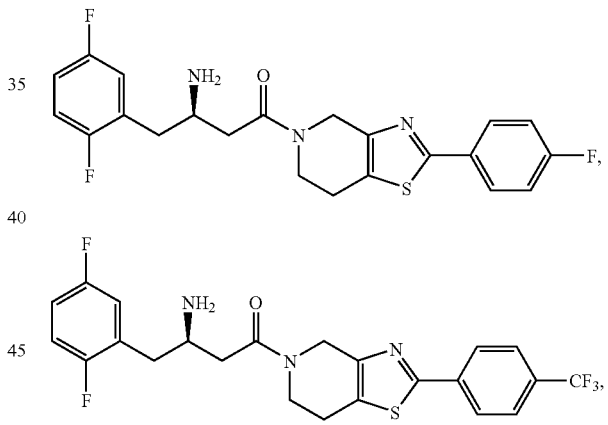

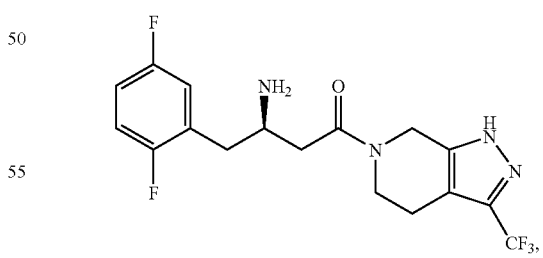

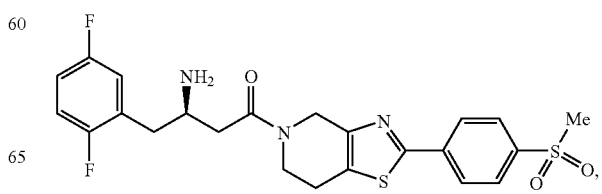

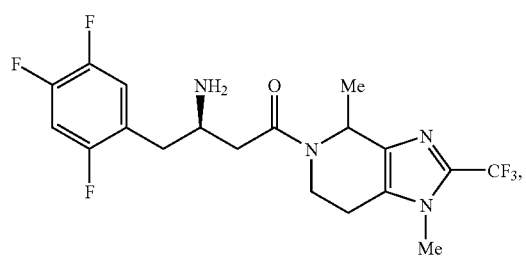
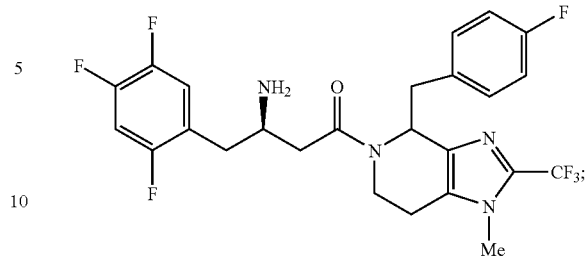
or a pharmaceutically acceptable salt thereof.
51. A pharmaceutical composition which comprises a compound of claim 1 and a pharmaceutically acceptable carrier.
52. A method for treating non-insulin dependent (Type 2) diabetes in a mammal in need thereof which comprises the administration to the mammal of a therapeutically effective amount of a compound of claim 1.
* * * * *